United States Patent
Brusko et al.

(10) Patent No.: US 11,022,615 B2
(45) Date of Patent: Jun. 1, 2021

(54) REGULATORY T-CELLS, METHOD FOR THEIR ISOLATION AND USES

(71) Applicant: UNIVERSITY OF FLORIDA RESEARCH FOUNDATION, INC., Gainesville, FL (US)

(72) Inventors: Todd M. Brusko, Gainesville, FL (US); Christopher Fuhrman, Cambridge, MA (US); Howard R. Seay, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 167 days.

(21) Appl. No.: 15/571,823

(22) PCT Filed: May 4, 2016

(86) PCT No.: PCT/US2016/030789
§ 371 (c)(1),
(2) Date: Nov. 4, 2017

(87) PCT Pub. No.: WO2016/179288
PCT Pub. Date: Nov. 10, 2016

(65) Prior Publication Data
US 2018/0356427 A1  Dec. 13, 2018

Related U.S. Application Data

(60) Provisional application No. 62/156,506, filed on May 4, 2015.

(51) Int. Cl.
| | | |
|---|---|---|
| G01N 33/68 | (2006.01) |
| A61K 35/17 | (2015.01) |
| C12N 5/0783 | (2010.01) |
| G01N 15/14 | (2006.01) |

(52) U.S. Cl.
CPC ......... *G01N 33/6854* (2013.01); *A61K 35/17* (2013.01); *C12N 5/0637* (2013.01); *C12N 2501/2312* (2013.01); *G01N 15/1459* (2013.01); *G01N 2015/149* (2013.01); *G01N 2333/70503* (2013.01); *G01N 2333/70514* (2013.01)

(58) Field of Classification Search
None
See application file for complete search history.

(56) References Cited

U.S. PATENT DOCUMENTS

2009/0258013 A1* 10/2009 Clark ............... C07K 14/70503
424/133.1
2015/0132272 A1* 5/2015 Flavell .................. A61K 35/17
424/93.71

FOREIGN PATENT DOCUMENTS

WO  2015158855 A1  10/2015

OTHER PUBLICATIONS

Fuhrman et al. 'CD226 and TIGIT Identify Human Regulatory T Cells with Unique Functional Activities.' Diabetes Jun. 2014; 63 (Supplement 1): A176-OR.*
Yang et al. 'Helios but not CD226, TIGIT and Foxp3 is a Potential Marker for CD4+ Treg Cells in Patients with Rheumatoid Arthritis.' Cell Physiol Biochem 52;1178-1192, 2019.*
Mor et al., J. Immunol. 2005, vol. 175: 3439-3445.*
Chevalier et al., 2013, vol. 121: 29-37.*
Quinn et al. Best Pract. Res. Clin. Rheum. 15: 49-66, 2001.*
Progress in Auotimmune Disease Reserach, pp. 1-126, 2005.*
Cools et al. 'Regulatory T Cells and Human Disease.' Clinical and Developmental Immunology pp. 1-11, 2007. doi:10.1155/2007/89195.*
Joller, Nicole, et al., "Cutting Edge: TIGIT Has T Cell-Intrinsic Inhibitory Functions." The Journal of Immunology, Jan. 2011, 186: 1338-1342.
Liu, Weihong, et al., "CD127 expression inversely correlates with FoxP3 and suppressive function of human CD4+ T reg cells." The Journal of Experimental Medicine, Jul. 10, 2006, 203(7): 1701-1711.
Lozano, Ester, et al., "The TIGIT/CD226 Axis Regulates Human T Cell Function." The Journal of Immunology, Mar. 2012, 188: 3869-3875.
Putnam, Amy L., et al., "Expansion of Human Regulatory T-Cells From Patients With Type 1 Diabetes." Diabetes, Mar. 2009, 58(3): 652-662.

(Continued)

Primary Examiner — Nora M Rooney
(74) Attorney, Agent, or Firm — Timothy H. Van Dyke; Wolter Van Dyke Davis, PLLC

(57) ABSTRACT

The invention pertains to methods of isolating a Treg from a subject, the method comprising the steps of analyzing a sample of cells obtained from the subject to determine the level of expression of polypeptides and/or polynucleotides corresponding to proteins CD 127, CD4, CD25, and CD226 and isolating, as the Treg, a cell which expresses CD4 and CD25, expresses low levels of CD 127 or does not express CD 127, and expresses low levels of CD226 or does not express CD226. The Treg isolated from a subject can be proliferated in vitro. Accordingly, the invention also provides compositions comprising Treg isolated/proliferated according to the methods of the invention and pharmaceutically acceptable carrier and/or excipient. The pharmaceutical compositions can be used to treat and/or prevent inflammation mediated disease, for example, autoimmune diseases, such as, systemic lupus erythmatosus, rheumatoid arthritis, Multiple Sclerosis, type 1 diabetes, or inflammatory bowel disease.

8 Claims, 35 Drawing Sheets
Specification includes a Sequence Listing.

(56) References Cited

OTHER PUBLICATIONS

Trenado, Aurelie, et al., "Recipient-type specific CD4+CD25+ regulatory T cells favor immune reconstitution and control graft-versus-host disease while maintaining graft-versus-leukemia." The Journal of Clinical Investigation, Dec. 2003, 112(11): 1688-1696.

* cited by examiner

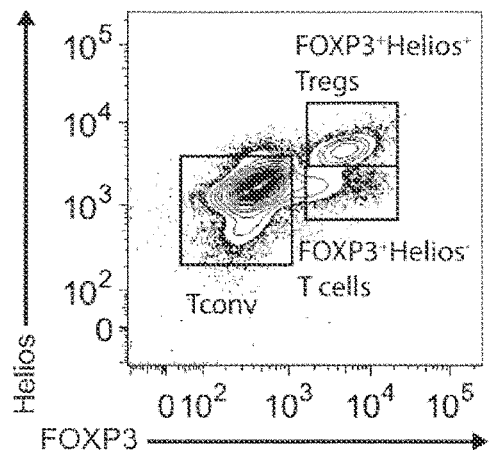
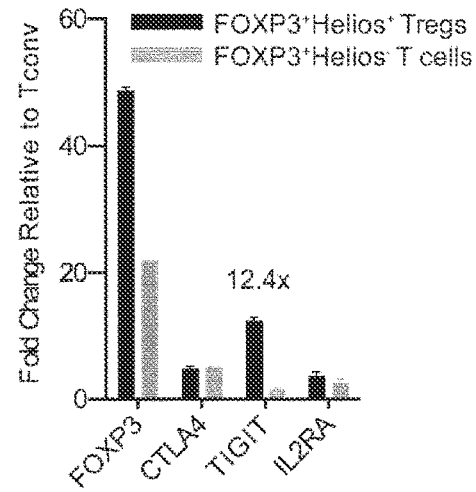
FIG. 1A
FIG. 1B
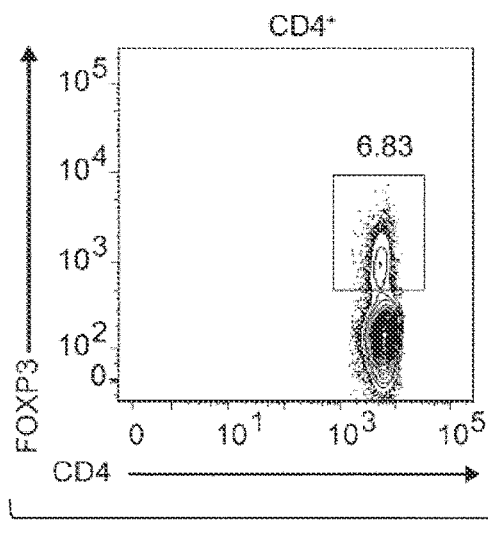
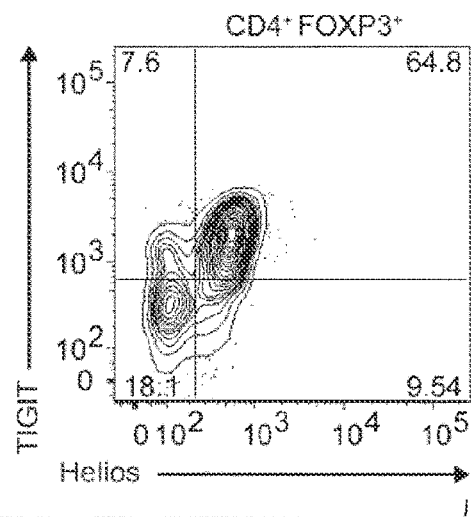
FIG. 1C

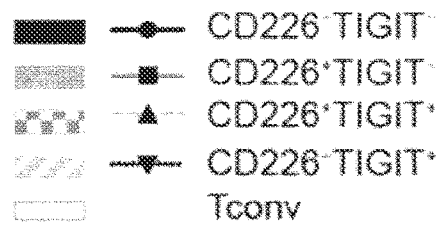
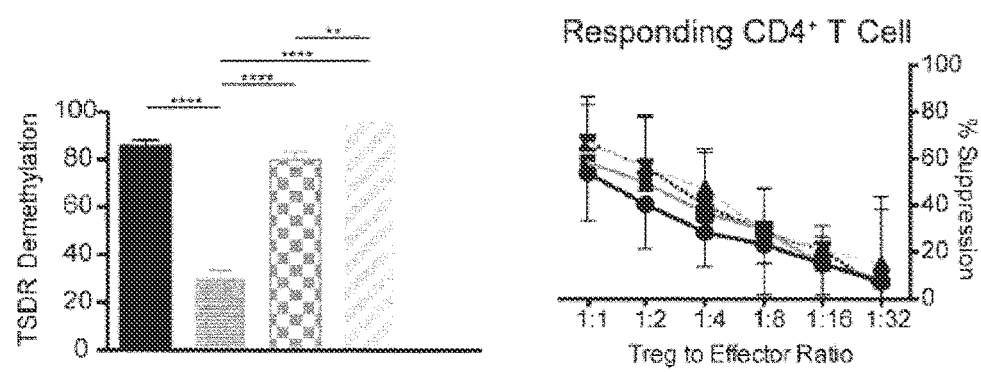
FIG. 4B
FIG. 4C
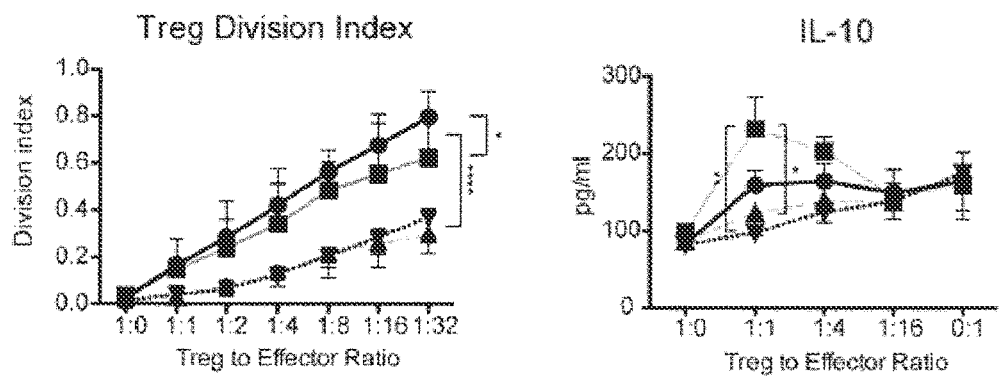
FIG. 4D
FIG. 4E

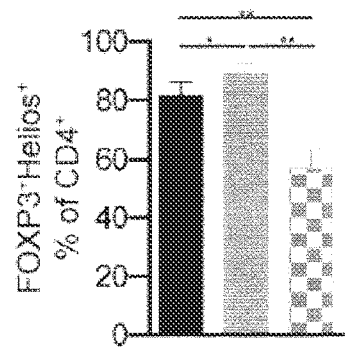
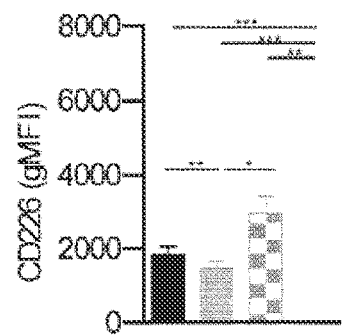
FIG. 7D  FIG. 7E
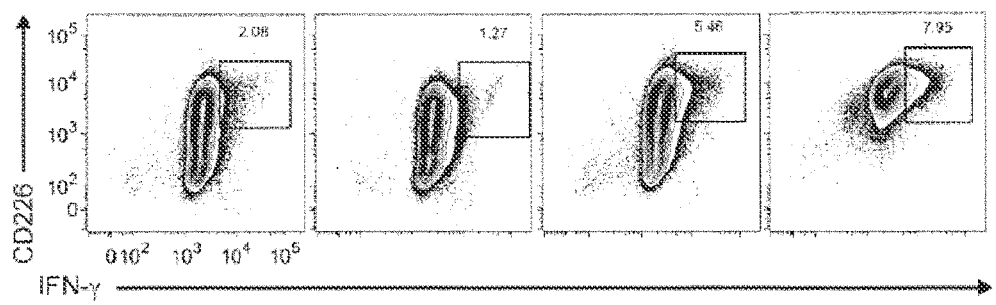
FIG. 7F
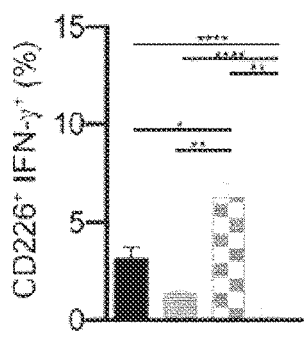
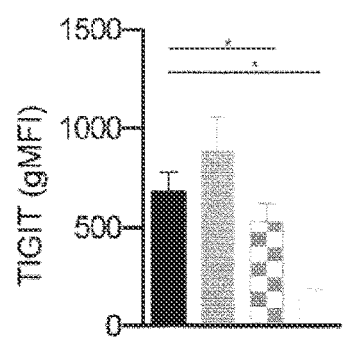
FIG. 7G  FIG. 7H

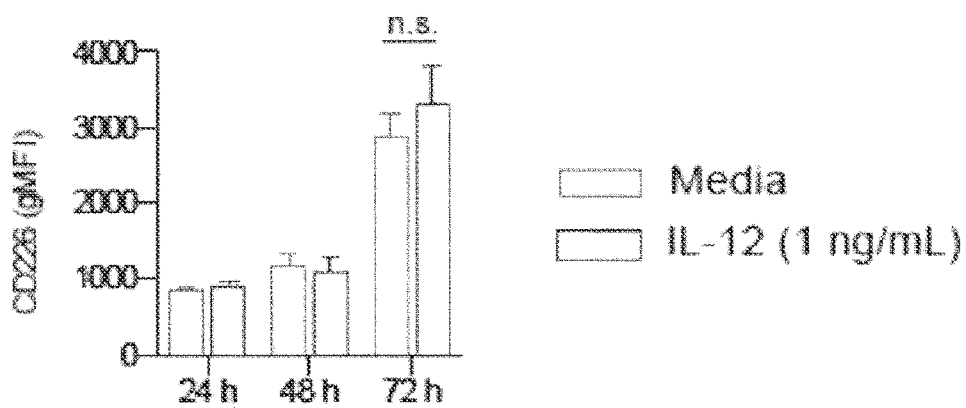
FIG. 8C
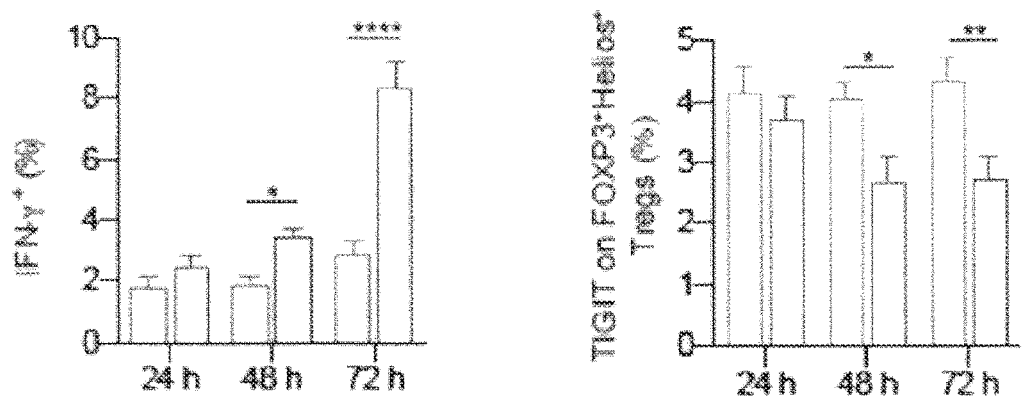
FIG. 8D
FIG. 8E

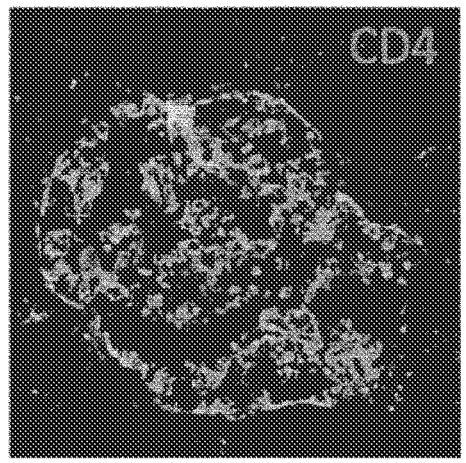
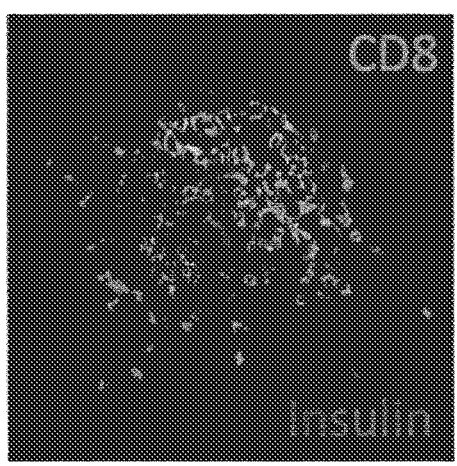
FIG. 18B	FIG. 18C
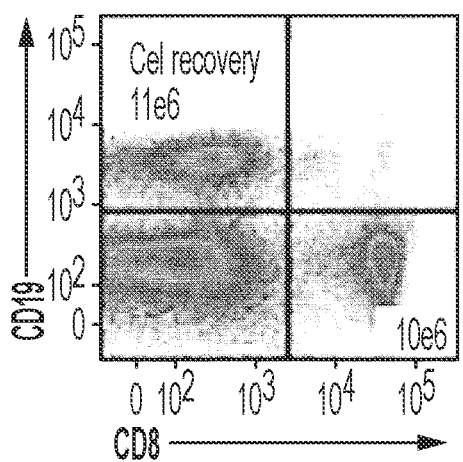
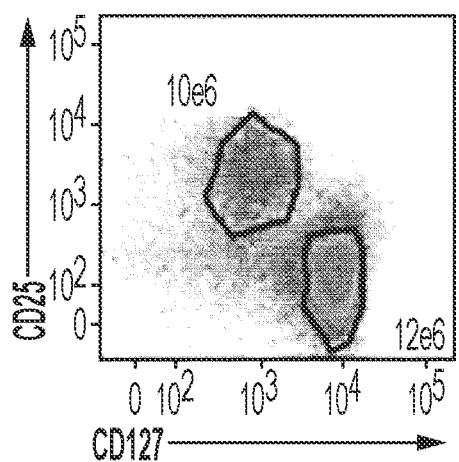
FIG. 19

REGULATORY T-CELLS, METHOD FOR THEIR ISOLATION AND USES

CROSS-REFERENCE TO A RELATED APPLICATION

This application is a National Stage Application of International Application Number PCT/US2016/030789, filed May 4, 2016; which claims the benefit of U.S. Provisional Patent Application Ser. No. 62/156,506, filed May 4, 2015, both of which are incorporated herein by reference in its their entirety.

The Sequence Listing for this application is labeled "SeqList-03May16-ST25.txt", which was created on May 3, 2016, and is 2 KB. The entire content is incorporated herein by reference in its entirety.

GOVERNMENT SUPPORT

This invention was made with government support under Grant Nos. AI042288 and DK106191 awarded by the National Institutes of Health. The government has certain rights in the invention.

BACKGROUND

The adaptive immune system provides a host with a vast receptor repertoire facilitating protection from a wide array of pathogens. One consequence of this incredible diversity is the development of T and B cells specific for self-tissues. To counteract this autoreactivity, the immune system employs mechanisms to reinforce peripheral immune tolerance, including a dominant role for a small population of $CD4^+$ regulatory T cells (Treg). The requirement for regulation is most apparent in individuals presenting with a mutation in the canonical transcription factor of the Treg lineage, FOXP3, which results in an X-linked fatal autoimmune disease.

Treg exert their suppressive properties through a variety of mechanisms, including tolerogenic enzymatic pathways, production of immunoregulatory cytokines, and expression of cell-surface expressed negative regulators. Of these, CTLA-4 and PD-1 have been subject to extensive investigation for their ability to regulate T cell activation through interactions with antigen presenting cells (APCs) and host tissues. Moreover, it is apparent that Treg, like their $T_H$ cell counterparts, exhibit some level of lineage heterogeneity, as well as the potential for cellular plasticity in response to environmental cues.

Deficiencies in Treg cell frequency and/or function have been associated with the development of autoimmune diseases including systemic lupus erythematosus (SLE), rheumatoid arthritis (RA), Multiple Sclerosis (MS), and type 1 diabetes (T1D). An increase in $IFN\gamma^+$ $Helios^-$ Treg with reduced suppressive capacity was observed in patients with T1D. An analogous finding was also reported in patients with MS. This potential was also observed for the $T_H17$ lineage.

When analyzed at a single-cell level, IL-17-producing $FOXP3^+$ Treg possessed some suppressive capacity, yet exhibited a transient loss of suppression in the presence of inflammatory cytokines. Collectively, these studies raise the intriguing potential that subsets of antigen-experienced Treg with reduced suppressor activity and effector-like properties may contribute to defective immune regulation in the context of persistent inflammation and autoimmune disease.

The ability to preserve and/or bolster the activity of Treg is useful for inhibiting autoimmune reactivity. Studies have generally focused on two subsets of Treg. Thymic-derived natural Treg (nTreg) express the transcription factors FOXP3 and Helios, are demethylated at the FOXP3-Treg Specific Demethylated Region (TSDR), and recognize primarily host antigens. In contrast, peripherally-induced $CD4^+$ $FOXP3^+$ $Helios^-$ Treg (pTreg) develop from naïve T cells under tolerogenic conditions, are partially demethylated at the TSDR, and are generally directed to foreign antigens.

TIGIT has recently been associated with Treg biology through transcriptional profiling of Treg, and has also been identified as a locus epigenetically-marked as being highly demethylated in $FOXP3^-$ T cells. As noted, TIGIT inhibits T cell activation intrinsically through its ITIM motif. Extrinsically, TIGIT ligation to CD155 on DCs leads to a reduction in IL-12 and a concomitant increase in IL-10 production. Importantly, TIGIT attenuates anti-tumor immunity by $CD8^+$ T cells, and was recently demonstrated as a mechanism by which Treg exert their suppressive activity.

Protocols to generate human Treg for adoptive cell therapies are susceptible to contamination by non-Treg, heterogeneity from pTreg subsets, and the potential for lineage instability following extended periods of in vitro culture. Therefore, improved methods for the identification and isolation of Treg are needed.

BRIEF SUMMARY

The subject invention provides regulatory T cells (Treg), methods of identifying and isolating the Treg, and methods of using the Treg for treating and/or preventing diseases including, for example, inflammation-mediated diseases. In a specific embodiment, the inflammation-mediated disease is an autoimmune disease.

According to one embodiment of the invention, the method for isolating a Treg comprises the steps of:
a) analyzing a sample of cells obtained from a subject to determine the level of expression of polypeptides and/or polynucleotides corresponding to proteins CD4, CD25, CD226, and optionally, CD127, and
b) isolating, as the Treg, a cell which:
  i) expresses CD4 and CD25, and
    a) expresses low levels of CD127 or does not express CD127, and/or
    b) expresses low levels of CD226 or does not express CD226.

The invention also provides a Treg isolated from a sample of cells from a subject, wherein the Treg expresses CD4 and CD25, expresses low levels of CD127 or does not express CD127, and expresses low levels of CD226 or does not express CD226. In a further embodiment, the Treg cell does not express CD226 protein.

In one embodiment, the Treg can be proliferated by culturing the Treg in vitro. Accordingly, the invention also provides a cultured Treg obtained by proliferating the Treg isolated from a subject.

The invention further provides pharmaceutical compositions comprising the Treg isolated from a subject, Treg proliferated from the Treg isolated from a subject, or a mixture thereof, and a pharmaceutically acceptable carrier and/or excipient.

Furthermore, the invention provides a method of treating and/or preventing an inflammation-mediated disease in a subject, the method comprising, administering to the subject a therapeutically effective amount of a composition comprising a Treg. In one embodiment, the Treg administered to the subject is autologous Treg, i.e., Treg isolated from the subject and optionally, proliferated by culturing in vitro.

In further embodiments, the subject invention provides materials and methods for driving protective immune responses in the contexts of, for example, cancer treatment and vaccine development. In specific embodiments, the pathways identified according to the subject invention can be either inhibited or augmented to provide therapeutic benefit. This may be achieved using, for example, blocking monoclonal antibodies or through the use of Ig fusion proteins.

BRIEF DESCRIPTION OF THE FIGURES

To obtain a precise understanding of the invention, a more particular description of the invention described herein will be rendered by reference to specific embodiments thereof that are illustrated in the appended Figures. Thus, understanding that these Figures depict only certain embodiments of the invention and are not therefore limiting in scope, the invention will be described and explained with additional specificity and detail through the use of the accompanying Figures.

FIGS. 1A-1C. TIGIT expression is enriched in FOXP3$^+$ Helios$^+$ Tregs. CD4$^+$ T cells were enriched from peripheral blood by negative selection and stained for CD4 and the intracellular transcription factors FOXP3 and Helios. (A) Cells were isolated by FACS to yield Tconv cells (lower left gate), FOPX3$^+$ Helios$^-$ T cells (lower right gate), and FOXP3$^+$ Helios$^+$ Tregs (upper right gate), with representative populations shown. RNA was isolated from sorted populations and subjected to direct transcriptional profiling on the Human Immunology GX Panel on the NanoString platform. (B) TIGIT expression was 12.4-fold higher in FOXP3$^+$ Helios$^+$ Treg compared to Tconv (N=3, p<0.05). (C) Representative TIGIT and Helios expression was shown in gated CD4$^+$FOXP3$^+$ T cells.

FIGS. 4A-4E. Direct ex vivo analysis of TIGIT and CD226 Treg. (A) CD4$^+$CD25$^+$CD127$^-$ T cells were sorted by FACS and further subdivided based on TIGIT and CD226 expression. (B) Freshly sorted Treg subsets were analyzed for FOXP3-TSDR demethylation. (C) Treg subsets and autologous Tconv cells were stained with distinct proliferation dyes and cultured at indicated ratios in the presence of Treg suppression Inspector beads for 4d. Percent suppression was calculated by division index of CD4$^+$ Tconv cells in co-culture relative to Tconv cells alone. (D) The proliferation of each Treg subsets was shown in division index. (E) IL-10 production in suppression assay co-culture supernatants at indicated Treg:Tconv cell ratios.

FIGS. 7A-7K. Exclusion of CD226+ Tregs reduces IFNγ production and augments the in vitro suppressive capacity of Tregs. (A) Total CD4+CD25+CD127$^{lo/-}$ Tregs or CD4+CD127+ Tconv cells were FACS sorted and Tregs were further subdivided into CD226+ and CD226− subsets (right plot). (B) Cells were expanded for 14 d, rested to 21 d, and then reactivated with PMA/ionomycin for 4 h. Treg purity was assessed by FACS for (C, D) FOXP3 and Helios, (E) CD226 expression by gMFI, (F, G) IFNγ and CD226 expression, and (H) TIGIT expression by gMFI. (I) CD226+ and CD226− Treg subsets were assessed for their ability to suppress autologous CD4+ or CD8+ responder T cells from PBMC. (J) The ratio of TIGIT and CD226 expression, as assessed by gMFI on gated Treg populations following the suppression assay (d4). (K) Graph indicates the percent of cells demethylated at the FOXP3-TSDR. Data are represented as ±standard error of the mean (N=4).

FIGS. 8A-8E. IL-12 augments $T_H1$-skewing of CD4+ T cells and attenuates TIGIT expression and proliferation by Tregs. Human PBMCs (2.5×105 cells/well) were activated with anti-CD3 (2 μg/mL) and anti-CD28 (1 μg/mL) in media alone (blue bars) or with the addition of IL-12 (1 ng/mL; red bars). Production of IFNγ was assessed during the final 4 h of culture by addition of monensin prior to harvesting and intracellular cytokine analysis by FACS. (A) Representative plots show TIGIT and CD226 expression on FOXP3+ or FOXP3-CD4+ T cells at 24, 48, and 72 h of culture. Data are summarized as (B) gMFI of TIGIT on CD4+FOXP3+Helios+ and CD4+FOXP3+ Helios− cells, (C) CD226 gMFI on CD4+ T cells, (D) percent CD4+IFNγ+ cells, and (E) frequency of TIGIT expression on FOXP3+ Helios+ Tregs. Shown is the standard error of the mean (N=6).

FIGS. 18A-18C. Analysis of T cells from human spleen, pDLN, and islets in T1D. (A) A single cell suspension of lymphocytes was prepared from spleen and LN material and subjected to intracellular staining for Helios and FOXP3. Shown are representative plots from indicated tissues. Immunohistochemisty images depict insulin staining and T cell infiltration in pancreatic islets from a 1 yr old T1D (B and C).

FIG. 19. Isolation of live viable human B cells, CD8+ T cells, CD4+ Treg and Tconv cell subsets. pDLN from a T1D donor (1 yr duration, insulitis and triple auto-Ab+). Single cell suspensions were surface stained and FACS sorted with cell yields indicated.

BRIEF DESCRIPTION OF SEQUENCES

Figures 2A, 2B:
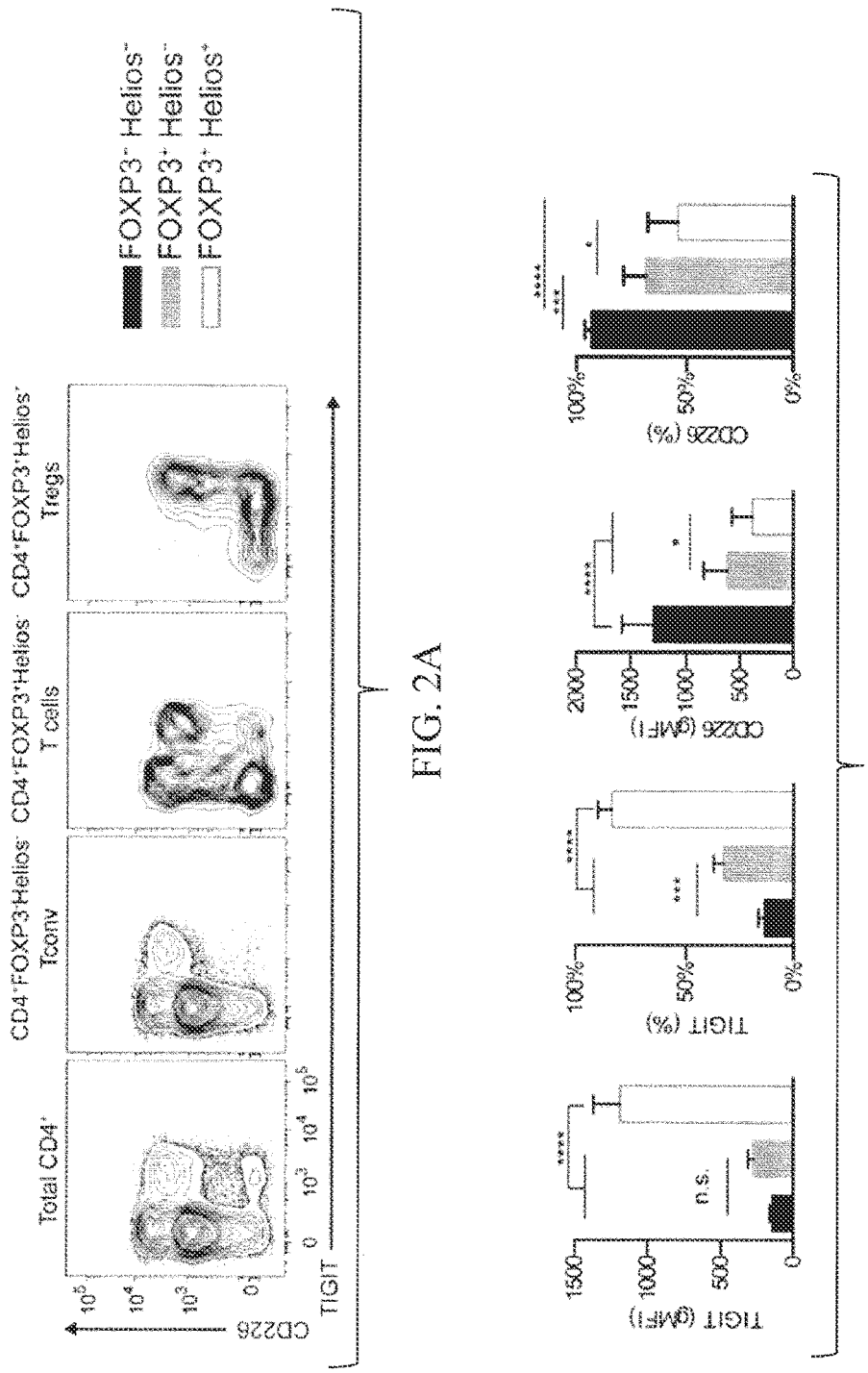
FIGS. 2A-2B. Differential expression of CD226 and TIGIT on CD4$^+$ T cell subsets. PBMCs were stained for CD4, CD226, TIGIT and the transcription factors FOXP3 and Helios. (A) Representative plots show TIGIT and CD226 on total CD4$^+$ T cells, Tconv, FOPX3$^+$ Helios$^-$, and FOXP3$^-$ Helios$^+$ Treg populations. (B) Graphs show summarized data demonstrating TIGIT is enriched in Treg populations (left graphs) analyzed by geometric Mean Fluorescence Intensity (gMFI) and percent positive, whereas CD226 is enriched in Tconv cells (right graphs). Shown are mean±standard error with significance indicated (N=5; n.s., not significant; *, p<0.05; , p<0.01; *, p<0.001; ****, p<0.0001).

SEQ ID NO: 1: Selected amplicon for real-time PCR assay for TSDR fragment of foxp3 gene.

GGTCTGCATCTGGGCCCTGTTGTCACAGCCCCCGACTTGCCCAGATTTTT

CCGCCATTGACGTCATGGCGGCCGGATGCGCCGGGCTTCATCGACACCAC

GGAGGAAGAGAAGAGGGCAGATACCCCACCCCACAG

SEQ ID NO: 2: FOXP3_TSDRfwd primer for the standard curve (ATATTTTTAGATAGGGATATGGAGATGATTTGTTTGG)

SEQ ID NO: 3: FOXP3_TSDRrev primer for the standard curve (AATAAACATCACCTACCACATCCACCAACAC).

SEQ ID NO: 4: The probe used for PCR amplification, TSDR-Forward

GGTTTGTATTTGGGTTTTGTTGTTATAGT

SEQ ID NO: 5: The probe used for PCR amplification TSDR-Reverse

CTATAAAATAAAATATCTACCCTCTTCTCTTCCT

SEQ ID NO: 6: Sequence of the probe for methylated target sequence detection.

CGGTCGGATGCGTC

SEQ ID NO: 7: Sequence for the probe for unmethylated target sequence detection.

TGGTGGTTGGATGTGTTG

DETAILED DESCRIPTION

In one embodiment, the subject invention provides regulatory T cells (Treg), methods of identifying and isolating the Treg, and methods of using the Treg for treating and/or preventing diseases including, for example, inflammation-mediated diseases. In a specific embodiment, the inflammation-mediated disease is an autoimmune disease.

In specific embodiments, the subject invention provides markers to delineate functionally distinct Treg subsets that help direct cellular therapies and provide important phenotypic markers for assessing the role of Treg in health and disease.

According to one embodiment of the invention, the method for isolating a Treg comprises the steps of:
 a) analyzing a sample of cells obtained from a subject to determine the level of expression of CD4, CD25, CD226, and optionally, CD127, and
 b) isolating, as the Treg, a cell which:
  i) expresses CD4 and CD25,
   a) expresses low levels of CD127 or does not express CD127, and/or
   b) expresses low levels of CD226 or does not express CD226.

In one embodiment of the invention, the level of expression of CD127, CD4, CD25, and CD226 is analyzed at the mRNA level. For example, oligonucleotides corresponding to the target mRNAs can be labeled and the sample of cells can be contacted with the labeled oligonucleotides. Oligonucleotides corresponding to different mRNAs can be labeled differently to facilitate identification of the presence of the target mRNAs within a cell.

In another embodiment of the invention, the level of expression of CD127, CD4, CD25, and CD226 is analyzed at the protein level. For example, the analysis of the expression of CD127, CD4, CD25, and CD226 proteins can be performed using flow cytometry using labeled antibodies specific for CD127, CD4, CD25, and CD226. Various techniques for labeling, identification, and isolation of cells by flow cytometry are well known to a person of ordinary skill in the art and such embodiments are within the purview of the invention.

The invention also provides a Treg isolated from a sample of cells from a subject, wherein the Treg expresses CD4 and CD25, expresses low levels of CD127 or does not express CD127, and expresses low levels of CD226 or does not express CD226. In a further embodiment, the Treg cell does not express CD226 protein.

In a further embodiment, Treg expresses CD4 and CD25, and expresses low levels of CD226 or does not express CD226. In certain embodiments, Treg cell is $CD4^+CD25^+CD226^-$. In one embodiment, the Treg can be proliferated by culturing the Treg in vitro. Accordingly, the invention also provides a cultured Treg obtained from proliferating the Treg isolated from a subject.

The invention further provides pharmaceutical compositions comprising the Treg isolated from a subject, Treg proliferated from the Treg isolated from a subject, or a mixture thereof, and a pharmaceutically acceptable carrier and/or excipient.

Furthermore, the invention provides a method of treating and/or preventing an inflammation-mediated disease in a subject, the method comprising, administering to the subject a therapeutically effective amount of a composition comprising a Treg. In one embodiment, the Treg administered to the subject is autologous Treg, i.e., Treg isolated from the subject and optionally, proliferated by culturing in vitro.

In one embodiment of the subject invention, immune responses associated with CD226 are enhanced in order to elicit an immune response useful for the treatment of cancer and/or to generate a protective immune response against a pathogen.

Definitions

As used herein the term "Treg" refers to regulatory T cells, either singular or plural.

As used herein, the terms "express," "expresses," or "expressing" at low levels (indicated by "$^{lo}$"), or any other synonymous terms, refer to a level of expression of a polypeptide or polynucleotide, such as CD127, CD4 or CD25, by a cell within a sample that is lower when compared to the level of expression of that polypeptide or polynucleotide by the population of cells comprising the whole of the sample being analyzed. For example, the term "CD127$^{lo}$" refers to a level of expression of CD127 by a particular cell within the sample that is lower compared to the level of expression of CD127 by the population of cells comprising the whole of the sample being analyzed.

Similarly, the terms "express," "expresses," or "expressing" (indicated by "+"), or any other synonymous terms, refer to a level of expression of a polypeptide or polynucleotide, such as CD127, CD4 or CD25, by a cell within a sample that is higher compared to the level of expression of that molecule or polynucleotide by the population of cells comprising the whole of the sample being analyzed. For example, the term "CD4$^+$" refers to a level of expression of CD4 by a particular cell within the sample that is higher compared to the level of expression of CD4 by the population of cells comprising the whole of the sample being analyzed. More particularly, the term "+" may refer to a distinct cell that expresses a particular molecule at a level that is higher than that expressed by one or more other distinct populations within a sample.

Further, the terms "express," "expresses," or "expressing" at high levels (indicated by "hi"), or any other synonymous terms, refer to a level of expression of a particular polypeptide or polynucleotide, such as CD127, CD4 or CD25, by a particular cell within a sample that is substantially higher (for example, by more than 2 fold, 10 fold, 100 fold, 1000 fold or more) compared to the level of expression of that molecule or polynucleotide by the population of cells comprising the whole of the sample being analyzed. For example, in one embodiment the term "CD25$^{hi}$" refers to a level of expression of CD25 by a particular cell within the sample that is about 10 times higher when compared to the level of expression of CD25 by the population of cells comprising the whole of the sample being analyzed.

Also as used herein, the terms "do not express," "does not express," or "not expressing" (indicated by "−"), or any other synonymous terms, refer to a level of expression of a particular polypeptide or polynucleotide, such as CD127, CD4 or CD25, by a cell within a sample that cannot be detected by the standard molecular technique used to analyze the particular molecule. Therefore, a cell identified as "not expressing" a polypeptide or polynucleotide may be expressing some level of the polypeptide or polynucleotide; however, the level of expression is too low to be detected by the technique used. For example, the term "CD127$^−$" refers to a level of expression of CD127 protein by a particular cell within the sample which cannot be detected by the standard molecular biology technique used to detect CD127 protein expression.

Treg Subsets

To better elucidate human Treg subsets, a direct transcriptional profiling of CD4$^+$FOXP3$^+$ Helios$^+$ natural Treg (nTreg) and CD4$^+$FOXP3$^+$ Helios$^-$ peripheral Treg (pTreg) was conducted and was compared to CD4$^+$FOXP3$^-$ Helios$^-$ T cells, followed by comparison to CD4$^+$FOXP3$^-$ Helios$^-$ T conventional (Tconv) cells. This analysis revealed the coinhibitory receptor T-cell immunoglobulin and immunoreceptor tyrosine-based inhibitory motif domain (TIGIT) to be highly expressed on nTreg. Given that TIGIT competes with the costimulatory factor CD226 for binding to CD155, the cellular distribution and suppressive activity of isolated subsets of CD4$^+$CD25$^+$CD127$^{lo/-}$ T cells expressing CD226 and/or TIGIT were analyzed. TIGIT expression on Treg is upregulated following activation and in vitro expansion, and correlates with lineage stability and suppressive capacity. Conversely, the CD226$^+$ TIGIT$^-$ population was associated with reduced Treg purity and suppressive capacity following expansion, along with a marked increase in IL-10 and effector cytokine production.

The subject invention provides isolated subsets of human CD4$^+$CD25$^+$CD127$^{-/lo}$ Treg. These subsets were proliferated ex vivo to assess their phenotype and suppressive capacity. Production of the effector cytokine IFNγ within Tconv cells and the CD4$^+$CD25$^+$CD127$^{-/lo}$ Treg pool was found to be tightly linked to co-expression of the costimulatory molecule CD226. Conversely, selection of CD226$^-$ Treg, irrespective of initial TIGIT expression, leads to a highly enriched population of nTreg that are demethylated at the TSDR, express TIGIT and suppress T proliferation.

Methods for Isolating Treg

In one embodiment, the invention provides a method of isolating Treg, wherein the step of analyzing the level of expression of CD4, CD25, CD226, and optionally, CD127, proteins comprises:
  (a) obtaining a sample of cells from a subject;
  (b) contacting the cells with antibodies directed towards CD4, CD25, CD226, and optionally, CD127 proteins to allow binding of the antibodies to the corresponding proteins;
  (c) subjecting the sample of cells to flow cytometry;
  (d) examining the flow cytometry signal for the expression of CD4, CD25, CD226, and optionally, CD127 proteins; and
  (e) isolating, as the Treg, a cell which:
    i) expresses CD4 and CD25,
      a) expresses low levels of CD127 or does not express CD127, and/or
      b) expresses low levels of CD226 or does not express CD226.

The analysis of the expression of CD127, CD4, CD25, and CD226 proteins can be performed simultaneously or sequentially.

For example, when the analysis of CD127, CD4, CD25, and CD226 proteins is performed sequentially, a sample of cells can be contacted with labeled antibodies against CD127, CD4, CD25, and CD226 proteins followed by the steps of:
  i) identifying and isolating CD4 expressing cells,
  ii) identifying and isolating CD25 expressing cells within the CD4 expressing cells,
  iii) identifying and isolating cells expressing low levels of CD127 and/or not expressing CD127 within the cells expressing both CD25 and CD4, and
  iv) identifying and isolating cells expressing low levels of CD226 and/or not expressing CD226 within the cells expressing CD24 and CD25 and expressing low levels of CD127 and/or not expressing CD127.

In a further example, when the analysis of CD4, CD25, and CD226 proteins is performed sequentially, a sample of cells can be contacted with labeled antibodies against CD4, CD25, and CD226 proteins followed by the steps of:

i) identifying and isolating CD4 expressing cells,
ii) identifying and isolating CD25 expressing cells within the CD4 expressing cells,
iii) identifying and isolating cells expressing low levels of CD226 and/or not expressing CD226 within the cells expressing CD24 and CD25.

A person of ordinary skill in the art can envision and design alternative methods of sequential separation of cells to obtain the Treg according to the claimed invention and such embodiments are within the purview of the invention.

Similarly, when the analysis of CD127, CD4, CD25, and CD226 proteins is performed simultaneously, a sample of cells can be contacted with labeled antibodies against CD127, CD4, CD25, and CD226 proteins followed by the steps of:
i) identifying and isolating the cells expressing both CD4 and CD25, and
ii) identifying and isolating the cells expressing low levels of CD226 and/or not expressing CD226 and expressing low levels of CD127 and/or not expressing CD127 within the cells expressing both CD24 and CD25.

Also, when the analysis of CD4, CD25, and CD226 proteins is performed simultaneously, a sample of cells can be contacted with labeled antibodies against CD4, CD25, and CD226 proteins followed by the steps of:
i) identifying and isolating the cells expressing both CD4 and CD25, and
ii) identifying and isolating the cells expressing low levels of CD226 and/or not expressing CD226 within the cells expressing both CD24 and CD25.

A person of ordinary skill in the art can envision and design alternative methods of simultaneous separation of cells to obtain the Treg according to the claimed invention and such embodiments are within the purview of the invention.

A person of ordinary skill in the art can determine the sequence of a particular protein or polynucleotide corresponding to a protein of interest (e.g., CD4, CD25, CD127, and CD226) and corresponding antibodies or other techniques required to isolate Treg according the methods of the invention.

The subject from which the Treg can be obtained according to the methods of the invention can be a mammal. Non-limiting examples of mammals include mice, rats, cats, dogs, bovine, porcine, non-human primates and humans.

The sample of cells can be obtained from a biological sample from the subject. The biological sample may be, for example, bodily fluids or tissue. Non-limiting examples of bodily fluids include whole blood, isolated peripheral blood mononuclear cells (PBMC) or leukopharesis products, urine, saliva, buccal mucosa, interstitial fluid, and lymph fluid. The bodily fluid can be appropriately treated before it is used pursuant to the methods of the invention.

Tissues from which Treg can be obtained according to the methods of the invention include, but are not limited to, tonsil, thymus, spleen, lymph node or a non-lymphoid tissue. Tissues can also be appropriately treated to obtain a sample of cells from the subject before implementing the methods of the invention.

Isolated Treg

The invention also provides a Treg isolated from a sample of cells obtained from a subject, wherein the Treg, at the protein or mRNA level, expresses CD4 and CD25, expresses low levels of CD127 or does not express CD127, and expresses low levels of CD226 or does not express CD226.

In one embodiment, the Treg expresses CD4 and CD25 proteins, expresses low levels of CD127 protein or does not express CD127 protein, and expresses low levels of CD226 protein or does not express CD226 protein. In a further embodiment, the Treg cell does not express CD226 protein. In a further embodiment, the Treg expresses high levels of CD4 and CD25 proteins, does not express CD127 or expresses low levels of CD127 and does not express CD226. In an even further embodiment, the Treg expresses high levels of CD4 and CD25 proteins, does not express CD226 or expresses low levels of CD226.

The Treg can be proliferated by culturing the Treg in vitro. Accordingly, the invention also provides Treg obtained by proliferating the Treg isolated from a subject. Methods of proliferating Treg obtained from a subject in culture are well known to a person of ordinary skill in the art.

For the purposes of the invention, the term "proliferate" or any of the relevant terms or synonyms thereof (e.g. proliferating, proliferated, multiplied, amplified, etc.) refer to culturing the Treg under appropriate conditions that allows for an increase in the number of Treg.

Pharmaceutical Compositions

The invention further provides pharmaceutical compositions comprising Treg isolated from a subject; Treg proliferated from Treg isolated from a subject; or a mixture thereof and a pharmaceutically acceptable carrier and/or excipient.

Pharmaceutical compositions, as disclosed herein, can be formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art. Pharmaceutical composition according to the invention may also be formulated to release active agents (e.g., Treg as disclosed herein alone or in combination with a chemotherapeutic agent) substantially immediately upon administration or at any predetermined time or time period after administration.

Compositions for parenteral administration are generally physiologically compatible sterile solutions or suspensions that can optionally be prepared immediately before use from solid or lyophilized form. Adjuvants, local anesthetics, preservatives and/or buffering agents can be added to the vehicle and a surfactant or wetting agent can be included in the composition to facilitate uniform distribution of the active ingredient.

The composition can be formulated into conventional dosage forms, such as liquid preparations, syrups, and concentrated drops. Non-toxic solid carriers or diluents may be used, which include, for example, pharmaceutical grades of mannitol, lactose, starch, magnesium stearate, sodium saccharine, talcum, cellulose, glucose, sucrose, magnesium, carbonate.

The pharmaceutical composition of the invention may be in a variety of forms. These include, for example, solid, semi-solid, and liquid dosage forms, such as lyophilized preparations, liquids solutions or suspensions, injectable and infusible solutions, etc. The preferred form depends on the intended mode of administration and therapeutic application.

Administration of Treg

The Treg can be administered to a subject via conventional means. For example, Treg can be transferred to the desired tissue, either in vitro (e.g., as a graft prior to implantation or engrafting) or in vivo, to the subject's tissue directly.

Treg can be transferred to the desired tissue by any appropriate method depending on the tissue type. In the case of a graft tissue, Treg can be transferred to the graft by bathing the graft (or infusing it) with culture medium containing the cells or the Treg can be seeded onto the desired site within the tissue to establish a population. Devices such as catheters, trocars, cannulae, and stents seeded with the Treg can be used as appropriate.

In further embodiments, the composition of the invention can be administered to the subject via local or systemic route. Non-limiting examples of the systemic route include intravenous, intraperitoneal, intramuscular or subcutaneous. Additional methods and routes of administering pharmaceutical compositions of the claimed invention to a subject in need thereof are well known to a person of ordinary skill in the art and such embodiments are within the purview of the claimed invention.

Therapeutical Treatments

Furthermore, the invention provides a method of treating and/or preventing an inflammation-mediated disease in a subject, wherein the method comprises, administering to the subject a therapeutically effective amount of the pharmaceutical compositions comprising Treg and a pharmaceutically acceptable carrier and/or excipient.

The subject that can be treated according the methods of the invention can be a mammal. Non-limiting examples of mammals treatable according to the methods of the invention include a mouse, a rat, a cat, a dog, a bovine, a porcine, a non-human primate or a human.

For the purposes of this invention the term "inflammation-mediate disease" refers to a disease characterized by a dysregulation of the normal immune response. Inflammation mediated diseases can cause organ damage, and are associated with increased morbidity and/or mortality. An example of immune dysregulation is the inappropriate activation of inflammatory cytokines, such as IL-12, IL-6 or TNF alpha, whose actions lead to pathological consequences.

For the purposes of this invention the terms "treatment, treating, treat" or equivalents of these terms refer to curing, healing, alleviating, relieving, altering, remedying, ameliorating, or improving the condition or the symptoms of a subject suffering with a disease, for example, type 1 diabetes. Total absence of the disease symptoms is not required for "treating" a disease. The subject to be treated can be suffering from or at risk of developing the disorder, for example, type 1 diabetes.

For the purposes of this invention, the terms "preventing, preventive, prophylactic" or equivalents of these terms are indicate that the Treg is provided in advance of disease symptoms. The prophylactic administration of the Treg serves to prevent or attenuate any subsequent symptoms or disease. Total avoidance of disease symptoms is not required for "preventing" the disease.

By "therapeutically effective dose," "therapeutically effective amount", or "effective amount" is intended to be an amount of the Treg that, when administered to a subject, decreases the inflammatory response, or prevents an inflammatory response from increasing. "Positive therapeutic response" refers to, for example, improving the condition of at least one of the symptoms of an inflammatory disorder.

In one embodiment, the Treg administered to the subject is an autologous Treg, i.e., Treg isolated from the subject and optionally, proliferated in vitro.

If the Treg administered to a subject is an autologous Treg, the method of treating and/or preventing an inflammation mediated disease in the subject can comprise the steps of:

a) isolating a Treg from a sample of cells obtained from the subject, wherein the Treg expresses CD4 and CD25, expresses low levels of CD127 or does not express CD127, and expresses low levels of CD226 or does not express CD226, b) optionally, proliferating the Treg isolated from the subject in vitro, and c) administering to the subject, the Treg obtained from the subject or the Treg proliferated from the Treg obtained from the subject.

In one embodiment, the Treg administered to a subject is an autologous Treg, and the method of treating and/or preventing an inflammation mediated disease in the subject comprises the steps of:

a) isolating a Treg from a sample of cells obtained from the subject, wherein the Treg expresses CD4 and CD25, expresses low levels of CD226 or does not express CD226, b) optionally, proliferating the Treg isolated from the subject in vitro, and c) administering to the subject, the Treg obtained from the subject or the Treg proliferated from the Treg obtained from the subject.

Treg can be administered in a manner compatible with the dosage formulation, and in such amount as will be therapeutically effective. The quantity of Treg to be administered depends on the subject to be treated. The dose and route of administration will vary according to, for example, the type and weight of the subject, severity of the disease, etc. Precise number of cells administered to a subject depends on the judgment of the practitioner. However, suitable dosage ranges are of the order of a few thousand cells to millions of cells. Suitable regimes for initial administration and subsequent administrations are also variable. Typically, an initial administration can be followed by subsequent administrations.

Various autoimmune diseases that can be treated according to the compositions and methods of the current invention include, but are not limited to, acute disseminated encephalomyelitis (ADEM), Addison's disease, alopecia areata, amyloidosis, autoimmune retinopathy, autoimmune thyroid disease, axonal & neuronal neuropathies, chronic fatigue syndrome, chronic inflammatory demyelinating polyneuropathy (CIDP), Crohn's disease, Coxsackie myocarditis, dermatitis herpetiformis, experimental allergic encephalomyelitis, Evans syndrome, fibromyalgia, glomerulonephritis, granulomatosis with polyangiitis (GPA) (formerly called Wegener's Granulomatosis), Graves' disease, Guillain-Barre syndrome, Hashimoto's encephalitis, Hashimoto's thyroiditis, Hemolytic anemia, Kawasaki syndrome, Lupus (SLE), Lyme disease, Meniere's disease, multiple sclerosis, myasthenia gravis, myositis, neuromyelitis optica (Devic's), neutropenia, scleroderma, Sjogren's syndrome, stiff person syndrome.

Further embodiments of the invention provide uses of antagonists or agonists against CD226 or TIGIT for the treatment of cancer or an autoimmune disorder.

The antagonists or agonists of CD226 or TIGIT can be a small molecule compound or can be a biologic such as an antibody or fragment thereof. A person of ordinary skill in the art, having the benefit of the current disclosure, can obtain a small molecule antagonists or agonists of CD226 or TIGIT by, for example, screening small molecule compound libraries using assays routine in the art.

The antagonists or agonists of CD226 or TIGIT can also be a biologic such as, for example, an antibody, aptamer, fusion protean or other biomolecule capable of specifically binding to CD226 or TIGIT.

For the purposes of this invention, the binding between two molecules, which is based on specific interactions between sites present on the two molecules, is referred to as "specific binding". The specific binding between two entities can be represented by, for example, their dissociation constant, which, according to the current invention can be, for example, less than about $10^{-6}$, less than about $10^{-7}$, or less than about $10^{-8}$ M. Examples of specific binding include, but are not limited to, binding between an antibody and a binding partner based on interactions between the binding sites present on the antibody and specific epitopes present on the binding partner, binding between an aptamer and its target biomolecule based on the interactions between the target binding sites present on the aptamer and the specific target sites present on the target biomolecule. Additional examples of specific binding between any two molecules and further aspects of specific binding are well known to a person of ordinary skill in the art.

Antibodies can be polyclonal antibodies, monoclonal antibodies, recombinant antibodies or hybrid antibodies. Non-limiting examples of recombinant or hybrid antibodies include chimeric antibodies, humanized monoclonal antibodies, single chain antibodies, single chain fragment variable (scFv) antibodies, and antigen-binding fragments (Fab fragment).

Fusion proteins capable of binding to CD226 or TIGIT can comprise, for example, a portion that specifically binds to CD226 or TIGIT fused to another portion. In one embodiment, a fusion protein comprises an antigen binding fragment of an antibody that specifically binds to CD226 or TIGIT and Fc portion of IgG.

In specific embodiments, biomolecules that specifically bind to CD226 or TIGIT are administered to a patient. Non-limiting examples of such biomolecules include antibodies, fragments of antibodies, aptamers, or fusion proteins. For example, a method of treating a disease, for example, cancer or an autoimmune disease, comprises administering polyclonal antibodies, monoclonal antibodies, recombinant antibodies or hybrid antibodies against CD226 or TIGIT. A method of treating a disease can also comprise administering to a patient in need thereof, a recombinant or hybrid antibody, for example, chimeric antibodies, humanized monoclonal antibodies, a single chain antibody, a single chain fragment variable (scFv) antibody, or a fragment antigen-binding (Fab fragment) capable of binding CD226 or TIGIT.

A further embodiment provides a method of treating a disease comprising administering to a patient in need thereof, fusion proteins capable of binding to CD226 or TIGIT for example, a fusion protein comprising an antigen binding fragment of an antibody which specifically binds to CD226 or TIGIT and Fc portion of IgG.

Materials and Methods

Sample Procurement and Processing

Peripheral blood was collected from healthy control donors (median age 28.8, range 22.5-46.7) or purchased from Life South Blood Centers (median age 23, range 20-26). Venous blood was collected in sodium-heparinized vacutainer tubes (BD Biosciences) or supplied in sodium citrate followed by PBMC isolation by density gradient centrifugation. For FACS experiments, whole blood was pre-enriched by negative selection with RosetteSep (Stemcell) prior to centrifugation.

Transcription Factor Sorting and Expression Analysis $CD4^+$ RosetteSep enriched T cells were stained with anti-CD4, fixed and permeabilized with the FOXP3 Fix/Perm (Biolegend) per manufacturer recommendations and stained for FOXP3 and Helios. tTreg ($CD4^+FOXP3^+$ $Helios^+$), $CD4^+FOXP3^+$ $Helios^-$ T cells and Tconv ($CD4^+$ $FOXP3^-$ $Helios^-$) were sorted into RNALater (Life Technologies). RNA was extracted with the RNeasy FFPE Kit (Qiagen) by proteinase K digestion followed by incubation at 80° C. RNA quality was verified on a Bioanalyzer (>300 bp length for over 50% of transcripts) with the RNA Nano Chip (Agilent Technologies). RNA transcripts (100 ng) were directly quantified with the nCountero and the Human Immunology GX Panel (NanoString Technologies, v1).

Flow Cytometry and FACS

All samples were first stained with Fixable Live/Dead Yellow or Near IR (Invitrogen), and then stained for surface markers in stain buffer for 30 min at 4° C. (PBS+2% FBS+0.05% $NaN_3$). For flow panels with only surface markers, cells were fixed with BD Cytofix™—Fixation buffer (BD Bioscience) according to the manufacture's protocol. For intracellular staining, cells were fixed and permeabilized with the FOXP3 Fix/Perm buffer then stained for intracellular proteins in FOXP3 Perm buffer (BioLegend) according to manufacture's protocol. The antibodies used included CD4-Pacific Blue (RPA-T4), TIGIT-APC or -PerCP-eFluor710 (MBSA43), (eBioscience), CD226-PE (11A8) and CD8 (SK1), (BD Bioscience), CD25-APC or—AlexaFluor (AF)-488 (BC96) (BioLegend), IFN-γ-PE-Cy7 (4S.B3), Helios-PE or -Pacific Blue, -AF647 (22F6) (BioLegend), FOXP3-AF488 and -PE (206D) (BioLegend).

Flow cytometric analyses were performed on a LSR Fortessa (BD Bioscience). Data was collected using BD DIVA acquisition software as FCSv.3 files and imported into FlowJo V 9.7.5 (TreeStar Inc) for analysis. Cell proliferation data was determined by calculating the division index (DI) of responding populations gated as live with viability dye and lymphocyte gating. Percent marker positivity was determined by fluorescence minus one (FMO) method. Expression levels were calculated with geometric mean fluorescence (gMFI) intensity.

All cell sorting was conducted on a FACS Aria III (BD Bioscience) cell sorter. Treg ($CD4^+CD25^+CD127^-$) and TConv ($CD4^+CD127^+$) were further enriched based on CD226 and/or TIGIT expression. Post-sort purities were typically greater than 93% (median 93%; range 90%-95%).

In Vitro T Cell Expansions and Activation Cultures

Treg and Tconv cells were expanded as previously described by Putnam et al. (2009). After expansion, cells were analyzed for intracellular IFNγ by re-activation for 4 h with PMA (10 µg/mL) and Ionomycin (500 nM) in the presence of GolgiStop (4 µl/6 mL culture; BD Biosciences). For multiplex cytokine detection, cells were activated with anti-CD3 and anti-CD28 coated dynabeads (Life Technologies) according to manufacturer recommendations and supernatants collected at 24, 48, and 72 h.

In Vitro Suppression Assays

Expanded Treg subsets were tested for their ability to suppress autologous T cell proliferation, as described by Brusko et al. (2007), with the following modifications. Treg were labeled with CFSE (0.15 µM), while responding cells were stained with Cell Trace Violet (2.5 µM, Life Technologies) and activated with either autologous APCs or Treg Suppression Inspector beads (Miltenyi Biotec). Triplicate cultures were harvested and pooled following 96 h, stained with live/dead dye, CD4, CD8, CD226 and TIGIT, and proliferation was calculated by division index (DI) of gated live lymphocytes.

Analysis of the FOXP3-TSDR

Figure 22A:
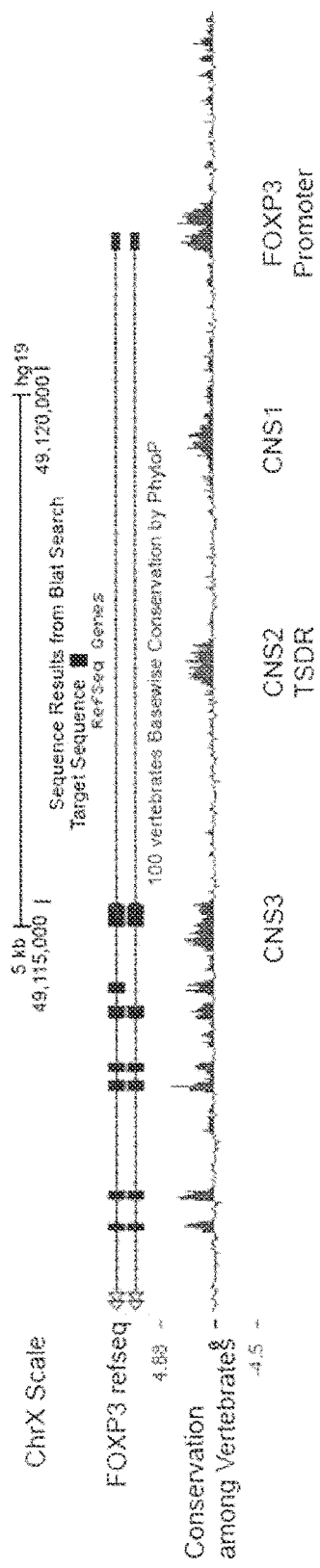
FIGS. 22A-22C. Determination of the methylation status of the FOXP3—Treg Specific Demethylated Region (TSDR). (A) A schematic view of the genomic exon-intron structure of the foxp3 gene and TSDR position (CNS2). The enlarged TSDR fragment depicts the distribution and position of individual CpG motifs contained within the TSDR and the selected amplicon for real-time PCR assay (indicated by the black marked target region) covering the sequence: 5'-GGTCTGCATCTGGGCCCTGTTGT-CACAGCCCCCGACTTGCCCAGATTTTTCCGCCAT-TGAC GTCATGGCGGCCGGATGCGCCGGGCTT-CATCGACACCACGGAGGAAGAGAAGAGGGCA GATACCCCACCCCACAG-3' (SEQ ID NO: 1). (B) Graphical illustration of the FOXP3-TSDR methylation-specific real-time PCR assay. Sample DNA is bisulfite-converted and the target sequence is amplified. FAM and VIC dye-labeled internal MGB Taqman® probes are designed for binding specifically to either the unmethylated (VIC) or methylated (FAM) allele sequence, respectively. Ratios of methylated and unmethylated standards were serial titrated to generate a standard curve. (C) The difference of Ct values (Ct unmethylated probe−Ct methylated probe) is plotted against the standards to extrapolate the percent of cells demethylated at the TSDR.

TSDR demethylation is a hallmark of lineage-stable nTreg. This region coincides with the conserved non-coding sequence 2 (CNS2) within the first intron of the foxp3 gene (FIG. 22A). When DNA and RNA were required from the same samples, cells were processed with the AllPrep DNA/RNA Mini Kit (Qiagen). Otherwise, genomic DNA was isolated from purified T cell subsets using the DNeasy tissue kit (Qiagen). Bisulfite treatment of genomic DNA was performed with the EZ DNA Methylation Kit (Zymo Research). Briefly, 500 ng genomic DNA was sodium bisulfite treated overnight at 50° C., followed by 10 min on ice. After washing and desulphonation, bisulfite converted DNA was eluted with 16 µl elution buffer.

To create a standard curve, fully methylated or unmethylated bisulfite-treated DNA was titrated at varying ratios. DNA was comprised of unmethylated bisulfite-converted human EpiTect control DNA (Qiagen) and universally methylated bisulfite-converted human control DNA (Zymo Research). The TSDR was PCR amplified using the following reaction: 50 µL reaction volume containing 25 µL of ZymoTaq™ PreMix buffer (Zymo Research) and 0.5 µM each of the primers FOXP3_TSDRfwd (ATATTTTTAGA-TAGGGATATGGAGATGATTTGTTTGG) (SEQ ID NO: 2) and FOXP3_TSDRrev (AATAAACATCACCTACCA-CATCCACCAACAC) (SEQ ID NO: 3). After incubation at 95° C. for 10 min, amplification was performed as follows: 50 cycles at 95° C. for 30 sec, 55° C. for 30 sec, and 72° C. for 1 min. Amplified PCR products were purified with the QIAquick Gel Extraction Kit (Qiagen). The concentration of purified DNA was determined with a GE NanoVue spectrophotometer (GE Healthcare Life Sciences).

Figure 22B:
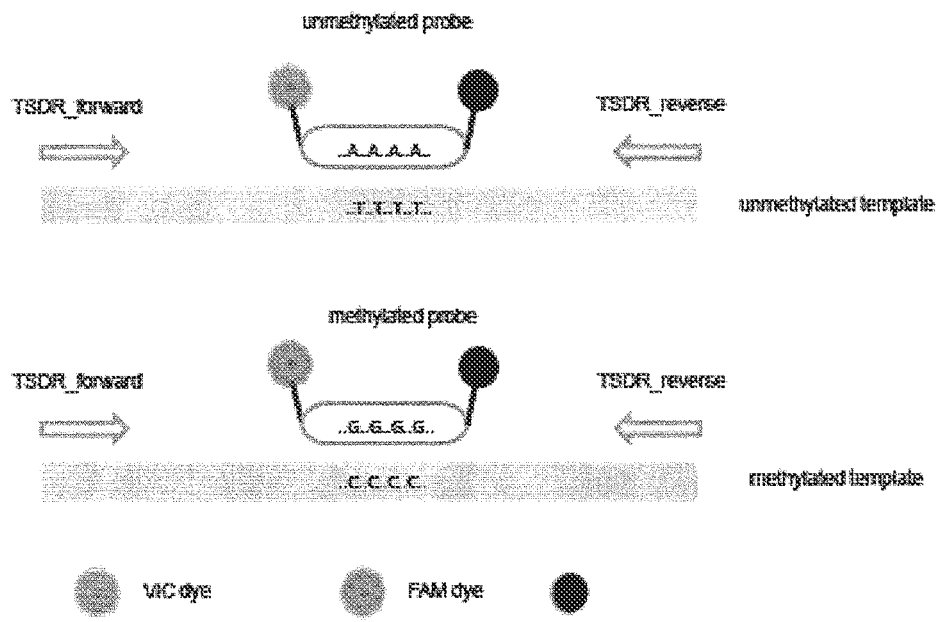
Figure 22C:
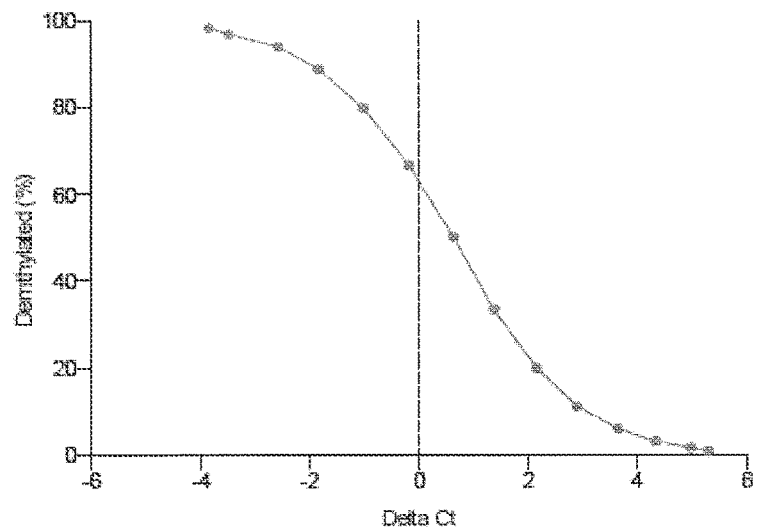

TSDR real-time PCR was performed in 384-well white trays with a Roche LightCycler 480 system (Roche Diagnostics) with real-time probes that target methylated or demethylated target sequences (FIG. 22). Each reaction contained 10 µL Lightcycler 480 Probes Master Mix (Roche), 1 µL bisulfite converted DNA sample or standards, 1 µM of each primer and 150 nM of each probe with a final reaction value of 20 µl. The probes used for amplification were TSDR-Forward GGTTTGTATTTGGGTTTTGTTGT-TATAGT (SEQ ID NO: 4) and TSDR-Reverse CTATAAAATAAAATATCTACCCTCTTCTCTTCCT (SEQ ID NO: 5). The probes for target sequence detection were FAM-labeled methylated probe, FAM-CGGTCG-GATGCGTC-MGB-NFQ (SEQ ID NO: 6), or VIC-labeled unmethylated probe, VIC-TGGTGGTTGGATGTGTTG-MGB-NFQ (SEQ ID NO: 7). All samples were tested in triplicate. The protocol for real-time amplification is as follows: after initial denaturation at 95° C. for 10 min, the samples were subjected to 50 cycles at 95° C. for 15 sec and at 61° C. for 1 min. 14 different ratios of fully methylated and demethylated template were used as real-time standards (FIG. 22C). The 6-order polynomial equation was used to extrapolate the percentage of cells demethylated at the TSDR for each sample.

T Cell Transcriptional Profiling

Using the nSolver Analysis Software (NanoString, Inc.), counts were first normalized to the geometric mean of the positive control spiked into the assay, then normalized to housekeeping genes built into the Human Immunology panel. Subsequent analyses were conducted with the Partek Genomic Suite (Partek Inc.). The signal-to-noise ratio was significantly higher in the expanded T cell counts compared to the fixed cell sorted T cell counts. Thus, two different statistical approaches were used.

For the count data from fixed cells, the average of the negative controls were subtracted from the counts and values less than 1 were converted to 1 prior to subsequent analysis. A paired ANOVA coupled with the Bonferroni multiple test correction (MTC) was used to determine differentially regulated genes with a significance value of $p<0.05$. Genes were classified into T cell subsets and validated with the leave-one-out cross validation method using 100 permutations and a $p<0.01$ considered significant.

When analyzing gene expression profiles from unfixed expanded cell subsets, genes that were below the background threshold (mean of negative controls count+2 standard deviations) for both Treg and Tconv were removed from the analysis. Because Tconv often have a variance different than Treg at both the RNA and proteins levels, A Welch's ANOVA with a Bonferroni MTC was used to determine significance ($p<0.05$). Significantly regulated genes with a false discovery rate below 0.05 were normalized around zero and clustered using the average of the means.

Isolation of IFNγ Producing Treg

Treg and Tconv were FACS isolated from five healthy subjects (median age 26, range 22-30) and sorted into two groups. Briefly, the first group was stimulated for 4 hours with PMA/ionomycin and labeled with the IFNγ cytokine cell-capture reagent (Miltenyi Biotech) followed by FACS isolation of IFNγ and IFNγ$^+$ populations, as previously described (11). The second set was expanded to day 14 prior to reactivation and cytokine cell capture.

For each sample, 25 ng total RNA were amplified using the Ovation® Pico WTA System (NuGen) and labeled with Encore Biotin Module V2 (NuGen). GeneChip® Human Genome U133 Plus 2.0 arrays (Affymetrix) were hybridized to 5 µg labeled, amplified cDNA, washed, stained, and scanned according to the protocol described in the GeneChip Expression analysis manual (GEO accession number: GSE59786). Gene expression profiling data was extracted from the Affymetrix Microarray Suite 5.0 (MAS 5.0) software and used for subsequent statistical analyses.

Multiplex Cytokine Assay

Cytokine production was determined using the Human $T_H17$ Magnetic Bead Panel (HT17MG-14K-PX25, EMD Millipore) according to manufacturers instructions from culture supernatants collected and run in duplicate. Samples were processed on a Bio-Tek ELx405, detected with MAG-PIX system (EMD Millipore), and analyzed with Milliplex Analyst software.

Data Analysis

An ANOVA with a posthoc Tukey multiple test correction was used for analysis of cytometric data utilizing Prism (GraphPad, v6). Geister-Greenhouse variance correction method was applied to the data to account for the difference in variance between Treg and Tconv, with values matched between each individual.

Following are examples that illustrate procedures for practicing the invention. These examples should not be construed as limiting. The examples and embodiments described herein are for illustrative purposes only and various modifications or changes in light thereof will be suggested to persons skilled in the art and are included within the spirit and purview of this application.

Example 1—TIGIT is Enriched in the tTreg

Human Treg display a considerable degree of heterogeneity. To limit biases for putatively identified surface markers, Treg were FACS-sorted following intracellular staining for FOXP3 and Helios. Tconv (FOXP3-Helios), FOXP3+ Helios−, and tTreg subsets (FOXP3+ Helios+) (FIG. 1A) were sorted, which then underwent direct mRNA hybridization that facilitates the direct quantitation of mRNA transcripts without reverse-transcription and amplification. This approach is compatible with partially degraded RNA samples, such as those obtained from fixed samples.

Patient-to-patient variance accounted for 77% of the expression differences observed between the samples, however genes putatively associated with Treg were identified, including CTLA-4 and IL2RA (Table 1). Specifically, the mRNA levels of TIGIT were found to be 12.4-times higher in tTreg compared to Tconv ($p<0.05$; FIG. 1B). In addition, strong co-expression of TIGIT and Helios in CD4+FOXP3+ T cells was observed (FIG. 1C). Thus, TIGIT expression is maintained by FOXP3 and TIGIT may play an important role in immune regulation.

Given that TIGIT and CD226 compete for binding to the ligand CD155, their surface expression was analyzed on CD4+ T cells in combination with FOXP3 and Helios (FIG. 2). Strikingly, tTreg had the highest percentage of TIGIT+ cells (83.4%±6.2%) and did not express CD226 in the absence of TIGIT (FIG. 2A). In contrast, Tconv cells co-expressed TIGIT only with high CD226 expression, suggesting TIGIT may play an important role in Tconv after activation. TIGIT expression by tTreg was increased in frequency and gMFI compared to FOXP3+ Helios− T cells, and the lowest frequency of TIGIT+ cells and gMFI found in Tconv (FIG. 2B, left graphs). In contrast, CD226 expression was higher in Tconv cells followed by FOXP3+ Helios, and then tTreg (FIG. 2B, right graphs). FOXP3+ Helios− T cells demonstrated an intermediate phenotype for CD226 and TIGIT expression. CD96 (TACTILE; T cell activation, increased late expression), a ligand that also binds CD155 was also analyzed and CD96 expression positively correlated with CD226 but did not demonstrate the dynamic range observed for CD226 (data not shown). Hence, the downstream analyses were limited to TIGIT and CD226.

TABLE 1

Differentially expressed genes between transcription factor-sorted CD4+ T cell subsets*

| Symbol | Gene Name | FOXP3+Helios− vs Tconv | tTregs vs Tconv | FOXP3+Helios− vs tTreg |
|---|---|---|---|---|
| ABU | c-abl oncogene 1, non-receptor tyrosine kinase | — | 1.9 | — |
| APP | amyloid beta (A4) precursor protein | — | — | −1.3 |
| ATM | ataxia telangiectasia mutated | — | 1.2 | — |
| BCL2 | B-cell CLL/lymphoma 2 | −1.5 | — | — |
| C8B | complement component 8, beta polypeptide | — | — | −1.4 |
| CD6 | CD6 molecule | — | −2.4 | 1.9 |
| CD96 | CD96 molecule | −1.6 | −1.6 | — |
| CHUK | conserved helix-loop-helix ubiquitous kinase | −2.5 | — | — |
| CSF2RB | colony stimulating factor 2 receptor, beta, low-affinity (granulocyte-macrophage) | — | 7.9 | −10 |
| CTLA4 | cytotoxic T-lymphocyte-associated protein 4 | 5.2 | 4.9 | — |
| CXCR3 | chemokine (C—X—C motif) receptor 3 | — | — | −1.7 |
| EEF1G | eukaryotic translation elongation factor 1 gamma | −1.3 | — | — |
| ETS1 | v-ets avian erythroblastosis virus E26 oncogene homolog I | — | — | −1.3 |
| FOXP3 | forkhead box P3 | 21.8 | 48.7 | — |
| HLA-DPB1 | major histocompatibility complex, class II, DP beta I | — | — | −5 |
| IKZF2 | IKAROS family zinc finger 2 (Helios) | −2.1 | — | — |
| IL10RA | interleukin 10 receptor, alpha | 2 | 2.2 | — |
| IL11RA | interleukin 11 receptor, alpha | −1.4 | — | — |
| IL13 | interleukin 13 | — | — | −1.4 |
| IL1R2 | interleukin 1 receptor, type II | 1.5 | — | — |
| IL23R | interleukin 23 receptor | — | — | −1.4 |
| ILAR | interleukin 4 receptor | −2.6 | — | — |
| IL6ST | interleukin 6 signal transducer | −2 | — | — |
| IL7R | interleukin 7 receptor | — | −2.3 | — |
| IRF1 | interferon regulatory factor 1 | — | — | −1.3 |
| IRF4 | interferon regulatory factor 4 | 4.1 | 3.4 | — |
| ITGA4 | integrin, alpha 4 (antigen CD49D, alpha 4 subunit of VLA-4 receptor) | −1.5 | — | — |
| JAK3 | Janus kinase 3 | — | −1.4 | — |
| MAP4K4 | mitogen-activated protein kinase kinase kinase kinase 4 | −1.4 | — | — |
| MARCO | macrophage receptor with collagenous structure | 1.1 | — | — |
| MYD88 | myeloid differentiation primary response 88 | −2 | — | — |
| NCAM1 | neural cell adhesion molecule I | −4 | — | — |
| NCF4 | neutrophil cytosolic factor 4, 40 kDa | 8.9 | 14 | — |
| NFATC2 | nuclear factor of activated T-cells, cytoplasmic, calcineurin-dependent 2 | — | −1.4 | — |
| NFKB2 | nuclear factor of kappa light polypeptide gene enhancer in B-cells 2 (p49/p100) | −1.8 | — | — |
| PRKCD | protein kinase C, delta | — | — | 2.7 |
| PSMB10 | proteasome (prosome, macropain) subunit beta type 10 | — | 1.3 | — |
| PSMB8 | proteasome (prosome, macropain) subunit, beta type, 8 | 2.2 | — | — |
| PSMB9 | proteasome (prosome, macropain) subunit, beta type, 9 | −1.4 | — | — |
| PTGER4 | prostaglandin E receptor 4 (subtype EP4) | — | — | 1.5 |
| PTK2 | protein tyrosine kinase 2 | — | −5 | — |
| RUNX1 | runt-related transcription factor 1 | −1.5 | −1.7 | — |
| STAT3 | signal transducer and activator of transcription 3 (acute-phase response factor) | −1.9 | — | — |

TABLE 1-continued

Differentially expressed genes between transcription factor-sorted CD4+ T cell subsets*

| Symbol | Gene Name | FOXP3+Helios− vs Tconv | tTregs vs Tconv | FOXP3+Helios− vs tTreg |
|---|---|---|---|---|
| STAT4 | signal transducer and activator of transcription 4 | −2.7 | −4.2 | — |
| STAT6 | signal transducer and activator of transcription 6, interleukin-4 induced | −1.3 | — | — |
| TAL1 | T-cell acute lymphocytic leukemia 1 | 1.4 | — | — |
| TGFB1 | transforming growth factor, beta 1 | −1.2 | — | — |
| TIGIT | T cell immunoreceptor with Ig and ITIM domains | — | 12.4 | — |
| TLR1 | toil-like receptor I | — | — | 10 |
| TMEM173 | transmembrane protein 173 | — | −1.4 | — |
| TNFAIP3 | tumor necrosis factor, alpha-induced protein 3 | −1.7 | — | — |
| TNFRSF1B | Tumor necrosis factor receptor superfamily, member 1B | 11.4 | 13.4 | — |
| TNFSF12 | tumor necrosis factor (ligand) superfamily, member 12 | −1.7 | — | — |
| TNFSF15 | tumor necrosis factor (ligand) superfamily, member 15 | 1.4 | — | — |
| XCL1 | chemokine (C motif) ligand 1 | — | — | 10 |

*The expression profile of CD4+ T cells FAC sorted by FOXP3 and Helios was analyzed by the nCounter. A paired ANOVA coupled with the Bonferroni multiple test correction (MTC) was used to determine differentially regulated genes with a significance value of p < 0.05 (n = 3). The fold change was calculated by taking the geometric mean of the counts, then dividing one subset by another. Only the ratios of significant comparisons are shown.

TABLE 2

Differentially expressed genes between expanded Tconv and Treg subsets expressing CD226 and TIGIT.*

| Symbol | Description | p value | FDR | C − T − mean | | C + T − mean | |
|---|---|---|---|---|---|---|---|
| | | | | Mean | SEM | Mean | SEM |
| CD40LG | CD40 ligand | 2.33E−02 | 9.19E−06 | 1.33E+02 | 1.50E+01 | 5.94E+02 | 3.53E+01 |
| 1L1R1 | interleukin 1 receptor, type 1 | 2.36E−02 | 1.37E−05 | 6.48E+02 | 1.75E+02 | 3.04E+02 | 5.86E+00 |
| TNFRSF1B | tumor necrosis factor receptor superfamily, member 1B | 2.44E−02 | 6.25E−05 | 7.59E+03 | 6.16E+02 | 4.61E+03 | 1.53E+02 |
| G6PD | glucose-6-phosphate dehydrogenase | 2.50E−02 | 7.82E−05 | 7.80E+02 | 6.08E+00 | 7.80E+02 | 3.65E+01 |
| FOXP3 | forkhead box P3 | 2.54E−02 | 1.54E−04 | 5.12E+03 | 4.15E+02 | 3.65E+03 | 3.08E+02 |
| FN1 | fibronectin 1 | 1.63E−04 | 1.63E−04 | 6.44E+01 | 5.66E+00 | 7.08E+01 | 1.74E+00 |
| TGFBR1 | transforming growth factor, beta receptor 1 | 1.64E−04 | 1.64E−04 | 1.04E+03 | 2.74E+01 | 6.40E+02 | 4.21E+01 |
| CD97 | CD97 molecule | 2.56E−04 | 2.56E−04 | 1.73E+03 | 3.52E+01 | 1.56E+03 | 2.74E+01 |
| IL7 | interleukin 7 | 2.64E−04 | 2.64E−04 | 9.22E+02 | 1.51E+02 | 7.10E+01 | 3.48E+00 |
| POU2F2 | POU class 2 homeobox 2 | 2.67E−04 | 2.67E−04 | 7.77E+02 | 3.54E+01 | 5.68E+02 | 1.61E+01 |
| TIGIT | T cell immunoreceptor with Ig and ITIM domains | 3.17E−04 | 3.17E−04 | 1.31E+03 | 1.51E+02 | 4.52E+02 | 2.19E+01 |
| CTLA4 | cytotoxic T-lymphocyte-associated protein 4 | 3.43E−04 | 3.43E−04 | 5.46E+03 | 2.85E+02 | 5.85E+03 | 3.63E+02 |
| CD53 | CD53 molecule | 3.83E−04 | 3.83E−04 | 7.03E+03 | 1.22E+02 | 6.02E+03 | 3.93E+02 |
| CD28 | CD28 molecule | 4.10E−04 | 4.10E−04 | 3.10E+03 | 1.33E+02 | 3.32E+03 | 3.33E+02 |
| IL1R2 | interleukin 1 receptor, type II | 4.38E−04 | 4.38E−04 | 6.42E+02 | 8.81E+01 | 5.80E+02 | 7.24E+01 |
| IL1RN | interleukin 1 receptor antagonist | 4.80E−04 | 4.80E−04 | 2.30E+02 | 2.84E+01 | 3.69E+02 | 9.46E+01 |
| IL7R | interleukin 7 receptor | 5.06E−04 | 5.06E−04 | 4.96E+01 | 3.40E+00 | 1.28E+02 | 8.14E+00 |
| IL2 | interleukin 2 | 6.18E−04 | 6.18E−04 | 1.99E+01 | 2.45E+00 | 2.27E+01 | 5.63E+00 |
| CSF2RB | colony stimulating factor 2 receptor, beta, low-affinity (granulocyte-macrophage) | 6.66E−04 | 6.66E−04 | 5.05E+02 | 1.07E+02 | 1.65E+02 | 4.00E+01 |
| LCP2 | lymphocyte cytosolic protein 2 (SH2 domain containing leukocyte protein of 76 kDa) | 7.10E−04 | 7.10E−04 | 6.82E+03 | 2.18E+02 | 5.12E+03 | 1.33E+02 |
| ITGAM | integrin, alpha M (complement component 3 receptor 3 subunit) | 7.45E−04 | 7.45E−04 | 2.74E+03 | 1.22E+02 | 2.16E+03 | 2.65E+02 |
| XBP1 | X-box binding protein 1 | 8.26E−04 | 8.26E−04 | 2.45E+02 | 1.68E+01 | 5.37E+02 | 4.87E+01 |
| ICAM2 | intercellular adhesion molecule 2 | 8.38E−04 | 8.38E−04 | 1.74E+03 | 1.03E+02 | 1.71E+03 | 1.66E+02 |
| PTPN6 | protein tyrosine phosphatase, non-receptor type 6 | 8.98E−04 | 8.98E−04 | 2.57E+03 | 1.27E+02 | 2.62E+03 | 1.94E+02 |
| TMEM173 | transmembrane protein 173 | 9.26E−04 | 9.26E−04 | 7.90E+03 | 2.55E+02 | 9.61E+03 | 7.02E+02 |
| IL2RA | interleukin 2 receptor, alpha | 9.70E−04 | 9.70E−04 | 2.58E+04 | 3.38E+02 | 2.22E+04 | 1.34E+03 |

TABLE 2-continued

Differentially expressed genes between expanded Tconv and Treg subsets expressing CD226 and TIGIT.*

| Gene | Description | | | | | | |
|---|---|---|---|---|---|---|---|
| CD59 | CD59 molecule, complement regulatory protein | 1.01E-03 | 1.01E-03 | 3.31E+03 | 2.12E+02 | 3.99E+03 | 6.59E+02 |
| PDGFRB | platelet-derived growth factor receptor, beta polypeptide | 1.05E-03 | 1.05E-03 | 1.34E+02 | 1.30E+01 | 9.86E+01 | 2.29E+00 |
| NCF4 | neutrophil cytosolic factor 4, 40 kDa | 1.10E-03 | 1.10E-03 | 1.70E+03 | 4.47E+01 | 1.15E+03 | 4.98E+01 |
| CD46 | CD46 molecule, complement regulatory protein | 1.11E-03 | 1.11E-03 | 1.43E+03 | 4.07E+01 | 1.39E+03 | 3.16E+01 |
| TNFSF13B | tumor necrosis factor (ligand) superfamily, member 13b | 1.12E-03 | 1.12E-03 | 6.66E+02 | 7.12E+01 | 1.77E+02 | 7.29E+00 |
| SMAD3 | SMAD family member 3 | 1.26E-03 | 1.26E-03 | 1.96E+02 | 1.14E+01 | 2.90E+02 | 2.31E+01 |
| CCR6 | chemokine (C-C motif) receptor 6 | 1.29E-03 | 1.29E-03 | 3.74E+01 | 3.98E+00 | 4.72E+01 | 7.31E+00 |
| IKZF2 | IKAROS family zinc finger 2 (Helios) | 1.36E-03 | 1.36E-03 | 2.92E+03 | 2.39E+02 | 1.10E+03 | 1.53E+02 |
| TNFRSF13B | tumor necrosis factor receptor superfamily, member 13B | 1.41E-03 | 1.41E-03 | 3.83E+01 | 8.01E+00 | 3.15E+01 | 7.80E+00 |
| IL22 | interleukin 22 | 1.41E-03 | 1.41E-03 | 1.23E+01 | 6.97E-01 | 1.41E+01 | 3.54E+00 |
| BATF3 | basic leucine zipper transcription factor, ATF-like 3 | 1.45E-03 | 1.45E-03 | 3.49E+01 | 2.60E+00 | 1.15E+02 | 1.11E+01 |
| CD4 | CD4 molecule | 1.48E-03 | 1.48E-03 | 1.51E+03 | 1.02E+02 | 1.42E+03 | 1.24E+02 |
| IL6R | interleukin 6 receptor | 1.52E-03 | 1.52E-03 | 3.59E+02 | 5.44E+01 | 3.91E+02 | 5.72E+01 |
| MAP4K2 | mitogen-activated protein kinase kinase kinase kinase 2 | 1.58E-03 | 1.58E-03 | 1.35E+03 | 1.53E+01 | 1.03E+03 | 3.13E+01 |
| NFIL3 | nuclear factor, interleukin 3 regulated | 1.98E-03 | 1.98E-03 | 2.01E+02 | 3.57E+01 | 4.75E+02 | 1.55E+01 |
| HLA-B | major histocompatibility complex, class 1, B | 2.02E-03 | 2.02E-03 | 3.18E+04 | 1.75E+03 | 2.83E+04 | 1.62E+02 |
| SPP1 | secreted phosphoprotein 1 | 2.08E-03 | 2.08E-03 | 4.08E+02 | 2.81E+01 | 4.49E+02 | 1.33E+02 |
| CD99 | CD99 molecule | 2.15E-03 | 2.15E-03 | 3.97E+03 | 8.16E+01 | 6.06E+03 | 5.97E+02 |
| BCL6 | B-cell CLL/lymphoma 6 | 2.16E-03 | 2.16E-03 | 1.93E+02 | 6.77E+00 | 1.25E+02 | 2.86E+01 |
| CD40 | CD40 molecule, TNF receptor superfamily member 5 | 2.31E-03 | 2.31E-03 | 6.12E+01 | 4.52E+00 | 4.49E+01 | 2.99E+00 |
| IRF8 | interferon regulatory factor 8 | 2.44E-03 | 2.44E-03 | 4.99E+01 | 6.73E+00 | 4.77E+01 | 6.50E+00 |
| PDCD2 | programmed cell death 2 | 2.46E-03 | 2.46E-03 | 3.79E+02 | 1.76E+01 | 3.76E+02 | 2.86E+01 |
| CD79A | CD79a molecule, immunoglobulin-associated alpha | 2.71E-03 | 2.71E-03 | 2.41E+02 | 3.35E+01 | 1.19E+02 | 1.35E+01 |
| MAF | v-maf avian musculoaponeurotic fibrosarcoma oncogene homolog | 2.80E-03 | 2.80E-03 | 2.24E+03 | 3.65E+02 | 2.49E+03 | 2.48E+02 |
| GFI1 | growth factor independent 1 transcription repressor | 2.92E-03 | 2.92E-03 | 3.71E+02 | 3.21E+01 | 6.04E+02 | 4.82E+01 |
| BID | BH3 interacting domain death agonist | 2.98E-03 | 2.98E-03 | 6.12E+01 | 4.52E+00 | 4.15E+01 | 5.89E+00 |
| MX1 | myxovirus (influenza virus) resistance 1, interferon-inducible protein p78 (mouse) | 3.23E-03 | 3.23E-03 | 1.24E+04 | 8.49E+02 | 2.47E+03 | 6.31E+02 |
| CD86 | CD86 molecule | 3.24E-03 | 3.24E-03 | 1.58E+02 | 2.75E+01 | 2.95E+02 | 4.51E+01 |
| SIGIRR | Single Immunoglobulin and toll-interleukin 1 receptor (TIR) domain | 3.38E-03 | 3.38E-03 | 9.28E+02 | 5.27E+01 | 6.36E+02 | 9.82E+01 |
| SELPLG | selectin P ligand | 3.45E-03 | 3.45E-03 | 4.09E+02 | 2.71E+01 | 3.17E+02 | 2.82E+01 |
| FKBP5 | FK506 binding protein 5 | 3.72E-03 | 3.72E-03 | 2.49E+02 | 2.15E+02 | 1.33E+03 | 1.99E+02 |
| SKI | v-ski avian sarcoma viral oncogene homolog | 4.07E-03 | 4.07E-03 | 1.03E+03 | 5.16E+01 | 8.42E+02 | 6.15E+01 |
| IGF2R | insulin-like growth factor 2 receptor | 4.43E-03 | 4.43E-03 | 5.49E+02 | 3.28E+01 | 5.43E+02 | 4.16E+01 |
| TCF7 | transcription factor 7 (T-cell specific, HMG-box) | 4.47E-03 | 4.47E-03 | 1.77E+02 | 8.23E+00 | 7.01E+01 | 4.94E+00 |
| CEACAM1 | carcinoembryonic antigen-related cell adhesion molecule 1 (biliary glycoprotein) | 4.75E-03 | 4.75E-03 | 6.93E+02 | 1.07E+02 | 5.91E+02 | 4.51E+01 |
| C1QBP | complement component 1, q subcomponent binding protein | 4.87E-03 | 4.87E-03 | 3.38E+03 | 3.60E+02 | 3.16E+03 | 2.69E+02 |

TABLE 2-continued

Differentially expressed genes between expanded Tconv and Treg subsets expressing CD226 and TIGIT.*

| | | | | | | | |
|---|---|---|---|---|---|---|---|
| CASP8 | caspase 8, apoptosis-related cysteine peptidase | 4.91E−03 | 4.91E−03 | 1.84E+03 | 8.66E+01 | 1.60E+03 | 8.06E+01 |
| FAS | Fas cell surface death receptor | 5.10E−03 | 5.10E−03 | 2.92E+02 | 6.81E+01 | 2.18E+02 | 2.54E+01 |
| BCAP31 | B-cell receptor-associated protein 31 | 5.15E−03 | 5.15E−03 | 1.42E+03 | 6.57E+01 | 1.32E+03 | 4.73E+01 |
| CD7 | CD7 molecule | 5.19E−03 | 5.19E−03 | 1.61E+03 | 1.15E+02 | 1.05E+03 | 6.71E+01 |
| IL11RA | interleukin 11 receptor, alpha | 5.34E−03 | 5.34E−03 | 1.70E+02 | 6.63E+00 | 1.40E+02 | 1.21E+01 |
| CD80 | CD80 molecule | 5.40E−03 | 5.40E−03 | 1.37E+03 | 1.29E+02 | 8.40E+02 | 1.15E+02 |
| IKBKE | inhibitor of kappa light polypeptide gene enhancer in B-cells, kinase epsilon | 5.41E−03 | 5.41E−03 | 8.22E+02 | 4.59E+01 | 6.15E+02 | 6.42E+01 |
| CRADD | CASP2 and RIPK1 domain containing adaptor with death domain | 5.42E−03 | 5.42E−03 | 1.80E+02 | 1.86E+01 | 1.46E+02 | 1.80E+01 |
| CD44 | CD44 molecule (Indian blood group) | 5.70E−03 | 5.70E−03 | 1.46E+03 | 2.52E+01 | 1.33E+03 | 5.84E+01 |
| ITGB2 | integrin, beta 2 (complement component 3 receptor 3 and 4 subunit) | 5.87E−03 | 5.87E−03 | 3.27E+03 | 8.28E+01 | 3.34E+03 | 3.52E+02 |
| BCL3 | B-cell CLL/lymphoma 3 | 6.30E−03 | 6.30E−03 | 5.29E+02 | 4.63E+01 | 5.85E+02 | 1.48E+01 |
| CCRL2 | chemokine (C-C motif) receptor-like 2 | 6.39E−03 | 6.39E−03 | 2.24E+02 | 9.69E+00 | 1.48E+02 | 1.64E+01 |
| HPRT1 | hypoxanthine phosphoribosyltransferase 1 | 6.58E−03 | 6.58E−03 | 2.29E+03 | 8.38E+01 | 2.80E+03 | 8.12E+01 |
| CISH | cytokine inducible SH2-containing protein | 7.18E−03 | 7.18E−03 | 2.80E+03 | 1.81E+02 | 2.00E+03 | 1.62E+02 |
| IRAK1 | interleukin-1 receptor-associated kinase 1 | 7.22E−03 | 7.22E−03 | 7.38E+02 | 4.19E+01 | 9.42E+02 | 5.99E+01 |
| LTA | lymphotoxin alpha | 7.23E−03 | 7.23E−03 | 8.76E+03 | 6.07E+02 | 5.32E+03 | 1.80E+03 |
| CTSC | cathepsin C | 9.02E−03 | 9.02E−03 | 6.42E+03 | 1.19E+03 | 6.43E+03 | 9.78E+02 |
| ETS1 | v-ets avian erythroblastosis virus E26 oncogene homolog 1 | 9.28E−03 | 9.28E−03 | 1.88E+04 | 1.65E+03 | 1.50E+04 | 8.24E+02 |
| CD3D | CD3d molecule, delta (CD3-TCR complex) | 9.32E−03 | 9.32E−03 | 9.16E+03 | 3.74E+02 | 8.26E+03 | 5.04E+02 |
| TNFSF12 | tumor necrosis factor (ligand) superfamily, member 12 | 9.38E−03 | 9.38E−03 | 1.48E+03 | 1.61E+02 | 9.37E+02 | 3.34E+01 |
| IL16 | interleukin 16 | 9.83E−03 | — | 3.63E+03 | 4.05E+02 | 1.65E+03 | 2.48E+01 |
| CXCL2 | chemokine (C—X—C motif) ligand 2 | 1.02E−02 | — | 2.81E+01 | 5.60E+00 | 3.24E+01 | 5.05E+00 |
| TGFB1 | transforming growth factor, beta 1 | 1.04E−02 | — | 2.82E+03 | 2.48E+02 | 2.57E+03 | 3.21E+02 |
| HLA-A | major histocompatibility complex, class I, A | 1.07E−02 | — | 3.18E+04 | 4.28E+03 | 2.71E+04 | 1.82E+03 |
| IL18RAP | interleukin 18 receptor accessory protein | 1.10E−02 | — | 5.94E+01 | 9.69E+00 | 4.11E+01 | 7.20E+00 |
| TLR1 | toll-like receptor 1 | 1.13E−02 | — | 5.85E+02 | 8.02E+01 | 1.64E+02 | 2.41E+01 |
| CEBPB | CCAAT/enhancer binding protein (C/EBP), beta | 1.14E−02 | — | 4.92E+02 | 3.73E+00 | 7.32E+02 | 1.15E+02 |
| LAIR1 | leukocyte-associated immunoglobulin-like receptor 1 | 1.15E−02 | — | 1.02E+03 | 3.67E+01 | 8.86E+02 | 4.07E+01 |
| CD247 | CD247 molecule | 1.18E−02 | — | 5.33E+03 | 3.99E+02 | 4.05E+03 | 3.67E+02 |
| MYD88 | myeloid differentiation primary response 88 | 1.19E−02 | — | 1.79E+03 | 1.46E+02 | 1.50E+03 | 1.09E+02 |
| SELL | selectin L | 1.20E−02 | — | 9.20E+03 | 1.12E+03 | 7.86E+03 | 1.09E+03 |
| TLR5 | toll-like receptor 5 | 1.25E−02 | — | 3.22E+01 | 1.90E+00 | 2.84E+01 | 4.74E+00 |
| NFKBIZ | nuclear factor of kappa light polypeptide gene enhancer in B-cells inhibitor, zeta | 1.28E−02 | — | 2.23E+03 | 5.43E+02 | 1.61E+03 | 1.48E+02 |
| CD27 | CD27 molecule | 1.33E−02 | — | 3.65E+03 | 6.26E+02 | 2.59E+03 | 4.28E+02 |
| CXCR4 | chemokine (C—X—C motif) receptor 4 | 1.41E−02 | — | 8.15E+03 | 6.12E+02 | 6.08E+03 | 4.18E+02 |
| BATF | basic leucine zipper transcription factor, ATF-like | 1.41E−02 | — | 1.02E+03 | 7.83E+01 | 1.14E+03 | 1.14E+02 |
| STAT2 | signal transducer and activator of transcription 2, 113 kDa | 1.44E−02 | — | 2.70E+03 | 4.34E+02 | 1.40E+03 | 6.65E+01 |
| CCR5 | chemokine (C-C motif) receptor 5 (gene/pseudogene) | 1.57E−02 | — | 7.72E+02 | 8.47E+01 | 4.70E+02 | 1.10E+02 |

TABLE 2-continued

Differentially expressed genes between expanded Tconv and Treg subsets expressing CD226 and TIGIT.*

| Gene | Description | | | | | | |
|---|---|---|---|---|---|---|---|
| HLA-DMB | major histocompatibility complex, class II, DM beta | 1.59E-02 | — | 5.66E+02 | 5.90E+01 | 4.98E+02 | 1.98E+01 |
| PDCD1 | programmed cell death 1 | 1.59E-02 | — | 4.21E+01 | 1.25E+00 | 5.21E+01 | 1.19E+01 |
| ITGB1 | integrin, beta 1 (fibronectin receptor, beta polypeptide, antigen CD29 includes MDF2, MSK12) | 1.60E-02 | — | 5.53E+02 | 7.96E+00 | 1.52E+03 | 2.78E+02 |
| POLR2A | Polymerase (RNA) II (DNA directed) Polypeptide A, 220 kDa | 1.65E-02 | — | 1.75E+03 | 2.22E+01 | 1.63E+03 | 3.38E+01 |
| PRDM1 | PR domain containing 1, with ZNF domain | 1.71E-02 | — | 2.76E+03 | 6.01E+01 | 3.23E+03 | 2.59E+02 |
| IRF7 | interferon regulatory factor 7 | 1.73E-02 | — | 8.30E+02 | 6.92E+01 | 3.72E+02 | 1.53E+01 |
| ICAM3 | intercellular adhesion molecule 3 | 1.81E-02 | — | 4.24E+03 | 3.07E+02 | 3.67E+03 | 4.46E+02 |
| PSMB7 | proteasome (prosome, macropain) subunit, beta type, 7 | 1.85E-02 | — | 3.48E+03 | 1.20E+02 | 3.74E+03 | 6.65E+01 |
| IL10RA | interleukin 10 receptor, alpha | 1.92E-02 | — | 4.25E+03 | 6.50E+02 | 2.84E+03 | 3.96E+02 |
| CCR7 | chemokine (C-C motif) receptor 7 | 1.94E-02 | — | 1.49E+03 | 1.61E+02 | 7.00E+02 | 7.93E+01 |
| TNFRSF11A | tumor necrosis factor receptor superfamily, member 11a, NFKB activator | 1.95E-02 | — | 1.07E+03 | 1.19E+02 | 8.10E+02 | 1.03E+02 |
| APP | amyloid beta (A4) precursor protein | 2.02E-02 | — | 3.64E+02 | 3.78E+01 | 2.88E+02 | 1.15E+01 |
| FCER1G | Fc fragment of IgE, high affinity I, receptor for; gamma polypeptide | 2.05E-02 | — | 1.33E+03 | 1.98E+02 | 2.89E+02 | 7.86E+01 |
| IRF1 | interferon regulatory factor 1 | 2.12E-02 | — | 1.73E+03 | 2.42E+02 | 1.56E+03 | 6.91E+01 |
| B2M | beta-2-microglobulin | 2.16E-02 | — | 2.59E+05 | 3.47E+04 | 2.33E+05 | 2.23E+04 |
| NOD2 | nucleotide-binding oligomerization domain containing 2 | 2.22E-02 | — | 2.32E+01 | 3.14E+00 | 2.56E+01 | 7.71E+00 |
| ITGA4 | integrin, alpha 4 (antigen CD49D, alpha 4 subunit of VLA-4 receptor) | 2.28E-02 | — | 1.89E+03 | 1.68E+02 | 1.75E+03 | 1.13E+02 |
| MAP4K4 | mitogen-activated protein kinase kinase kinase kinase 4 | 2.33E-02 | — | 2.76E+03 | 3.83E+02 | 2.30E+03 | 3.32E+02 |
| TNF | tumor necrosis factor | 2.36E-02 | — | 1.12E+02 | 7.83E+00 | 8.96E+01 | 1.00E+01 |
| TAPBP | TAP binding protein (tapasin) | 2.44E-02 | — | 2.72E+03 | 1.14E+02 | 2.58E+03 | 1.10E+02 |
| TNFRSF9 | tumor necrosis factor receptor superfamily, member 9 | 2.50E-02 | — | 6.06E+02 | 8.20E+01 | 5.38E+02 | 1.58E+02 |
| LILRB4 | leukocyte immunoglobulin-like receptor, subfamily B (with TM and ITIM domains), member 4 | 2.54E-02 | — | 1.04E+01 | 1.42E+00 | 1.36E+01 | 2.62E+00 |
| PPARG | peroxisome proliferator-activated receptor gamma | 2.54E-02 | — | 2.30E+01 | 5.41E+00 | 8.07E+01 | 1.61E+01 |
| RARRES3 | retinoic acid receptor responder (tazarotene induced) 3 | 2.56E-02 | — | 1.02E+03 | 7.55E+01 | 6.40E+02 | 5.38E+01 |
| CXCR3 | chemokine (C—X—C motif) receptor 3 | 2.57E-02 | — | 2.00E+03 | 4.30E+02 | 1.29E+03 | 2.62E+02 |
| IL2RB | interleukin 2 receptor, beta | 2.60E-02 | — | 4.50E+03 | 1.36E+02 | 4.01E+03 | 3.46E+02 |
| GATA3 | GATA binding protein 3 | 2.69E-02 | — | 1.06E+02 | 2.36E+00 | 1.56E+02 | 6.83E+00 |
| CFP | complement factor properdin | 2.80E-02 | — | 1.30E+02 | 1.25E+01 | 8.02E+01 | 9.38E+00 |
| LY96 | lymphocyte antigen 96 | 2.84E-02 | — | 5.88E+02 | 5.28E+01 | 4.63E+02 | 4.55E+01 |
| CD58 | CD58 molecule | 2.89E-02 | — | 1.06E+03 | 5.45E+01 | 1.42E+03 | 4.91E+01 |
| LCK | lymphocyte-specific protein tyrosine kinase | 2.93E-02 | — | 5.45E+03 | 4.84E+02 | 4.77E+03 | 5.82E+02 |
| CD5 | CD5 molecule | 3.04E-02 | — | 3.70E+03 | 1.49E+02 | 3.45E+03 | 1.62E+02 |
| GZMA | granzyme A (granzyme 1, cytotoxic T-lymphocyte-associated serine esterase 3) | 3.08E-02 | — | 7.08E+01 | 5.02E+00 | 2.40E+03 | 5.60E+02 |

TABLE 2-continued

Differentially expressed genes between expanded Tconv and Treg subsets expressing CD226 and TIGIT.*

| Symbol | Description | | | | | | |
|---|---|---|---|---|---|---|---|
| NFATC1 | nuclear factor of activated T-cells, cytoplasmic, calcineurin-dependent 1 | 3.08E−02 | — | 1.85E+02 | 1.28E+01 | 2.17E+02 | 1.54E+01 |
| FYN | FYN oncogene related to SRC, FGR, YES | 3.12E−02 | — | 2.42E+03 | 2.74E+02 | 1.64E+03 | 1.07E+02 |
| ATM | ataxia telangiectasia mutated | 3.17E−02 | — | 6.64E+01 | 8.65E+00 | 8.54E+01 | 6.24E+00 |
| FCGR2C | Fc fragment of IgG, low affinity IIc, receptor for (CD32) (gene/pseudogene) | 3.24E−02 | — | 5.26E+01 | 4.32E+00 | 4.64E+01 | 3.83E+00 |
| FCGRT | Fc fragment of IgG, receptor, transporter, alpha | 3.25E−02 | — | 6.48E+01 | 2.27E+00 | 8.42E+01 | 1.19E+01 |
| GZMB | granzyme B (granzyme 2, cytotoxic T-lymphocyte-associated serine esterase 1) | 3.32E−02 | — | 3.74E+02 | 4.45E+01 | 2.65E+03 | 8.18E+02 |
| CD3E | CD3e molecule, epsilon (CD3-TCR complex) | 3.40E−02 | — | 5.76E+03 | 4.81E+02 | 5.60E+03 | 6.12E+02 |
| STAT6 | signal transducer and activator of transcription 6, interleukin-4 induced | 3.50E−02 | — | 2.05E+03 | 1.81E+02 | 1.30E+03 | 7.91E+01 |
| MR1 | major histocompatibility complex, class I-related | 3.51E−02 | — | 1.70E+02 | 3.42E+01 | 1.17E+02 | 1.26E+01 |
| TNFRSF8 | tumor necrosis factor receptor superfamily, member 8 | 3.59E−02 | — | 3.75E+02 | 1.32E+02 | 5.61E+02 | 1.32E+02 |
| MAPK11 | mitogen-activated protein kinase 11 | 3.61E−02 | — | 9.32E+01 | 3.31E+00 | 7.57E+01 | 3.11E+00 |
| TLR3 | toll-like receptor 3 | 3.62E−02 | — | 5.39E+01 | 6.64E+00 | 4.52E+01 | 7.74E+00 |
| JAK1 | Janus kinase 1 | 3.63E−02 | — | 2.91E+03 | 3.48E+02 | 2.65E+03 | 3.25E+02 |
| IFIT2 | interferon-induced protein with tetratricopeptide repeats 2 | 3.63E−02 | — | 1.68E+02 | 2.08E+01 | 6.16E+01 | 5.57E+00 |
| CASP2 | caspase 2, apoptosis-related cysteine peptidase | 3.82E−02 | — | 9.68E+02 | 9.84E+01 | 1.17E+03 | 1.01E+02 |
| TIRAP | toll-interleukin 1 receptor (TIR) domain containing adaptor protein | 3.88E−02 | — | 9.93E+01 | 7.28E+00 | 8.81E+01 | 8.80E+00 |
| RORC | RAR-related orphan receptor C | 4.02E−02 | — | 3.79E+01 | 5.21E+00 | 6.23E+01 | 1.38E+01 |
| RELA | v-rel avian reticuloendotheliosis viral oncogene homolog A | 4.04E−02 | — | 6.49E+02 | 4.10E+01 | 6.25E+02 | 1.63E+01 |
| PSMB8 | proteasome (prosome, macropain) subunit, beta type, 8 | 4.14E−02 | — | 1.10E+04 | 1.97E+02 | 1.12E+04 | 1.16E+02 |
| CD83 | CD83 molecule | 4.16E−02 | — | 3.66E+02 | 7.11E+01 | 1.97E+02 | 2.47E+01 |
| FCGR3A | Fc fragment of IgG, low affinity IIIa, receptor (CD16a) | 4.35E−02 | — | 8.28E+01 | 8.73E+00 | 7.40E+01 | 7.62E+00 |
| TNFSF11 | tumor necrosis factor (ligand) superfamily, member 11 | 4.53E−02 | — | 4.46E+01 | 2.64E+00 | 1.52E+02 | 3.22E+01 |
| HLA-DRB3 | major histocompatibility complex, class II, DR beta 3 | 4.57E−02 | — | 2.90E+03 | 5.02E+02 | 3.07E+03 | 2.94E+02 |
| ENTPD1 | ectonucleoside triphosphate diphosphohydrolase 1 | 4.68E−02 | — | 1.37E+01 | 4.20E+00 | 1.38E+01 | 3.60E+00 |
| TNFSF15 | tumor necrosis factor (ligand) superfamily, member 15 | 4.69E−02 | — | 5.93E+01 | 7.26E+00 | 7.05E+01 | 7.55E+00 |
| IFNAR2 | interferon (alpha, beta and omega) receptor 2 | 4.73E−02 | — | 2.15E+03 | 3.67E+02 | 1.84E+03 | 2.99E+02 |

| Symbol | Description | C + T + mean | | C − T + mean | | TConv mean | |
|---|---|---|---|---|---|---|---|
| | | Mean | SEM | Mean | SEM | Mean | SEM |
| CD40LG | CD40 ligand | 1.79E+02 | 2.70E+01 | 8.72E+01 | 3.04E+01 | 1.62E+03 | 3.85E+01 |
| 1L1R1 | interleukin 1 receptor, type 1 | 1.06E+03 | 2.03E+02 | 8.40E+02 | 7.06E+01 | 2.56E+01 | 2.08E+00 |
| TNFRSF1B | tumor necrosis factor receptor superfamily, member 1B | 8.70E+03 | 6.18E+02 | 8.13E+03 | 4.85E+02 | 8.66E+02 | 9.47E+01 |
| G6PD | glucose-6-phosphate dehydrogenase | 7.35E+02 | 1.31E+01 | 7.08E+02 | 3.87E+01 | 5.95E+02 | 4.26E+00 |

TABLE 2-continued

Differentially expressed genes between expanded Tconv and Treg subsets expressing CD226 and TIGIT.*

| Gene | Description | | | | | | |
|---|---|---|---|---|---|---|---|
| FOXP3 | forkhead box P3 | 5.25E+03 | 4.83E+02 | 5.10E+03 | 2.55E+02 | 2.53E+02 | 1.05E+02 |
| FN1 | fibronectin 1 | 5.20E+01 | 9.66E+00 | 6.19E+01 | 1.04E+01 | 2.11E+01 | 1.58E+00 |
| TGFBR1 | transforming growth factor, beta receptor 1 | 9.63E+02 | 6.16E+01 | 9.79E+02 | 1.27E+02 | 2.90E+02 | 2.69E+01 |
| CD97 | CD97 molecule | 1.89E+03 | 3.47E+01 | 1.75E+03 | 3.85E+01 | 1.33E+03 | 5.88E+00 |
| IL7 | interleukin 7 | 2.26E+02 | 1.19E+01 | 1.77E+02 | 9.03E+00 | 4.14E+01 | 4.12E+00 |
| POU2F2 | POU class 2 homeobox 2 | 9.21E+02 | 1.24E+02 | 9.34E+02 | 1.43E+02 | 2.27E+02 | 1.57E+01 |
| TIGIT | T cell immunoreceptor with Ig and ITIM domains | 1.80E+03 | 2.11E+02 | 2.34E+03 | 2.27E+02 | 5.18E+01 | 1.44E+00 |
| CTLA4 | cytotoxic T-lymphocyte-associated protein 4 | 8.53E+03 | 8.67E+02 | 7.44E+03 | 8.99E+02 | 1.15E+03 | 1.46E+02 |
| CD53 | CD53 molecule | 7.64E+03 | 4.75E+02 | 7.20E+03 | 8.59E+02 | 3.87E+03 | 1.38E+02 |
| CD28 | CD28 molecule | 4.55E+03 | 4.55E+02 | 3.99E+03 | 1.28E+02 | 1.73E+03 | 2.45E+01 |
| IL1R2 | interleukin 1 receptor, type II | 1.11E+03 | 5.36E+01 | 1.05E+03 | 3.51E+02 | 6.07E+01 | 4.58E+00 |
| IL1RN | interleukin 1 receptor antagonist | 3.96E+02 | 1.44E+01 | 3.55E+02 | 1.97E+02 | 7.40E+01 | 1.29E+01 |
| IL7R | interleukin 7 receptor | 8.27E+01 | 1.86E+01 | 6.85E+01 | 1.01E+01 | 1.16E+03 | 7.06E+01 |
| IL2 | interleukin 2 | 2.39E+01 | 8.23E+00 | 3.81E+01 | 6.33E+00 | 9.38E+01 | 4.14E+00 |
| CSF2RB | colony stimulating factor 2 receptor, beta, low-affinity (granulocyte-macrophage) | 7.84E+02 | 3.71E+01 | 8.62E+02 | 1.74E+02 | 1.06E+02 | 3.23E+01 |
| LCP2 | lymphocyte cytosolic protein 2 (SH2 domain containing leukocyte protein of 76 kDa) | 6.55E+03 | 4.53E+02 | 6.16E+03 | 5.98E+02 | 3.65E+03 | 9.98E+01 |
| ITGAM | integrin, alpha M (complement component 3 receptor 3 subunit) | 3.15E+03 | 4.56E+02 | 2.97E+03 | 5.27E+02 | 6.28E+02 | 7.83E+01 |
| XBP1 | X-box binding protein 1 | 2.57E+02 | 2.12E+01 | 2.43E+02 | 2.40E+01 | 1.16E+03 | 6.77E+01 |
| ICAM2 | intercellular adhesion molecule 2 | 2.20E+03 | 2.59E+02 | 2.01E+03 | 8.94E+01 | 7.88E+02 | 2.53E+01 |
| PTPN6 | protein tyrosine phosphatase, non-receptor type 6 | 3.17E+03 | 2.65E+02 | 3.08E+03 | 3.65E+01 | 2.03E+03 | 5.97E+01 |
| TMEM173 | transmembrane protein 173 | 1.06E+04 | 1.47E+02 | 1.02E+04 | 6.64E+02 | 5.06E+03 | 4.02E+02 |
| IL2RA | interleukin 2 receptor, alpha | 2.62E+04 | 1.23E+03 | 2.70E+04 | 2.36E+03 | 1.04E+04 | 9.43E+02 |
| CD59 | CD59 molecule, complement regulatory protein | 6.71E+03 | 1.13E+03 | 4.82E+03 | 3.11E+02 | 1.01E+03 | 2.70E+01 |
| PDGFRB | platelet-derived growth factor receptor, beta polypeptide | 2.27E+02 | 2.84E+01 | 1.24E+02 | 3.25E+00 | 6.91E+01 | 2.91E+00 |
| NCF4 | neutrophil cytosolic factor 4, 40 kDa | 1.53E+03 | 3.95E+01 | 1.88E+03 | 1.33E+02 | 8.33E+02 | 6.35E+01 |
| CD46 | CD46 molecule, complement regulatory protein | 1.77E+03 | 1.62E+01 | 1.64E+03 | 1.29E+02 | 1.24E+03 | 5.70E+01 |
| TNFSF13B | tumor necrosis factor (ligand) superfamily, member 13b | 6.22E+02 | 1.20E+02 | 6.44E+02 | 6.11E+01 | 1.03E+02 | 4.82E+00 |
| SMAD3 | SMAD family member 3 | 2.09E+02 | 2.75E+01 | 2.51E+02 | 2.07E+01 | 8.26E+02 | 4.66E+01 |
| CCR6 | chemokine (C-C motif) receptor 6 | 1.63E+02 | 1.20E+01 | 1.15E+02 | 1.31E+01 | 1.85E+01 | 1.92E+00 |
| IKZF2 | IKAROS family zinc finger 2 (Helios) | 3.50E+03 | 9.31E+02 | 4.00E+03 | 4.87E+02 | 3.56E+01 | 1.53E−01 |
| TNFRSF13B | tumor necrosis factor receptor superfamily, member 13B | 8.65E+01 | 4.81E+0 | 5.55E+01 | 2.37E+00 | 2.47E+01 | 2.41E+00 |
| IL22 | interleukin 22 | 1.35E+01 | 4.14E+00 | 1.91E+01 | 2.49E+00 | 2.80E+02 | 1.80E+01 |
| BATF3 | basic leucine zipper transcription factor, ATF-like 3 | 6.54E+01 | 4.56E+00 | 5.58E+01 | 7.27E+00 | 3.57E+02 | 3.01E+01 |
| CD4 | CD4 molecule | 1.87E+03 | 1.57E+02 | 2.01E+03 | 5.05E+01 | 7.83E+02 | 8.41E+01 |
| IL6R | interleukin 6 receptor | 1.00E+03 | 1.88E+02 | 6.40E+02 | 4.41E+01 | 7.65E+01 | 1.30E+01 |
| MAP4K2 | mitogen-activated protein kinase kinase kinase kinase 2 | 1.33E+03 | 5.32E+01 | 1.47E+03 | 6.27E+01 | 8.01E+02 | 5.23E+01 |
| NFIL3 | nuclear factor, interleukin 3 regulated | 3.50E+02 | 2.80E+01 | 1.95E+02 | 2.16E+01 | 9.10E+02 | 1.71E+02 |
| HLA-B | major histocompatibility complex, class 1, B | 3.67E+04 | 4.11E+03 | 3.59E+04 | 6.67E+02 | 2.03E+04 | 9.95E+02 |
| SPP1 | secreted phosphoprotein 1 | 3.33E+02 | 1.17E+02 | 2.34E+02 | 5.00E+01 | 2.75E+01 | 4.12E+00 |
| CD99 | CD99 molecule | 5.41E+03 | 3.40E+02 | 4.66E+03 | 1.80E+01 | 6.52E+03 | 1.71E+02 |
| BCL6 | B-cell CLL/lymphoma 6 | 1.39E+02 | 1.85E+01 | 2.02E+02 | 5.80E+01 | 7.12E+01 | 7.54E+00 |

TABLE 2-continued

Differentially expressed genes between expanded Tconv and Treg subsets expressing CD226 and TIGIT.*

| Gene | Description | | | | | | |
|---|---|---|---|---|---|---|---|
| CD40 | CD40 molecule, TNF receptor superfamily member 5 | 9.80E+01 | 2.31E+01 | 8.36E+01 | 1.25E+01 | 1.89E+01 | 1.04E+00 |
| IRF8 | interferon regulatory factor 8 | 5.63E+01 | 8.71E+00 | 3.48E+01 | 3.97E+00 | 9.88E+01 | 4.40E00 |
| PDCD2 | programmed cell death 2 | 3.72E+02 | 8.39E+00 | 3.87E+02 | 5.00E+01 | 2.72E+02 | 1.45E+00 |
| CD79A | CD79a molecule, immunoglobulin-associated alpha | 2.27E+02 | 6.15E+01 | 3.02E+02 | 2.54E+01 | 3.78E+01 | 1.36E+00 |
| MAF | v-maf avian musculoaponeurotic fibrosarcoma oncogene homolog | 4.25E+03 | 2.54E+02 | 3.39E+03 | 4.48E+02 | 6.75E+02 | 2.29E+02 |
| GFI1 | growth factor independent 1 transcription repressor | 2.76E+02 | 5.63E+01 | 3.36E+02 | 3.33E+01 | 1.03E+03 | 6.57E+01 |
| BID | BH3 interacting domain death agonist | 5.50E+01 | 2.92E+00 | 6.77E+01 | 1.61E+00 | 2.78E+01 | 3.42E+00 |
| MX1 | myxovirus (influenza virus) resistance 1, interferon-inducible protein p78 (mouse) | 1.14E+04 | 2.15E+03 | 1.52E+04 | 3.71E+03 | 3.08E+03 | 7.56E+02 |
| CD86 | CD86 molecule | 3.35E+02 | 2.32E+01 | 1.57E+02 | 1.26E+01 | 3.62E+02 | 1.85E+01 |
| SIGIRR | Single Immunoglobulin and toll-interleukin 1 receptor (TIR) domain | 9.44E+02 | 9.18E+01 | 1.16E+03 | 2.18E+02 | 3.73E+02 | 2.04E+01 |
| SELPLG | selectin P ligand | 5.20E+02 | 7.55E+01 | 5.09E+02 | 3.89E+01 | 1.93E+02 | 3.14E+00 |
| FKBP5 | FK506 binding protein 5 | 1.59E+03 | 3.21E+02 | 2.13E+03 | 1.81E+02 | 6.59E+02 | 4.94E+01 |
| SKI | v-ski avian sarcoma viral oncogene homolog | 1.16E+03 | 8.27E+01 | 1.19E+03 | 1.92E+02 | 5.81E+02 | 1.69E+01 |
| IGF2R | insulin-like growth factor 2 receptor | 7.77E+02 | 7.75E+01 | 6.54E+02 | 6.29E+01 | 2.84E+02 | 2.10E+01 |
| TCF7 | transcription factor 7 (T-cell specific, HMG-box) | 2.67E+02 | 8.44E+01 | 2.89E+02 | 1.03E+02 | 1.08E+02 | 1.23E+00 |
| CEACAM1 | carcinoembryonic antigen-related cell adhesion molecule 1 (biliary glycoprotein) | 7.64E+02 | 7.57E+01 | 6.35E+02 | 9.50E+01 | 2.43E+02 | 1.16E+01 |
| C1QBP | complement component 1, q subcomponent binding protein | 2.55E+03 | 4.34E+02 | 2.55E+03 | 2.16E+02 | 4.57E+03 | 8.97E+01 |
| CASP8 | caspase 8, apoptosis-related cysteine peptidase | 3.38E+03 | 4.84E+02 | 2.80E+03 | 3.32E+02 | 1.11E+03 | 5.18E+01 |
| FAS | Fas cell surface death receptor | 5.83E+02 | 1.24E+02 | 3.41E+02 | 2.15E+01 | 1.17E+03 | 1.15E+01 |
| BCAP31 | B-cell receptor-associated protein 31 | 1.37E+03 | 4.99E+01 | 1.32E+03 | 6.87E+01 | 1.03E+03 | 1.51E+01 |
| CD7 | CD7 molecule | 1.14E+03 | 6.09E+01 | 1.63E+03 | 7.40E+01 | 6.05E+02 | 1.00E+02 |
| IL11RA | interleukin 11 receptor, alpha | 2.02E+02 | 3.99E+01 | 2.39E+02 | 5.98E+01 | 8.43E+01 | 6.46E+00 |
| CD80 | CD80 molecule | 1.35E+03 | 1.43E+02 | 1.35E+03 | 2.66E+02 | 3.41E+02 | 5.56E+01 |
| IKBKE | inhibitor of kappa light polypeptide gene enhancer in B-cells, kinase epsilon | 1.01E+03 | 1.18E+02 | 8.99E+02 | 1.31E+01 | 5.04E+02 | 3.88E+01 |
| CRADD | CASP2 and RIPK1 domain containing adaptor with death domain | 2.05E+02 | 1.12E+01 | 2.15E+02 | 2.26E+01 | 9.24E+01 | 7.21E+00 |
| CD44 | CD44 molecule (Indian blood group) | 1.50E+03 | 1.10E+02 | 1.61E+03 | 1.99E+02 | 8.06E+02 | 6.24E+01 |
| ITGB2 | integrin, beta 2 (complement component 3 receptor 3 and 4 subunit) | 3.45E+03 | 2.11E+02 | 3.55E+03 | 4.93E+02 | 2.22E+03 | 8.74E+01 |
| BCL3 | B-cell CLL/lymphoma 3 | 6.76E+02 | 4.39E+01 | 5.63E+02 | 4.75E+01 | 7.68E+02 | 1.54E+01 |
| CCRL2 | chemokine (C-C motif) receptor-like 2 | 2.39E+02 | 3.80E+01 | 2.21E+02 | 2.91E+01 | 1.00E+02 | 1.04E+01 |
| HPRT1 | hypoxanthine phosphoribosyltransferase 1 | 2.18E+03 | 1.33E+02 | 1.95E+03 | 1.28E+02 | 2.97E+03 | 7.68E+01 |
| CISH | cytokine inducible SH2-containing protein | 2.65E+03 | 3.45E+02 | 3.03E+03 | 2.71E+02 | 1.45E+03 | 4.18E+01 |
| IRAK1 | interleukin-1 receptor-associated kinase 1 | 9.09E+02 | 6.31E+01 | 7.44E+02 | 3.61E+01 | 1.10E+03 | 3.10E+01 |
| LTA | lymphotoxin alpha | 4.93E+03 | 7.88E+02 | 5.99E+03 | 1.54E+03 | 1.88E+03 | 4.86E+02 |
| CTSC | cathepsin C | 7.01E+03 | 1.13E+03 | 6.43E+03 | 4.74E+02 | 2.69E+03 | 7.04E+01 |
| ETS1 | v-ets avian erythroblastosis virus E26 oncogene homolog 1 | 1.89E+04 | 2.40E+03 | 1.89E+04 | 1.16E+03 | 1.11E+04 | 3.14E+02 |
| CD3D | CD3d molecule, delta (CD3-TCR complex) | 1.05E+04 | 1.32E+03 | 9.45E+03 | 8.88E+02 | 6.04E+03 | 2.05E+02 |

TABLE 2-continued

Differentially expressed genes between expanded Tconv and Treg subsets expressing CD226 and TIGIT.*

| | | | | | | | |
|---|---|---|---|---|---|---|---|
| TNFSF12 | tumor necrosis factor (ligand) superfamily, member 12 | 1.33E+03 | 1.39E+02 | 1.52E+03 | 1.87E+02 | 5.63E+02 | 5.20E+01 |
| IL16 | interleukin 16 | 2.87E+03 | 2.36E+02 | 3.88E+03 | 6.11E+02 | 1.56E+03 | 2.45E+01 |
| CXCL2 | chemokine (C—X—C motif) ligand 2 | 3.78E+01 | 1.42E+00 | 4.18E+01 | 5.05E+00 | 2.29E+01 | 1.19E+00 |
| TGFB1 | transforming growth factor, beta 1 | 3.06E+03 | 4.02E+02 | 3.03E+03 | 1.62E+02 | 1.77E+03 | 2.51E+01 |
| HLA-A | major histocompatibility complex, class I, A | 3.97E+04 | 7.80E+03 | 3.75E+04 | 2.27E+03 | 1.95E+04 | 7.43E+02 |
| IL18RAP | interleukin 18 receptor accessory protein | 3.77E+01 | 1.34E+00 | 6.14E+01 | 7.87E+00 | 2.09E+02 | 2.02E+01 |
| TLR1 | toll-like receptor 1 | 4.28E+02 | 1.29E+02 | 4.57E+02 | 3.93E+01 | 1.75E+02 | 8.54E+00 |
| CEBPB | CCAAT/enhancer binding protein (C/EBP), beta | 7.06E+02 | 3.99E+01 | 6.08E+02 | 6.29E+01 | 1.50E+03 | 1.38E+02 |
| LAIR1 | leukocyte-associated immunoglobulin-like receptor 1 | 9.29E+02 | 7.48E+01 | 1.07E+03 | 1.29E+02 | 5.49E+02 | 4.96E+01 |
| CD247 | CD247 molecule | 7.26E+03 | 1.13E+03 | 6.40E+03 | 1.24E+03 | 2.62E+03 | 7.86E+01 |
| MYD88 | myeloid differentiation primary response 88 | 2.05E+03 | 2.63E+02 | 2.06E+03 | 1.20E+02 | 1.07E+03 | 7.64E+01 |
| SELL | selectin L | 1.28E+04 | 2.47E+03 | 1.25E+04 | 1.28E+03 | 3.63E+03 | 5.18E+02 |
| TLR5 | toll-like receptor 5 | 4.76E+01 | 5.96E+00 | 3.10E+01 | 4.24E+00 | 1.74E+01 | 1.27E+00 |
| NFKBIZ | nuclear factor of kappa light polypeptide gene enhancer in B-cells inhibitor, zeta | 3.14E+03 | 4.11E+02 | 2.48E+03 | 3.25E+02 | 7.77E+02 | 1.10E+02 |
| CD27 | CD27 molecule | 4.28E+03 | 9.77E+02 | 4.13E+03 | 6.92E+02 | 6.59E+02 | 4.01E+01 |
| CXCR4 | chemokine (C—X—C motif) receptor 4 | 1.07E+04 | 1.88E+03 | 9.62E+03 | 4.59E+02 | 4.88E+03 | 5.88E+02 |
| BATF | basic leucine zipper transcription factor, ATF-like | 1.39E+03 | 1.16E+02 | 1.16E+03 | 2.60E+02 | 6.33E+02 | 3.89E+01 |
| STAT2 | signal transducer and activator of transcription 2, 113 kDa | 3.68E+03 | 8.40E+02 | 3.34E+03 | 6.23E+02 | 9.16E+02 | 6.31E+01 |
| CCR5 | chemokine (C-C motif) receptor 5 (gene/pseudogene) | 6.71E+02 | 6.80E+01 | 8.85E+02 | 1.11E+02 | 3.41E+02 | 5.53E+00 |
| HLA-DMB | major histocompatibility complex, class II, DM beta | 6.44E+02 | 6.31E+01 | 6.27E+02 | 3.54E+01 | 3.36E+02 | 2.72E+01 |
| PDCD1 | programmed cell death 1 | 9.39E+01 | 6.60E+00 | 5.57E+01 | 6.49E+00 | 9.31E+01 | 1.94E+01 |
| ITGB1 | integrin, beta 1 (fibronectin receptor, beta polypeptide, antigen CD29 includes MDF2, MSK12) | 1.86E+03 | 1.78E+02 | 9.18E+02 | 1.37E+02 | 5.78E+02 | 6.54E+01 |
| POLR2A | Polymerase (RNA) II (DNA directed) Polypeptide A, 220 kDa | 1.82E+03 | 2.76E+01 | 1.71E+03 | 6.81E+01 | 1.51E+03 | 3.68E+01 |
| PRDM1 | PR domain containing 1, with ZNF domain | 5.03E+03 | 3.24E+02 | 3.71E+03 | 4.64E+02 | 2.04E+03 | 2.48E+02 |
| IRF7 | interferon regulatory factor 7 | 1.06E+03 | 2.21E+02 | 1.19E+03 | 2.18E+02 | 4.31E+02 | 5.79E+01 |
| ICAM3 | intercellular adhesion molecule 3 | 4.63E+03 | 4.88E+02 | 4.57E+03 | 6.10E+02 | 2.49E+03 | 7.15E+01 |
| PSMB7 | proteasome (prosome, macropain) subunit, beta type, 7 | 3.23E+03 | 5.05E+01 | 3.26E+03 | 5.01E+01 | 3.74E+03 | 1.75E+02 |
| IL10RA | interleukin 10 receptor, alpha | 6.08E+03 | 1.38E+03 | 5.27E+03 | 7.65E+02 | 1.44E+03 | 1.24E+02 |
| CCR7 | chemokine (C-C motif) receptor 7 | 2.00E+03 | 3.36E+02 | 1.65E+03 | 1.90E+02 | 7.17E+02 | 2.95E+01 |
| TNFRSF11A | tumor necrosis factor receptor superfamily, member 11a, NFKB activator | 1.19E+03 | 1.71E+02 | 1.06E+03 | 1.69E+02 | 4.35E+02 | 4.30E+01 |
| APP | amyloid beta (A4) precursor protein | 2.89E+02 | 4.54E+01 | 3.36E+02 | 2.04E+01 | 5.72E+02 | 3.92E+01 |
| FCER1G | Fc fragment of IgE, high affinity I, receptor for; gamma polypeptide | 5.45E+02 | 2.23E+02 | 1.06E+03 | 3.08E+02 | 6.41E+01 | 1.10E+01 |
| IRF1 | interferon regulatory factor 1 | 2.70E+03 | 3.35E+02 | 1.93E+03 | 5.40E+01 | 1.04E+03 | 1.47E+02 |

TABLE 2-continued

Differentially expressed genes between expanded Tconv and Treg subsets expressing CD226 and TIGIT.*

| | | | | | | | |
|---|---|---|---|---|---|---|---|
| B2M | beta-2-microglobulin | 3.18E+05 | 6.29E+04 | 2.81E+05 | 2.73E+04 | 1.41E+05 | 8.94E+02 |
| NOD2 | nucleotide-binding oligomerization domain containing 2 | 4.93E+01 | 2.55E+00 | 3.56E+01 | 2.47E+00 | 3.49E+01 | 5.05E+00 |
| ITGA4 | integrin, alpha 4 (antigen CD49D, alpha 4 subunit of VLA-4 receptor) | 1.52E+03 | 2.24E+02 | 1.62E+03 | 1.40E+02 | 2.62E+03 | 1.20E+02 |
| MAP4K4 | mitogen-activated protein kinase kinase kinase kinase 4 | 3.21E+03 | 6.34E+02 | 2.76E+03 | 2.23E+02 | 1.27E+03 | 1.38E+02 |
| TNF | tumor necrosis factor | 1.17E+02 | 2.53E+00 | 1.13E+02 | 6.05E+00 | 6.92E+01 | 6.88E+00 |
| TAPBP | TAP binding protein (tapasin) | 3.49E+03 | 3.24E+02 | 2.75E+03 | 1.72E+02 | 2.02E+03 | 9.10E+01 |
| TNFRSF9 | tumor necrosis factor receptor superfamily, member 9 | 8.74E+02 | 4.65E+01 | 8.21E+02 | 1.50E+02 | 3.21E+02 | 7.29E+01 |
| LILRB4 | leukocyte immunoglobulin-like receptor, subfamily B (with TM and ITIM domains), member 4 | 1.12E+01 | 5.32E+00 | 2.12E+01 | 9.93E−01 | 4.60E+01 | 1.63E+01 |
| PPARG | peroxisome proliferator-activated receptor gamma | 5.17E+01 | 4.33E+00 | 2.38E+01 | 3.47E+00 | 4.32E+01 | 3.94E+00 |
| RARRES3 | retinoic acid receptor responder (tazarotene induced) 3 | 9.41E+02 | 1.53E+02 | 1.15E+03 | 1.03E+02 | 6.25E+02 | 3.98E+01 |
| CXCR3 | chemokine (C—X—C motif) receptor 3 | 2.27E+03 | 4.13E+02 | 2.54E+03 | 5.20E+02 | 4.59E+02 | 7.45E+01 |
| IL2RB | interleukin 2 receptor, beta | 4.19E+03 | 2.51E+02 | 4.60E+03 | 8.86E+01 | 2.52E+03 | 3.09E+02 |
| GATA3 | GATA binding protein 3 | 1.46E+02 | 2.24E+01 | 1.26E+02 | 2.01E+01 | 1.12E+02 | 1.56E+01 |
| CFP | complement factor properdin | 1.40E+02 | 4.61E+01 | 1.55E+02 | 2.20E+01 | 5.16E+01 | 8.28E+00 |
| LY96 | lymphocyte antigen 96 | 9.00E+02 | 1.70E+02 | 6.76E+02 | 8.16E+01 | 3.35E+02 | 2.17E+01 |
| CD58 | CD58 molecule | 1.73E+03 | 1.00E+02 | 1.26E+03 | 1.27E+01 | 1.21E+03 | 6.13E+01 |
| LCK | lymphocyte-specific protein tyrosine kinase | 5.50E+03 | 7.25E+02 | 5.55E+03 | 3.76E+02 | 3.50E+03 | 1.41E+02 |
| CD5 | CD5 molecule | 4.47E+03 | 2.53E+02 | 4.31E+03 | 3.91E+02 | 2.49E+03 | 2.36E+02 |
| GZMA | granzyme A (granzyme 1, cytotoxic T-lymphocyte-associated serine esterase 3) | 1.09E+02 | 9.04E+00 | 6.84E+01 | 9.51E+00 | 6.58E+03 | 2.11E+03 |
| NFATC1 | nuclear factor of activated T-cells, cytoplasmic, calcineurin-dependent 1 | 2.25E+02 | 2.30E+01 | 2.25E+02 | 1.57E+01 | 3.38E+02 | 2.13E+01 |
| FYN | FYN oncogene related to SRC, FGR, YES | 2.83E+03 | 3.38E+02 | 2.90E+03 | 2.69E+02 | 1.55E+03 | 9.68E+01 |
| ATM | ataxia telangiectasia mutated | 1.08E+02 | 8.19E+00 | 1.12E+02 | 1.14E+01 | 6.64E+01 | 1.83E+00 |
| FCGR2C | Fc fragment of IgG, low affinity IIc, receptor for (CD32) (gene/pseudogene) | 5.16E+01 | 2.51E+00 | 5.15E+01 | 6.52E+00 | 3.14E+01 | 2.64E+00 |
| FCGRT | Fc fragment of IgG, receptor, transporter, alpha | 8.96E+01 | 1.24E+01 | 9.65E+01 | 1.27E+01 | 1.33E+02 | 1.12E+01 |
| GZMB | granzyme B (granzyme 2, cytotoxic T-lymphocyte-associated serine esterase 1) | 3.49E+02 | 3.87E+01 | 3.33E+02 | 1.83E+02 | 1.85E+04 | 3.20E+03 |
| CD3E | CD3e molecule, epsilon (CD3-TCR complex) | 6.33E+03 | 7.99E+02 | 6.28E+03 | 5.27E+02 | 3.95E+03 | 9.19E+01 |
| STAT6 | signal transducer and activator of transcription 6, interleukin-4 induced | 2.37E+03 | 3.75E+02 | 2.34E+03 | 3.24E+02 | 1.15E+03 | 8.34E+01 |
| MR1 | major histocompatibility complex, class I-related | 2.18E+02 | 5.30E+01 | 2.18E+02 | 6.75E+01 | 5.47E+02 | 6.10E+00 |
| TNFRSF8 | tumor necrosis factor receptor superfamily, member 8 | 5.06E+02 | 1.13E+02 | 3.46E+02 | 7.13E+01 | 7.91E+02 | 3.87E+01 |
| MAPK11 | mitogen-activated protein kinase 11 | 1.11E+02 | 1.49E+01 | 1.11E+02 | 8.40E+00 | 9.70E+01 | 3.05E+00 |
| TLR3 | toll-like receptor 3 | 6.64E+01 | 9.66E+00 | 6.36E+01 | 6.65E+00 | 3.20E+01 | 1.71E+00 |
| JAK1 | Janus kinase 1 | 3.43E+03 | 5.05E+02 | 3.22E+03 | 2.73E+02 | 1.90E+03 | 1.87E+01 |
| IFIT2 | interferon-induced protein with tetratricopeptide repeats 2 | 1.96E+02 | 5.39E+01 | 2.40E+02 | 6.61E+01 | 1.57E+02 | 3.29E+01 |
| CASP2 | caspase 2, apoptosis-related cysteine peptidase | 1.06E+03 | 5.13E+01 | 1.01E+03 | 5.98E+01 | 1.44E+03 | 6.24E+01 |

TABLE 2-continued

Differentially expressed genes between expanded Tconv and Treg subsets expressing CD226 and TIGIT.*

| | | | | | | | |
|---|---|---|---|---|---|---|---|
| TIRAP | toll-interleukin 1 receptor (TIR) domain containing adaptor protein | 1.09E+02 | 1.66E+01 | 1.14E+02 | 9.15E+00 | 6.65E+01 | 4.06E+00 |
| RORC | RAR-related orphan receptor C | 8.03E+01 | 7.88E+00 | 6.09E+01 | 8.82E+00 | 3.62E+01 | 2.01E+00 |
| RELA | v-rel avian reticuloendotheliosis viral oncogene homolog A | 6.77E+02 | 2.24E+01 | 6.65E+02 | 1.07E+01 | 5.28E+02 | 2.25E+01 |
| PSMB8 | proteasome (prosome, macropain) subunit, beta type, 8 | 1.13E+04 | 1.32E+02 | 9.74E+03 | 3.38E+02 | 1.02E+04 | 2.55E+02 |
| CD83 | CD83 molecule | 3.92E+02 | 3.83E+01 | 3.43E+02 | 2.34E+01 | 2.07E+02 | 3.51E+01 |
| FCGR3A | Fc fragment of IgG, low affinity IIIa, receptor (CD16a) | 1.00E+02 | 2.15E+01 | 9.85E+01 | 6.17E+00 | 5.83E+01 | 4.12E+00 |
| TNFSF11 | tumor necrosis factor (ligand) superfamily, member 11 | 5.20E+01 | 1.05E+01 | 4.76E+01 | 2.74E+00 | 1.30E+02 | 1.77E+01 |
| HLA-DRB3 | major histocompatibility complex, class II, DR beta 3 | 3.17E+03 | 5.10E+02 | 2.96E+03 | 4.46E+02 | 1.75E+03 | 2.03E+01 |
| ENTPD1 | ectonucleoside triphosphate diphosphohydrolase 1 | 4.30E+01 | 5.00E+00 | 3.03E+01 | 7.49E+00 | 1.46E+01 | 1.26E+00 |
| TNFSF15 | tumor necrosis factor (ligand) superfamily, member 15 | 7.24E+01 | 4.27E+00 | 7.82E+01 | 8.19E+00 | 5.18E+01 | 9.04E−01 |
| IFNAR2 | interferon (alpha, beta and omega) receptor 2 | 2.78E+03 | 5.90E+02 | 2.37E+03 | 3.23E+02 | 1.06E+03 | 4.90E+01 |

*Tconv (CD4$^+$CD127$^+$) and Tregs (CD4$^+$CD25$^+$CD127$^-$) subdivided by CD226 and TIGIT population were FAC sorted then expanded for 14 days in vitro. The expression profile of the expansion product was analyzed by the nCounter.

Figure 3A:
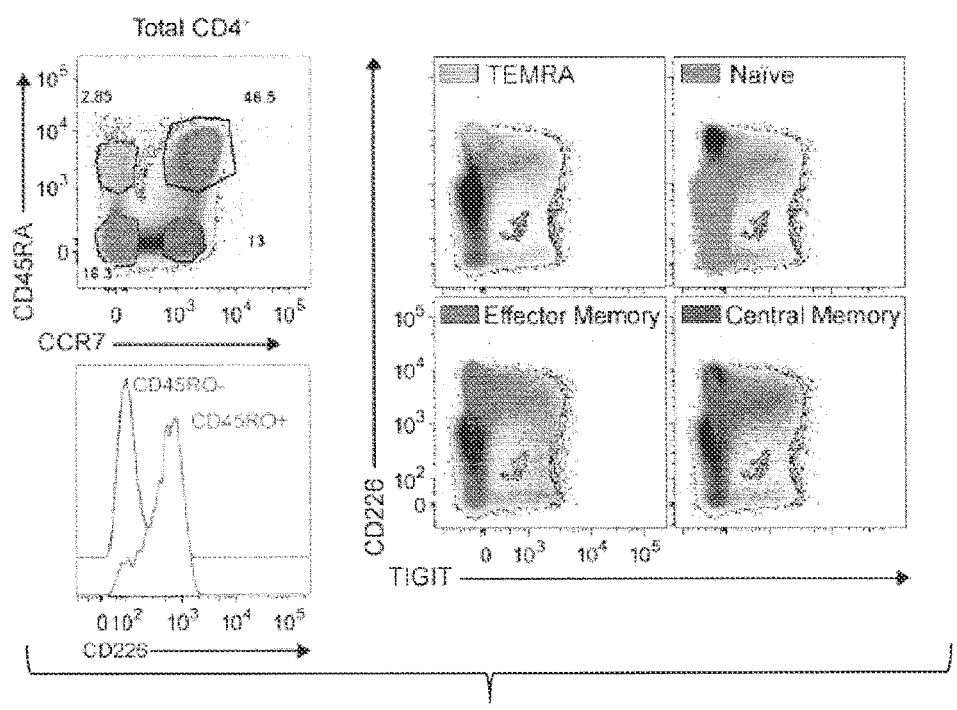
FIGS. 3A-3G. High CD226 expression is associated with a memory CD4$^+$ T cell phenotype. Cryopreserved PBMCs were thawed and stained for CD4, CCR7, CD45RA, CD45RO, CD226, and TIGIT or stimulated with PMA/ionomycin in the presence of monesin followed by intracellular staining of IFN□. (A) A representative plot shows gated viable CD4$^+$ naïve T cells (orange), central memory (dark blue), effector memory (green), and T effector memory CD45RA$^+$ (TEMRA) (cyan) populations and their TIGIT/CD226 expression compared to total CD$^+$ T cells. A representative overlaid histogram shows CD226 expression on CD4$^+$ T cells as a function of CD45RO expression. (B) Data from six subjects are summarized for frequency, CD226 gMFI, and percent TIGIT$^+$ for each subset. (C) Cryopreserved PBMCs were thawed and stained for CD4, CD226, TIGIT, and the subset specific chemokine receptors CCR4 ($T_H2$), CCR6 ($T_H17$), and CXCR3 ($T_H1$). (D) Data from four subjects are summarized for Tregs (CD4$^+$CD25$^+$CD127$^{-/lo}$) and Tconv (non-Tregs) and bifurcated by chemokine receptor expression. (E) Representative plots demonstrate that IFNγ$^+$ cells are predominantly CD226$^{hi}$ (left plot) and are less frequent in TIGIT$^+$ cells (right plot). (F) Summarized data of six subjects show CD226 and TIGIT expression on IFNγ$^+$ populations. (G) Cytokine capture assays allowed the isolation of Treg and Tconv subsets based on IFNγ production capacity. Expanded cells were restimulated with PMA/Ionomycin and analyzed by microarray (N=5). IFNγ$^+$ and IFNγ$^-$ Tregs expanded into two distinct populations that could be distinguished from Tconv as shown by PCA analysis.
Figure 3B:
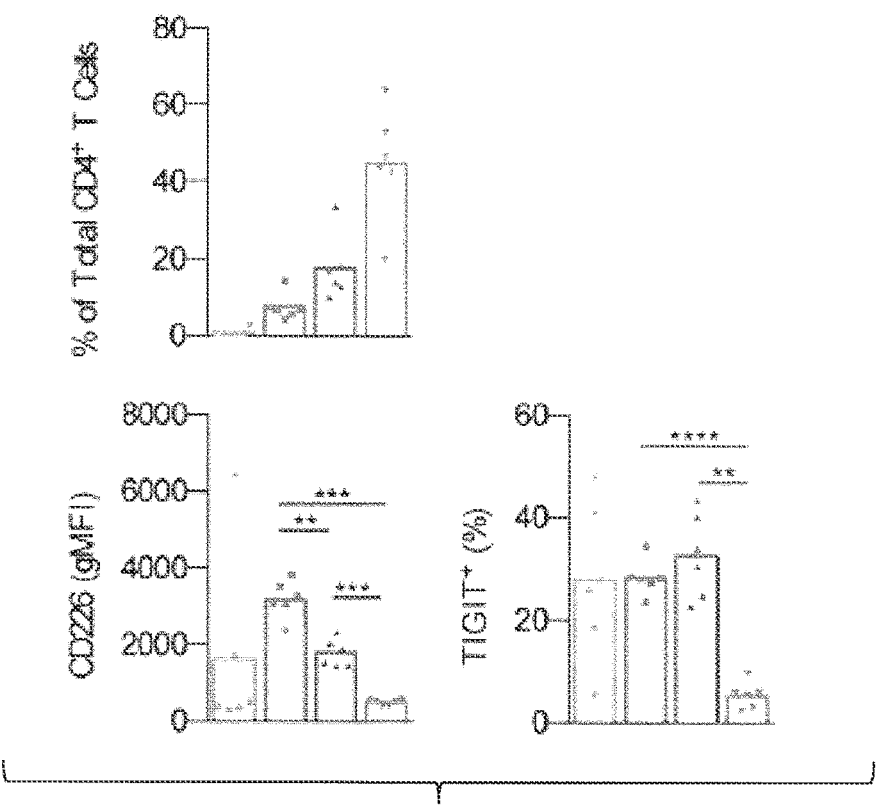

Example 2—Differentiated T Cells Concomitantly Express High CD226 and Chemokine Receptors Signaling through CD226 suppresses $T_H2$ differentiation and promotes $T_H1$ responses and IFNγ secretion. The cellular distribution and expression profiles of CD226 and TIGIT on human naïve, central and effector memory, and effector CD45RA$^+$ (TEMRA) subsets (FIG. 3A) were studied. While naïve T cells were the most abundant population (mean±SEM, 44.8%±14.6), they expressed the lowest surface levels of CD226 (495.4±73.5 gMFI), when compared to effector memory ($T_{EM}$) and central memory ($T_{CM}$) subsets (1785±357.2 and 3185±492.6, respectively)(FIG. 3B). Furthermore, the cellular distribution of CD226 in the bulk CD4$^+$ T cell population demarcates naïve (CD226$^{-/low}$) versus CD226$^{hi}$ memory subsets. Few naïve cells express TIGIT (5.3%±2.6) compared to the memory subsets (29.0%±3.5 for $T_{EM}$ and 32.7%±8.2 for $T_{CM}$). One subject with a prominent TEMRA population was CD226$^{hi}$TIGIT$^-$ (FIG. 3A), which coincides with their role as a pro-inflammatory T cell subset.

Figure 3C:
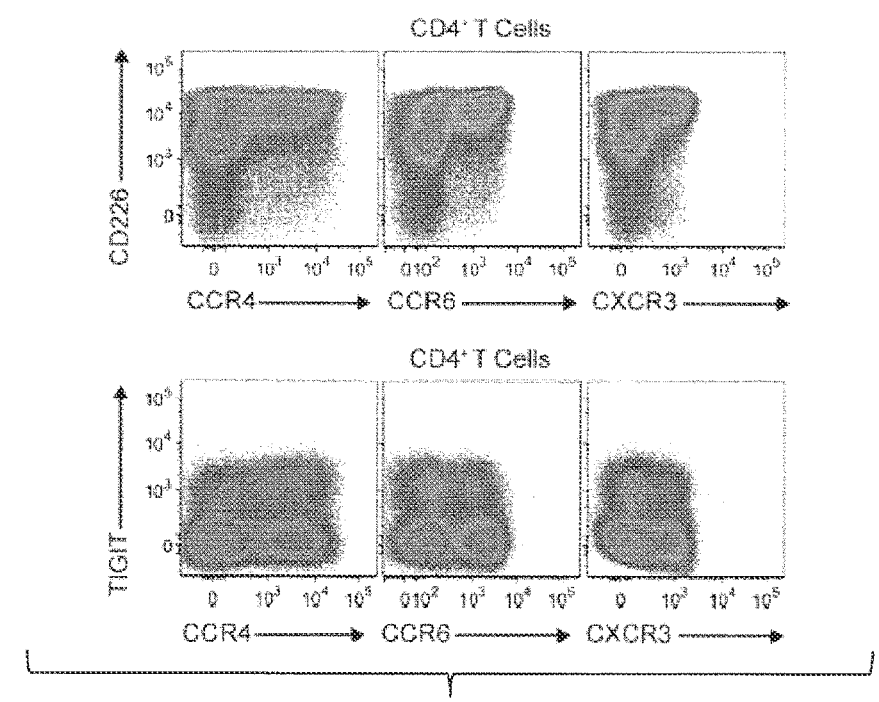
Figure 3D:
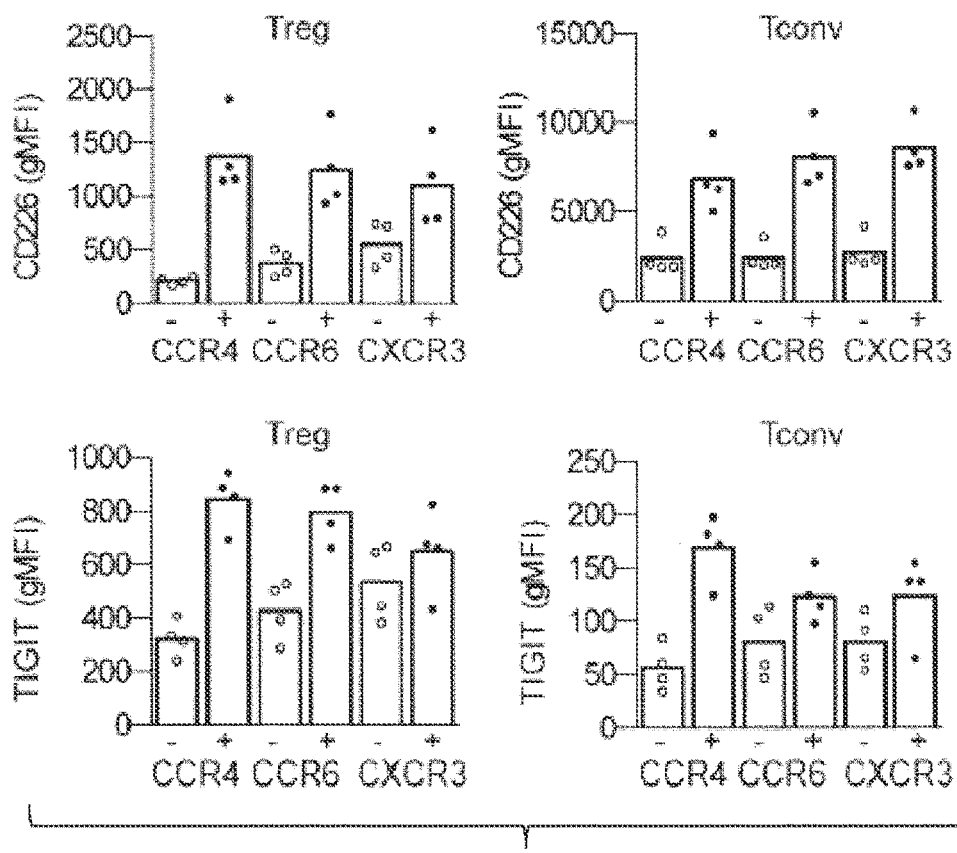

In addition to robust CD226 expression in $T_{EM}$ and $T_{CM}$, we also noted that chemokine receptors expressed by $T_H2$, $T_H17$, and $T_H1$ cells were co-expressed with high levels of CD226 (FIG. 3C; upper plots). TIGIT$^+$ populations also expressed chemokine receptors, albeit to a lesser extent than with CD226 (FIG. 3C; lower plots). Increased CD226 and TIGIT on differentiated subsets were observed for both CD4$^+$CD127$^+$ Tconv and CD4$^+$CD25$^+$CD127$^{-/low}$ Treg (FIG. 3D).

Example 3—CD226 Expression is Associated with Effector Cytokine Production

Figure 3E:
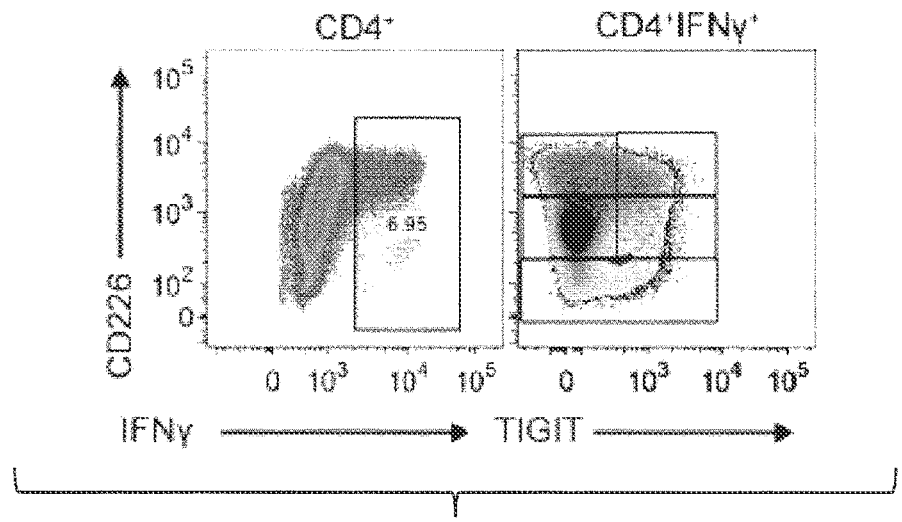
Figure 3F:
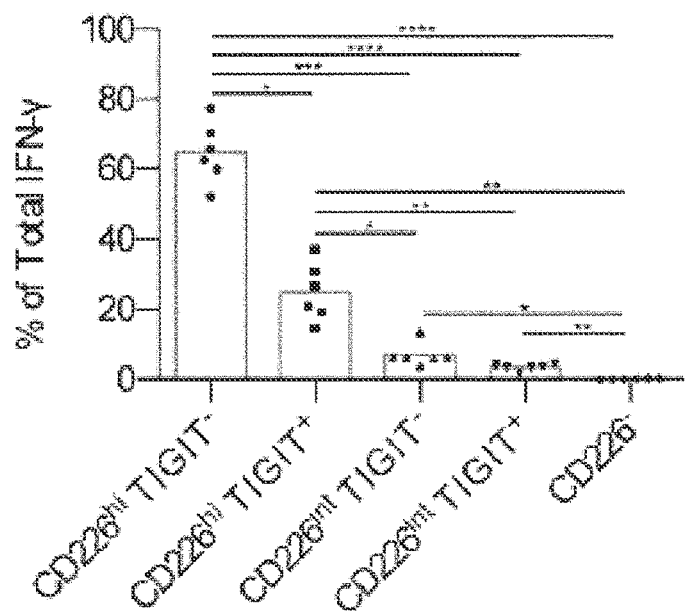

CD226 and TIGIT have opposing roles in the regulation of IFNγ. The influence of CD226 and TIGIT on IFNγ production by PBMC following activation was studied (FIG. 3E). IFNγ tracked primarily to the CD226$^{hi}$TIGIT fraction, with the CD226$^{hi}$TIGIT$^+$ population consistently containing a minor population of IFNγ$^+$ T cells (64.7%±8.7 vs. 24.9±8.3; p=0.011). IFNγ was co-expressed with CD226, as CD226$^{int}$TIGIT$^-$ and CD226$^{int}$TIGIT$^+$ populations contained significantly lower percentages of IFNγ cells than their CD226$^{hi}$ counterparts (FIG. 3F; 7.03%±3.29 and 3.42±1.03%, respectively). The CD226$^-$ subset was largely devoid of IFNγ$^+$ T cells (0.183%±0.053). Overall, these results demonstrate a close association between CD226 and the production of IFNγ by antigen-experienced T cells.

Figure 8A:
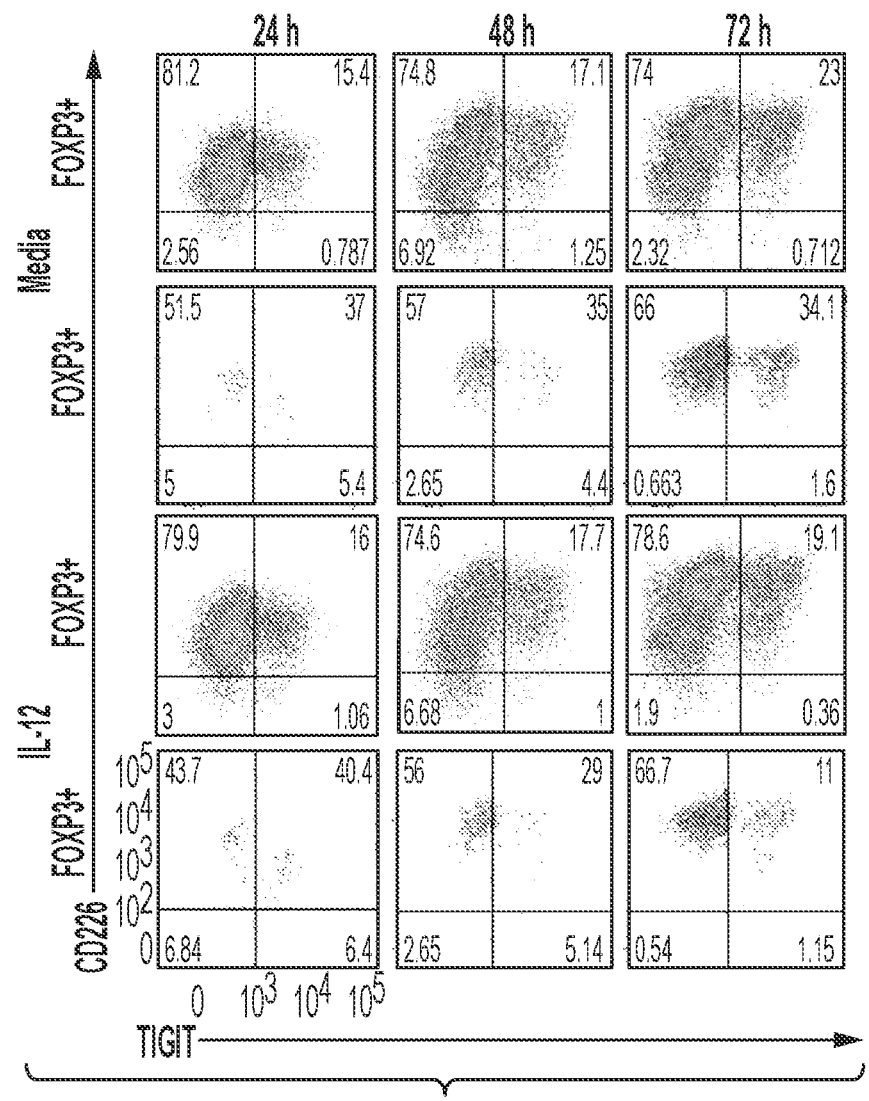
Figure 8B:
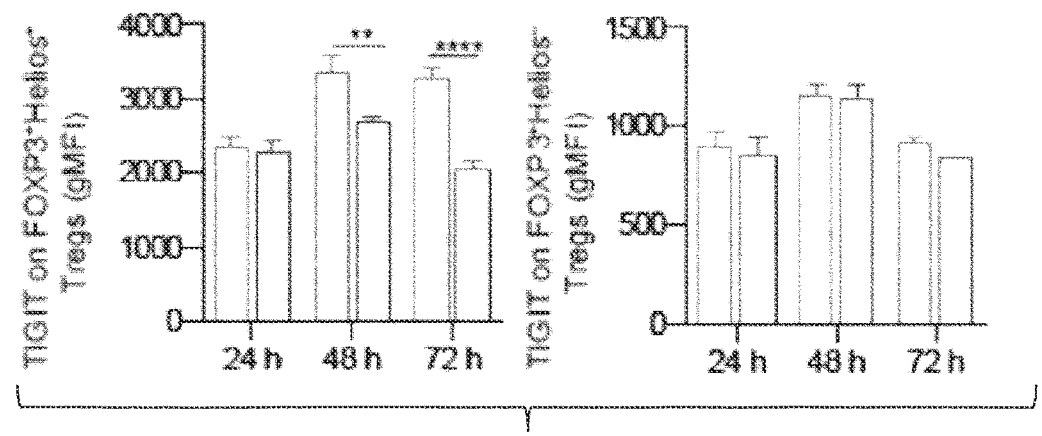

To determine if this association was influenced by $T_H1$-skewing conditions, T cells were activated in the presence of IL-12 (FIG. 8). While both CD226 and TIGIT increase upon T cell activation, the change in TIGIT expression by tTreg has not been characterized following culture with IL-12. CD226 expression increased over the 72 hr time course (FIG. 8A). Likewise, TIGIT increases following TCR activation. Notably, TIGIT upregulation was attenuated by IL-12 in FOXP3$^+$ Helios$^+$ Treg (FIG. 8B). IL-12 upregulated CD226 and IFNγ as expected (FIG. 8C-D), however, the proportion of tTreg recovered from the culture decreased in IL-12 (FIG. 1E). As such, IL-12 exposure may potentiate Teff cytokine production concomitant with a reduction in both tTreg proliferation and TIGIT expression.

Figure 3G:
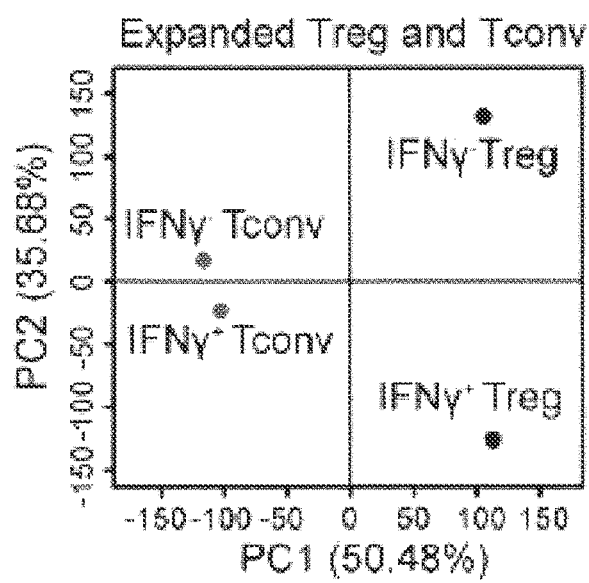
Figure 9A:
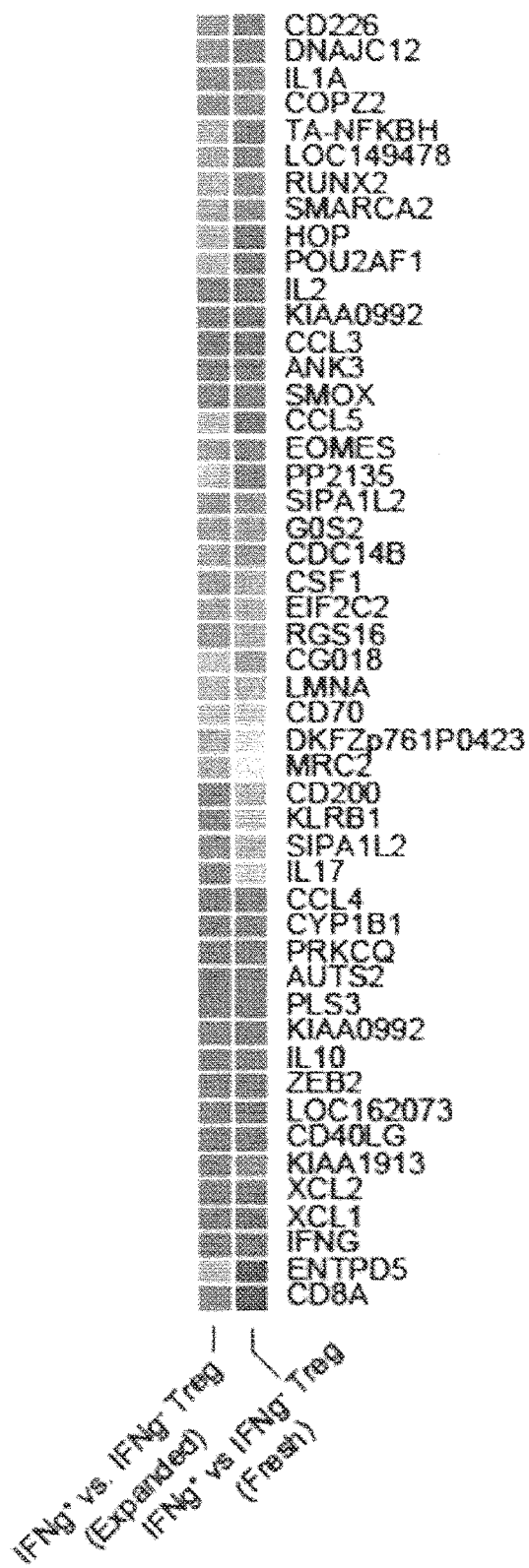
FIGS. 9A-9B. IFNγ+ Treg express elevated CD226 and reduced TIGIT. Cytokine cell capture reagent was used to isolate Treg and Tconv subsets based on their capacity to produce IFNγ. (A) Shown are the overlapping differentially expressed genes between 4 hr PMA and ionomycin activated IFNγ+ and IFNγ− Tregs immediately after FACS isolation (fresh) and following 14 d ex vivo expansion and 4 hr PMA and ionomycin reactivation (expanded). (B) Differentially expressed genes between all four populations (IFNγ+/− Treg and Tconv subsets) demonstrate that TIGIT is elevated in Treg and highly expressed in IFNγ− Treg subset (N=5).
Figure 9B:
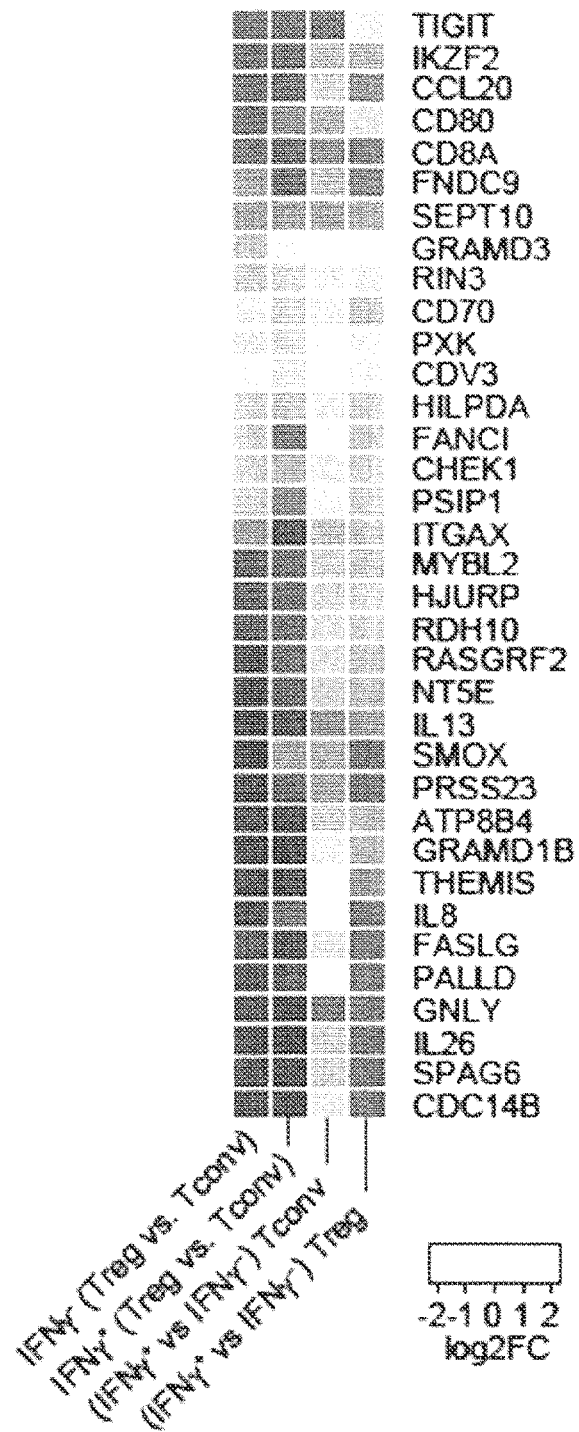

IFNγ$^+$ Treg are elevated in patients with T1D. To further characterize this subset, IFNγ$^+$ or IFNγ$^-$ Treg and Tconv subsets were isolated and a transcriptional profile of the FACS isolated subsets was conducted. Principal component analysis (PCA) indicated divergence of Treg and Tconv populations, with further discordance in IFNγ$^+$ and IFNγ$^-$ Treg (FIG. 3G). Importantly, both freshly isolated and expanded IFNγ$^-$ Treg express significantly more CD226 than the IFNγ Treg subset (FIG. 9A). Moreover, TIGIT expression was increased in IFNγ$^-$ Tregs compared to IFNγ$^+$ Tregs, while the inverse is true for Tconv (FIG. 9B).

Figure 4A:
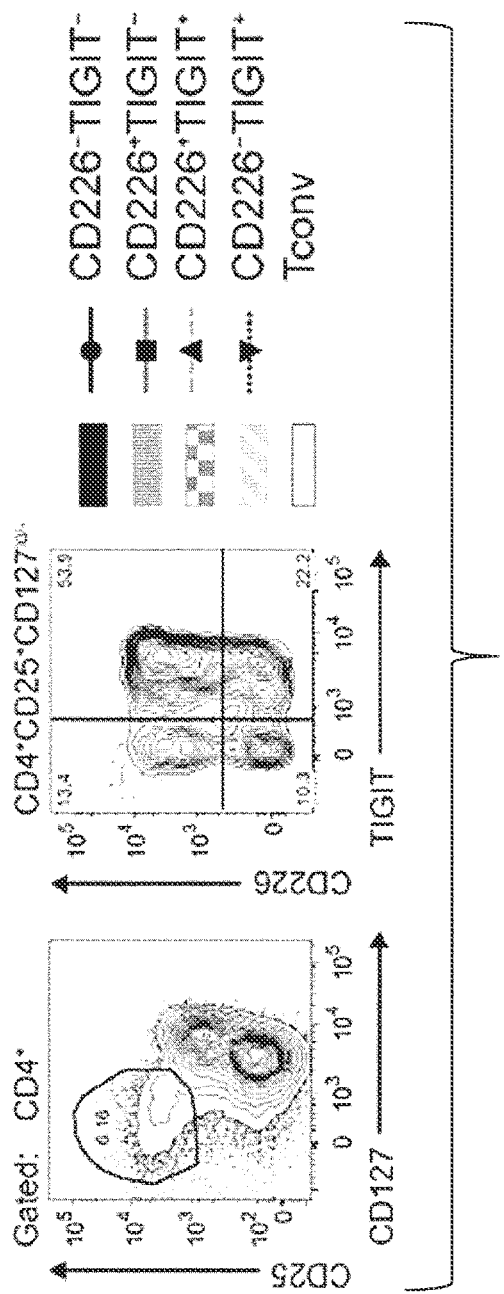

Example 4—CD226 and TIGIT Identify Functionally Distinct Subpopulations of Treg Human CD4$^+$CD25$^{hi}$CD127 Tregs contain a significant degree of heterogeneity in terms of lineage diversity and antigen exposure. CD4$^+$CD25$^{hi}$CD127 Tregs were subdivided based on CD226 and TIGIT expression (FIG. 4A, right plot). FOXP3-TSDR demethylation at the conserved non-coding sequence 2 (CNS2) has been previously associated with Treg stability. Hence, we measured the percentage of cells demethylated at the TSDR. When analyzed ex vivo, CD226$^+$ TIGIT$^-$ T cells were reduced in TSDR demethylation (30.0%±8.3), in comparison to the other Treg subsets and Tconv cells (FIG. 4B). Despite this reduction in TSDR-demethylation, the resulting population suppressed to comparable levels when compared to the other freshly isolated CD4$^+$CD25$^{hi}$CD12T Treg populations (FIG. 4C). Dye dilution analysis facilitated further analysis of Treg proliferation and viability. Increased proliferation of both the CD226$^-$ TIGIT$^-$ (naïve) and CD2226$^+$ TIGIT$^-$ populations was observed. Interestingly, increased IL-10 in the suppression assay co-culture with CD226$^+$ TIGIT$^-$ Treg was also noted. A trend toward more CD2226$^+$ TIGIT$^+$ cell death was observed; however, this did not reach statistical significance for any Treg subset. Thus, freshly isolated CD226$^+$ TIGIT$^-$ T cells exhibit comparable ex vivo suppression when freshly isolated, yet differ in FOXP3-TSDR demethylation and cytokine production.

Figure 5A:
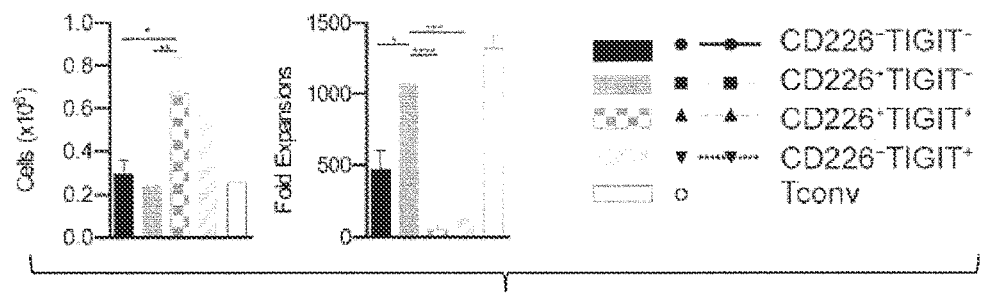
FIGS. 5A-5I. In vitro Expansion of Tregs expressing TIGIT and/or CD226 yield subpopulations differing in proliferative ability, purity, and suppressive capacity. CD4$^+$CD25$^+$CD127$^{-/lo}$ Tregs were isolated from fresh peripheral blood and further divided to yield four distinct populations based on CD226 and TIGIT expression (A) TIGIT$^+$ Tregs were refractory to expansion as the number of cells yielded on day 0 (left graph) was inversely related to fold expansion following 14 d of culture (right graph). Following expansion, cells were reactivated with PMA/ionomycin for 4 h and assessed for FOXP3 and Helios (B, C), TIGIT and CD226 (D, E), and IFNγ and CD226 (F, G). (H) The in vitro suppressive capacity of expanded Tregs was assessed. Percent suppression was calculated by division index of the CD4$^+$ or CD8$^+$ gated responder T cells in co-culture relative to responders alone. (1) Graphs indicate the percent of cells demethylated at the FOXP3-TSDR (left graph) and the correlation between FOXP3-TSDR analysis and FOXP3 and Helios expression as analyzed by FACS following 14 d cultures (right graph; $R^2$=0.94, p<0.0001). Data are represented as ±standard error of the mean (N=4).

Protocols to generate expanded human Treg are susceptible to outgrowth of non-Treg and the potential for lineage instability. Therefore, the purity and suppressive activity of Tregs was analyzed post in vitro expansion based on CD226 and TIGIT expression (FIG. 5A). While the TIGIT$^+$ fractions constituted the majority of Treg isolated from PBMC, these cells were highly refractory to expansion, limiting the overall Treg yield (FIG. 5A). This decrease in proliferative capacity of the sorted TIGIT$^+$ Treg supports the role of TIGIT as an intrinsic negative regulator, and also reflects an enrichment of antigen-experienced (CD45RO$^+$) cells with limited expansion capacity. In contrast, the TIGIT$^-$ Treg fraction expanded robustly from a naïve state.

Figure 5B:
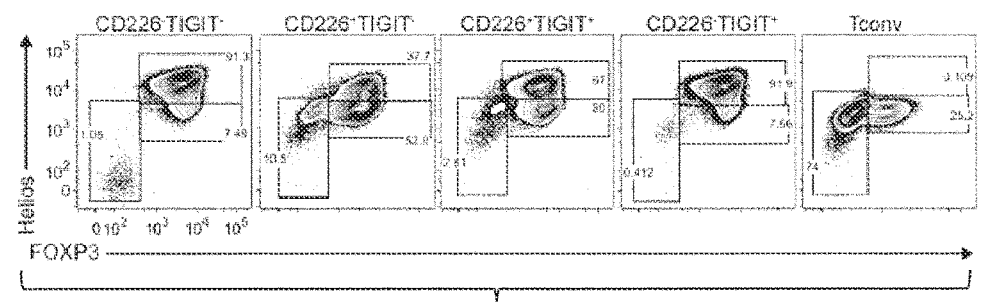
Figure 5C:
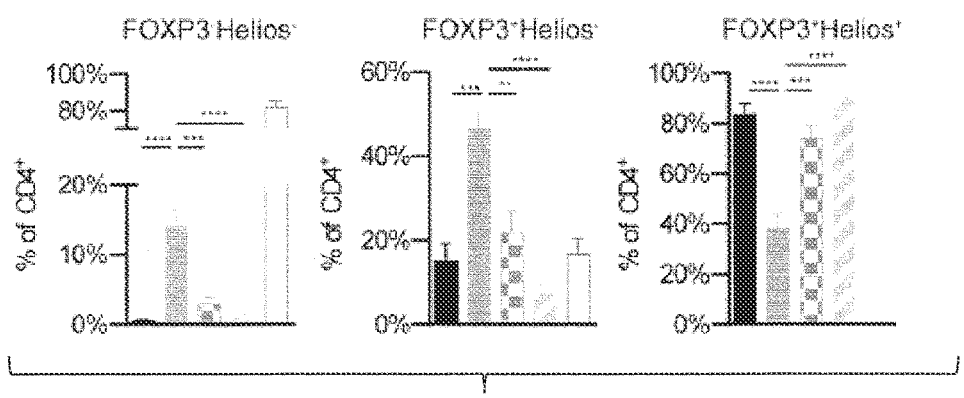
Figure 5D:
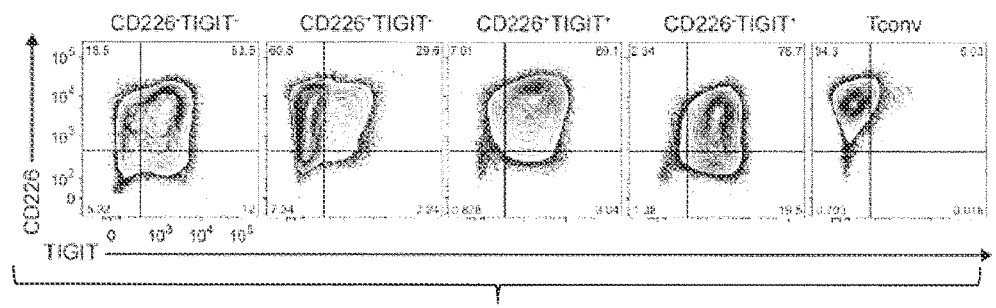
Figure 5E:
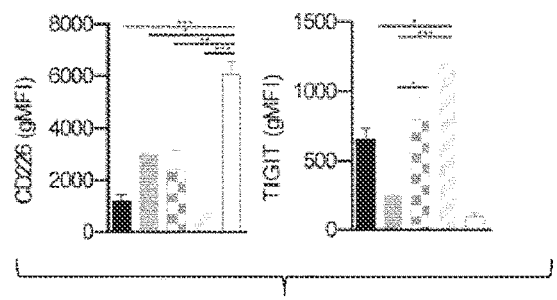

To further assess the purity and functional capacity of these subsets, FOXP3 and Helios were analyzed following expansion (FIG. 5B-C). The highest purity of post-expansion Treg originated from cells lacking CD226 expression at the time of the initial sort (i.e., prior to in vitro expansion). The highest percentage of FOXP3$^+$ Helios$^+$ cells were observed in the CD226TIGIT$^+$ population, followed by CD226$^-$ TIGIT and CD226$^+$ TIGIT$^+$ cultures (90.73%±3.7, 83.69±8.69, and 74.30±10.13, respectively). In contrast, the CD226'TIGIT population contained the least FOXP3$^+$ Helios$^+$ cells post expansion (38.18±11.70). Tconv expanded with very little FOXP3 and Helios co-expression (FIG. 5B). In terms of surface CD226 and TIGIT expression, TIGIT was maintained or upregulated on TIGIT$^+$ and TIGIT$^-$CD226$^-$ cells following expansion, but remained low on TIGIT CD226$^+$ Treg and Tconv populations (FIG. 5D-E).

Figure 5F:
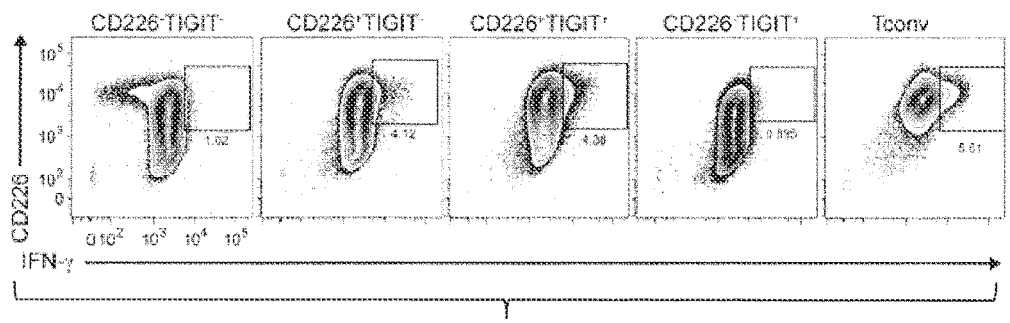
Figure 5G:
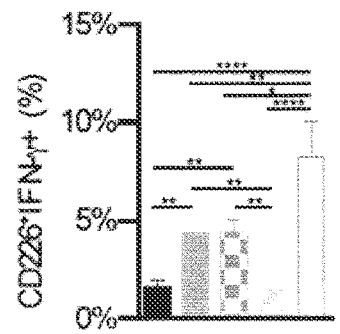
Figure 5H:
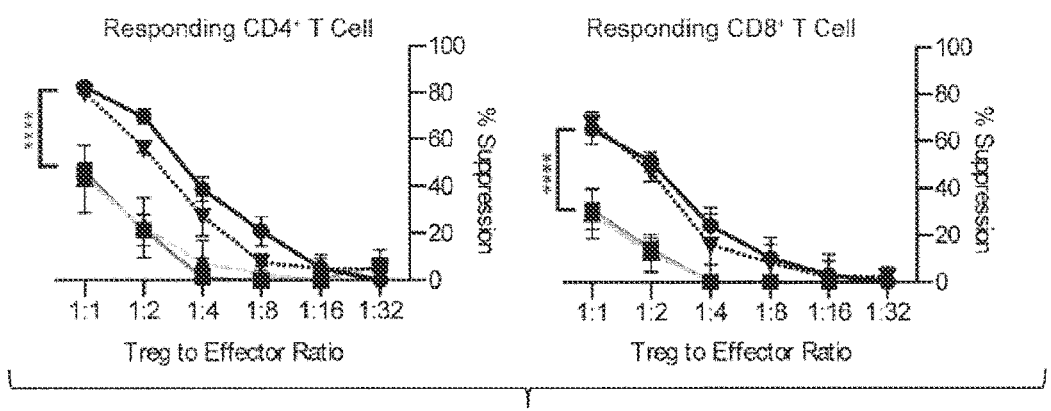

Expanded Treg from T1D subjects were enriched in FOXP3$^+$ Helios$^-$ cells with the capacity to produce IFNγ. Accordingly, CD226$^+$ Treg have increased capacity to produce IFNγ upon stimulation, while CD226$^-$ Treg were almost completely devoid of IFNγ (FIG. 5F-G). CD226$^-$ Treg (TIGIT$^+$ or TIGIT) were both able to potently suppress autologous CD4 and CD8 T cell proliferation, with some diminution observed in the CD226$^+$ expanded subset (FIG. 5H). The CD226$^-$ TIGIT$^-$ and CD226$^-$ TIGIT$^+$ subsets were almost completely demethylated at the TSDR (92.0%±3.13% and 94.5%±3.71, respectively, FIG. 5I). The degree of demethylation at the TSDR correlated strongly with FOXP3 and Helios co-expression determined by FACS (FIG. 5I; $R^2$=0.94, $p<0.0001$).

Figure 5I:
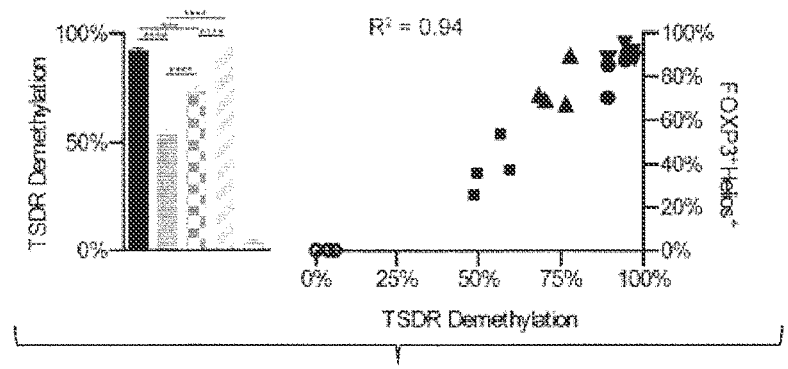
Figure 6A:
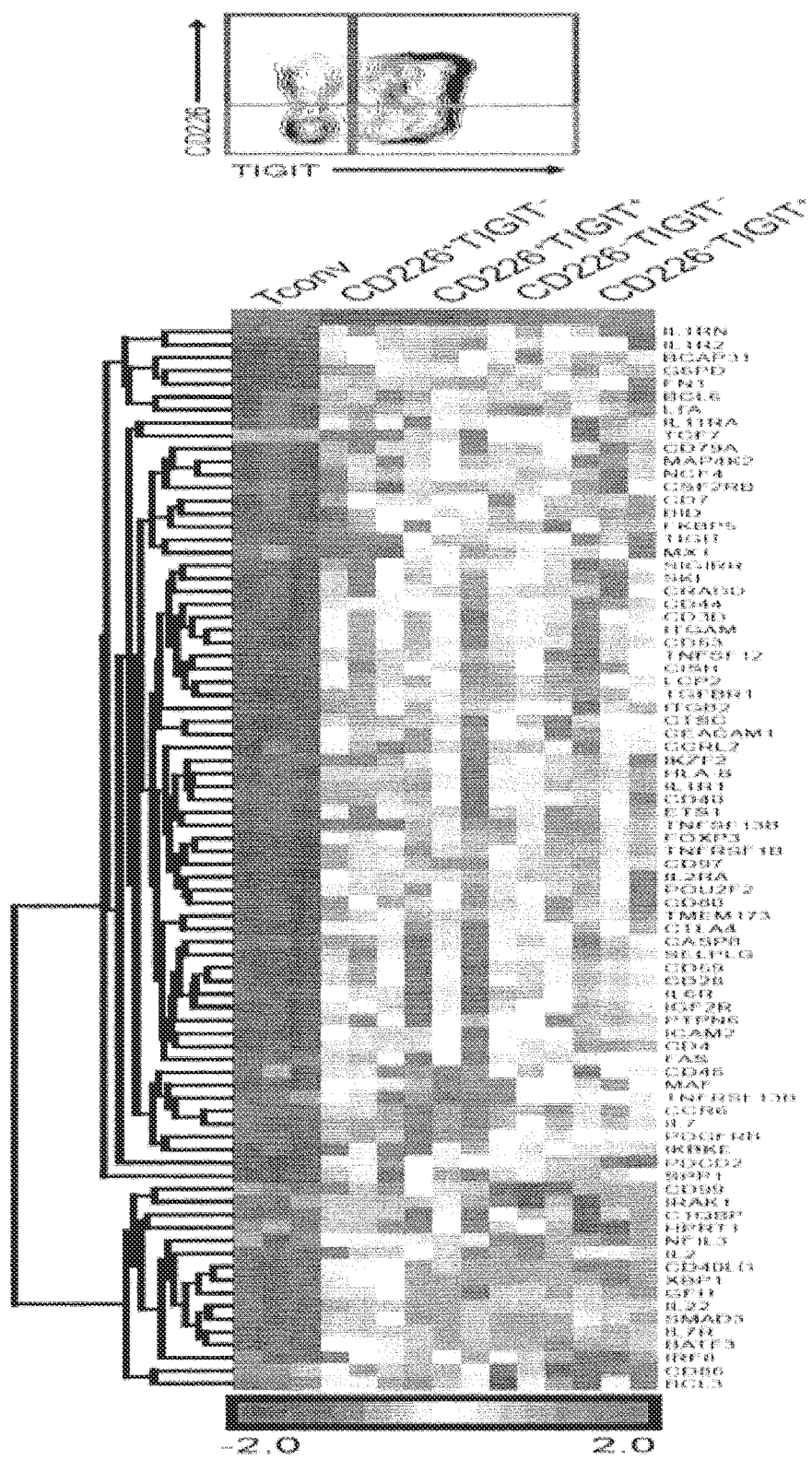
FIGS. 6A-6H. CD226$^+$ TIGIT$^-$ Tregs display an intermediate effector gene expression profile. mRNA was isolated from 14 d in vitro expanded Treg subsets and Tconv cells and analyzed for gene expression on the Human Immunology GX Panel on the NanoString platform. (A) Treg and Tconv profiles shown by hierarchical clustering based on the Euclidian distance was used to create a heatmap and dendrogram of the genes in Partek Genomic Suite. Select genes of interest are shown and grouped based on (B) coinhibitory receptors, (C) cytokines, (D) cytokine receptors or subunits, and (E) lineage-associated transcription factors. Normalized gene counts are represented as ±standard error of the mean with grey horizontal lines indicating the background expression threshold (N=3). (F) The similarity of each Treg subsets to Tconv cells was shown by PCA analysis. (G-H) Fresh Treg subsets sorted according to CD226 and TIGIT expression were activated by CD3/28 dynabeads for 24, 48, and 72 hrs. (G) Cytokine production was tested by multiplex assay and shown by bar graph and (H) heatmap for 72 hrs. Data are represented as ±standard error of the mean (N=4).
Figure 6B:
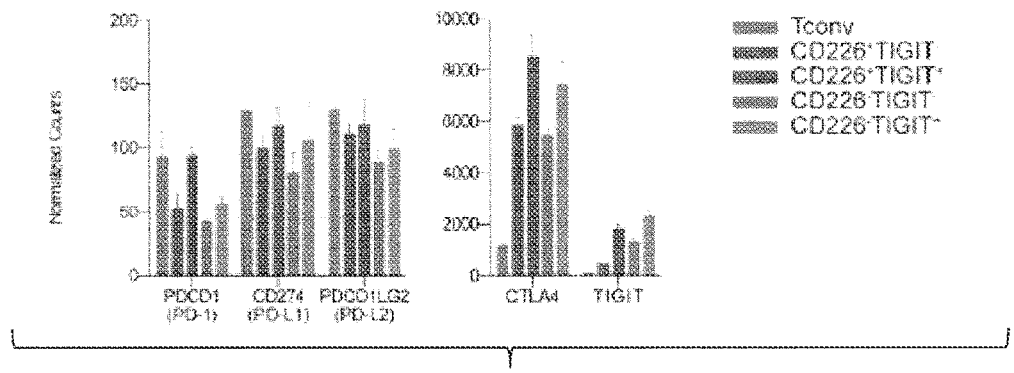
Figure 6C:
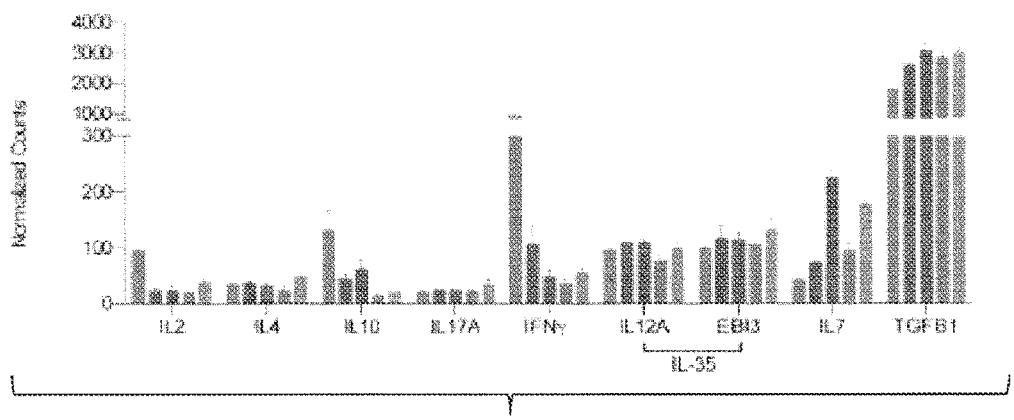
Figure 6D:
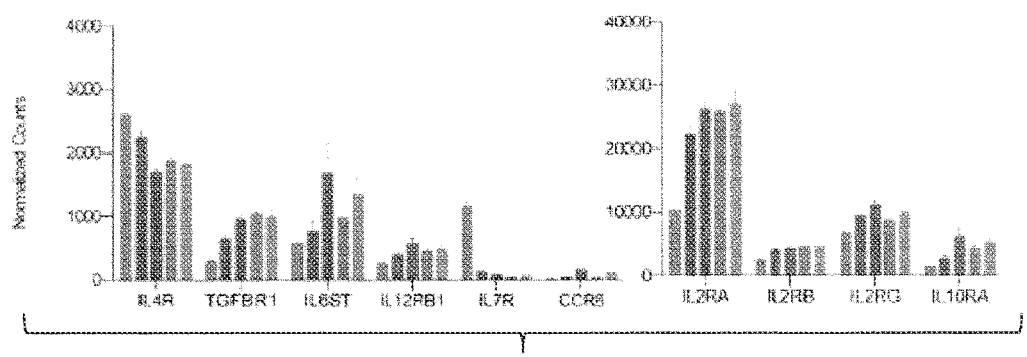
Figure 6E:
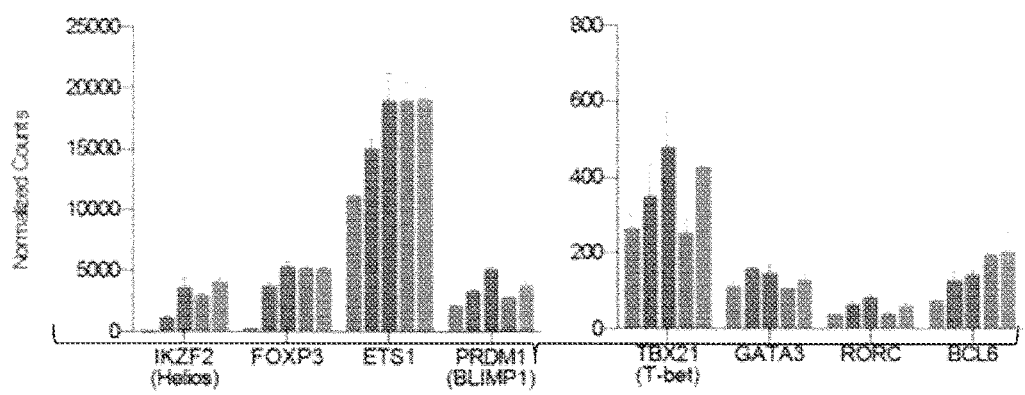
Figure 6F:
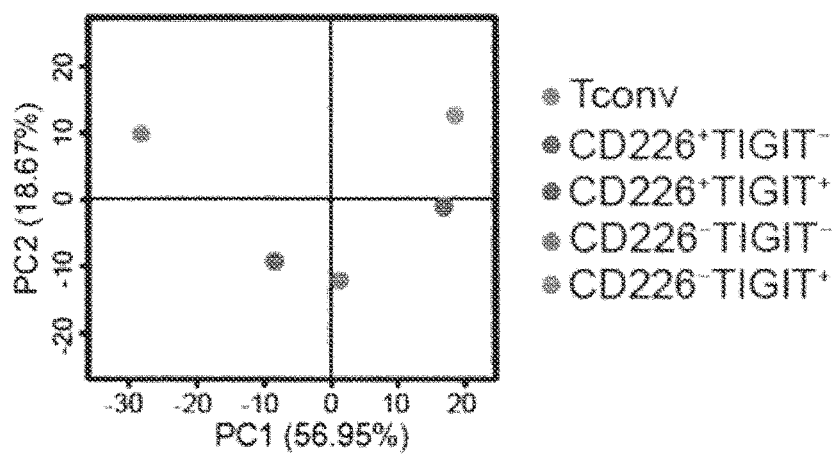
Figure 6G:
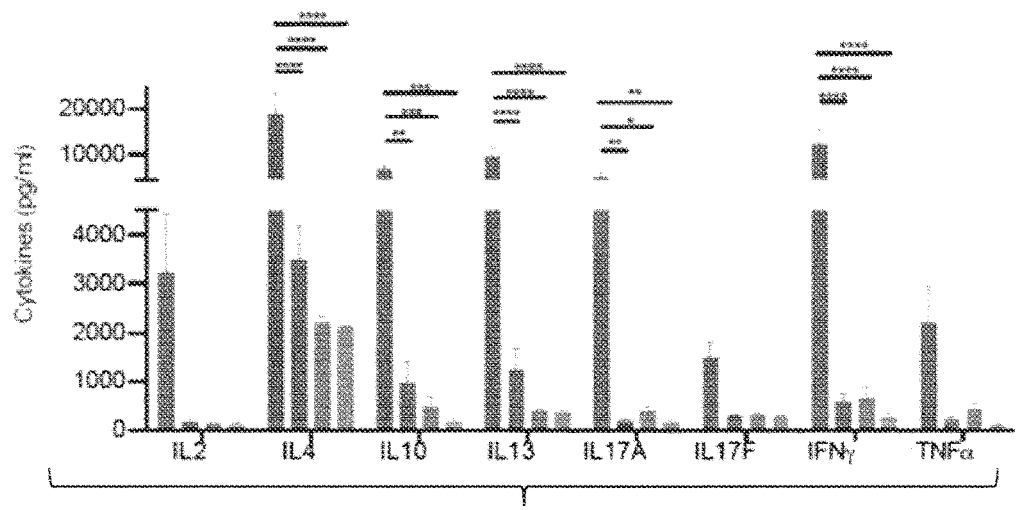
Figure 6H:
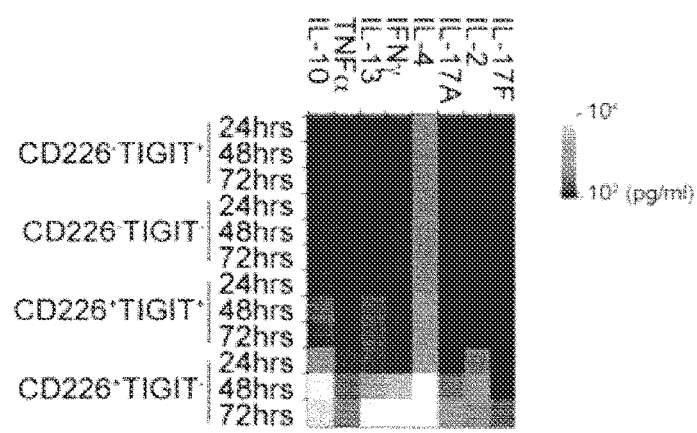

Example 5—CD226$^+$ TIGIT$^-$ T Cells Express an Activated Effector Gene Expression Profile and Produce IL-10 and Effector Cytokines Gene expression profiles provide a powerful signature of the regulatory and effector mechanisms employed by T cells. Given that most Treg therapies will require some form of expansion, a gene profile was conducted on in vitro expanded Tconv (CD4$^+$CD25$^-$CD127$^+$) or Treg (CD4$^+$CD25$^+$CD127$^{-/lo}$) that were further sub-divided based on initial TIGIT and CD226 expression (FIG. 6A). From this analysis, 159 genes were found differentially expressed between the groups ($p<0.05$). These data are summarized in the heatmap and dendogram (FIG. 6A and Table 2). The normalized transcript counts were used to cluster the genes. 18.6% of the variance observed was attributable to individual subject variance, while the remainder segregated based on the initial sorted populations. Tconv showed a clear demarcation from Treg, with the CD226$^+$ TIGIT$^-$ population demonstrating an intermediate expression profile between Treg and Tconv (FIG. 6A, green bars). Interestingly, the CD226$^+$ TIGIT$^+$ population has a Treg signature highly enriched in negative regulators and immunoregulatory pathways (FIG. 6B-E). Despite this regulatory signature, it did not completely correlate with their suppressive capacity following in vitro expansion (FIG. 5H). This may imply that CD226 negatively impacts suppression, or may reflect a preferential outgrowth of non-Treg by d14, as indicated by the TSDR results (FIG. 5I). PCA analysis of Treg subsets demonstrated the CD226$^+$ TIGIT$^-$ population shared some common features with Tconv cells (FIG. 6F). An extensive multiplex cytokine profile of freshly isolated Tregs further confirmed the capacity of CD226$^+$ TIGIT$^-$ T cells to produce a broad array of cytokines (FIG. 6G-H).

Figure 7A:
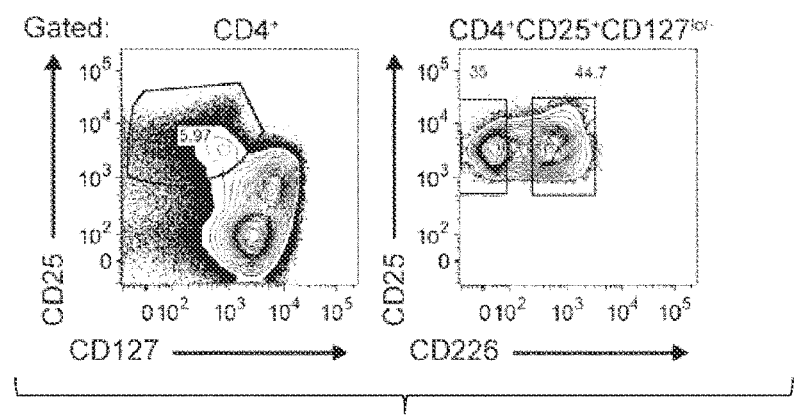
Figure 7B:
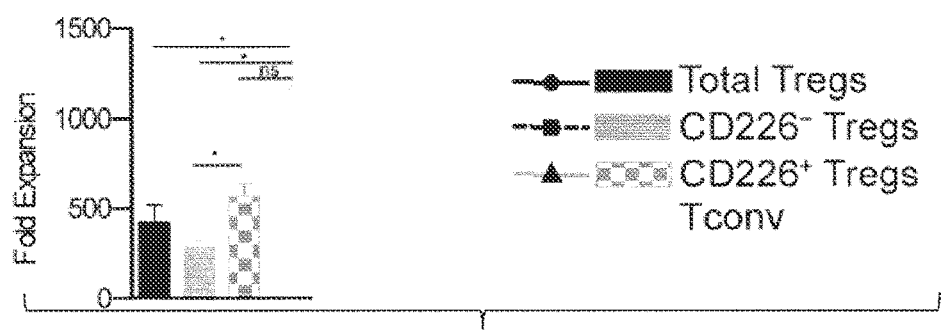
Figure 7C:
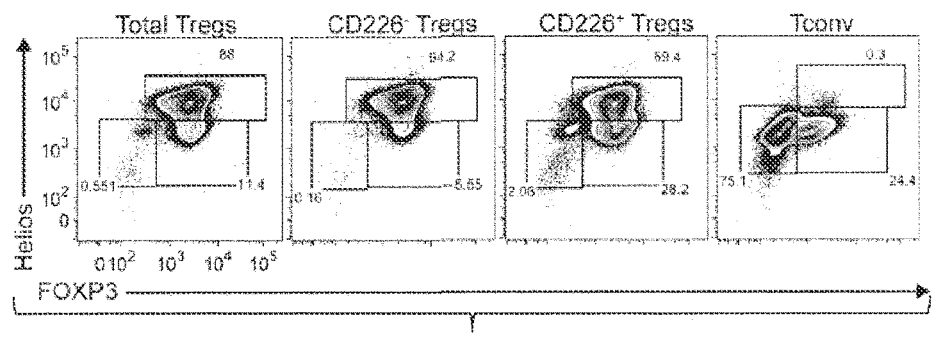
Figure 7I:
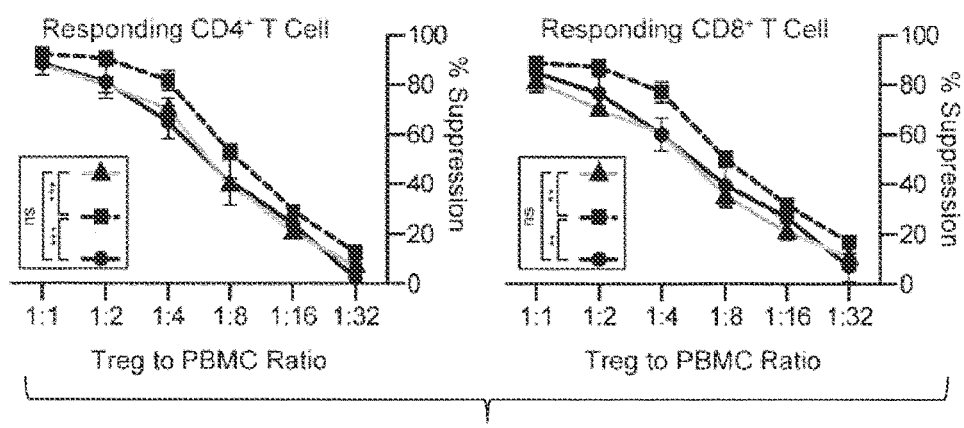
Figure 7J:
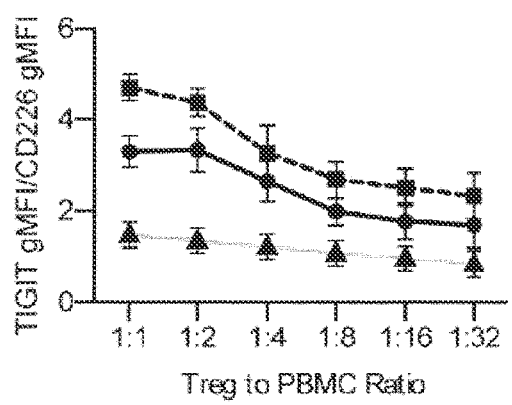
Figure 7K:
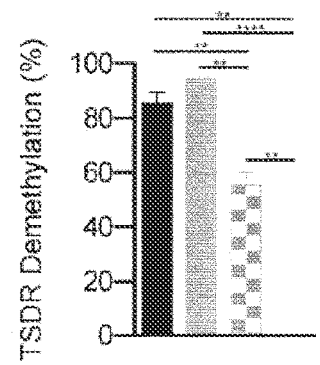

Example 6—Exclusion of CD226$^+$ Eliminates Unstable Treg Following In Vitro Expansion Improving Treg stability and limiting contamination non-tTreg may be critical for future Treg therapies. Prior efforts demonstrated that CD226 expression, irrespective of initial TIGIT expression, resulted in a sizable fraction of cells that were reduced in suppressive activity and methylated at the TSDR (FIG. 5). In addition, the TIGIT$^+$ population was highly refractory to expansion. Thus, eliminating CD226$^+$ cells during the initial sort would increase purity without significantly constraining the final cell yield (FIG. 7A). Total Treg and CD226$^-$ Treg expanded with comparable kinetics (FIG. 7B). Importantly, the purity of the Treg subsets (FOXP3$^+$ Helios$^+$) was consistently higher in the CD226$^-$ Treg subset compared to the CD226$^+$ Treg fraction (89.33±3.45 vs. 57.2±5.96, respectively) (FIG. 7C-D). CD226 expression correlated with IFNγ (FIG. 7E-F). This observation was inversely related to TIGIT expression following culture (FIG. 7G,H). In terms of suppressive capacity, CD226$^-$ Treg were consistently more able to suppress CD4$^+$ and CD8$^+$ responder T cells than their CD226$^-$ Treg counterparts (FIG. 7I). Indeed, an elevated ratio of TIGIT to CD226 expression on the tTreg population following an in vitro suppression assay was associated with increased suppressive activity and TSDR demethylation (FIG. 7I-K).

These results suggest that elimination of cells expressing CD226 provides an effective means to further enrich a stable population of human Treg.

Example 7—Identification of Treg Based on TIGIT and CD226 Expression

Prior efforts to define the transcriptional profile of human Treg have relied primarily upon the use of surrogate surface markers for isolation. This methodology is subject to alterations in surface marker expression following antigen exposure and cellular activation (particularly for CD45RA, CD25, and CD127). A direct transcriptional profile of Treg by FACS sorting cells based on the transcription factors FOXP3 and Helios was conducted. This analysis identified TIGIT, an important negative regulator, as highly expressed on tTreg relative to Tconv or FOXP3$^+$ Helios$^-$ T cells.

TIGIT expression on Treg was characterized in the context of the competing costimulatory molecule CD226. This analysis identified four distinct subpopulations of cells based on their surface expression of these receptors. CD226 expression marks both $T_{CM}$ and $T_{EM}$ and Treg subsets capable of producing IFNγ and IL-10 for Treg. TIGIT expression was stable or upregulated on Treg following in vitro expansion. An incipient concept in Treg biology relates to the ability of Treg to co-opt the transcription programs of the $T_H$ cells they are posed with suppressing (e.g., Tbet$^+$ Treg suppress $T_H1$ immunity, $T_H2$-Treg suppress humoral responses, etc.). This may also be the case for antigen-experienced Treg that are CD226$^+$ TIGIT$^+$. Lineage associated chemokine receptor expression on both CD226 and TIGIT expressing Treg is noted.

TIGIT$^+$CD226$^-$ Treg expressed high levels of FOXP3 and Helios and were demethylated at the TSDR. Moreover, data from in vitro suppression assays indicated TIGIT expression on Treg was associated with robust suppressive activity. The relative ratio of these receptors might provide an informative biomarker. These findings are particularly timely given the genetic associations of CD226 in autoimmune diseases and multiple reports of Treg functional defects and effector cytokine production by Treg (e.g., IFNγ and IL-17). Interestingly, analysis of IL-10 producing T regulatory-type 1 ($T_R1$) cells also reported high CD226 expression, in addition to CD49b and LAG3.

These findings for TIGIT$^+$ Treg draw some distinctions from those recently reported by Joller et al., who suggested TIGIT$^+$ Treg share features with T cells of a proinflammatory lineage. This phenotype may be more representative of cells co-expressing CD226 and TIGIT, as few cytokines or effector genes were upregulated in TIGIT single positive populations. In fact, IL-10 expression and the IL-10-associated transactivator PRDM1 were only discernible in the CD226$^+$ TIGIT$^+$ Treg population. Moreover, the shift toward an effector-like lineage was most prominent in the CD226$^+$ TIGIT$^-$ population.

Example 8—Immunotherapies Using CD226$^-$ Treg

Immunotherapeutics targeting coinhibitory molecules such as CTLA-4 and PD-1 have garnered increasing interest following notable clinical successes. This disclosure provides important implications for future therapies that may seek to target the CD226/TIGIT axis. CD226 is associated with proinflammatory Teff and this disclosure demonstrate CD226 is also expressed at low to intermediate levels on naïve T cells and may play a key role in IL-10 producing Treg. Moreover, CD226 is upregulated on the majority of tTreg following activation. Thus, therapies seeking to block CD226 to attenuate Teff activity must be carefully dosed to target CD226$^{hi}$ expressing Teff, while preserving naïve T cells and IL-10 producing $T_R1$. The CD226/TIGIT axis may be susceptible to control by innate inflammatory cytokines, as demonstrated for IL-12. One potential benefit of anti-IL-1 2 antibody therapy may be the preservation of TIGIT expression on tTreg. Finally, the disclosure provides implications for Treg adoptive cell therapies that are currently progressing in clinical trials for a number of autoimmune conditions. Overall, the disclosure supports that CD4$^+$ CD25$^+$CD127$^{-/lo}$ Tregs maintain a high degree of purity following expansion over a period of 14 d. Extending these findings, the selection of the TIGIT$^+$ Treg population is shown to result in a highly enriched population, but this came at the cost of initial Treg recovery and resulted in a highly refractory population limiting the overall yield. However, the isolation of CD226$^-$ Treg, irrespective of initial TIGIT expression, results in a highly pure and potent population of TIGIT$^+$ Treg for use in cell therapies. Therefore, these data provide a biological context in which the autoimmune candidate gene CD226 may modulate T cell biology. Moreover, this disclosure provides markers to identify highly suppressive Treg for use in cell therapies.

Example 9—Immunotherapy of T1D Using CD226$^-$ Treg

Figure 10:
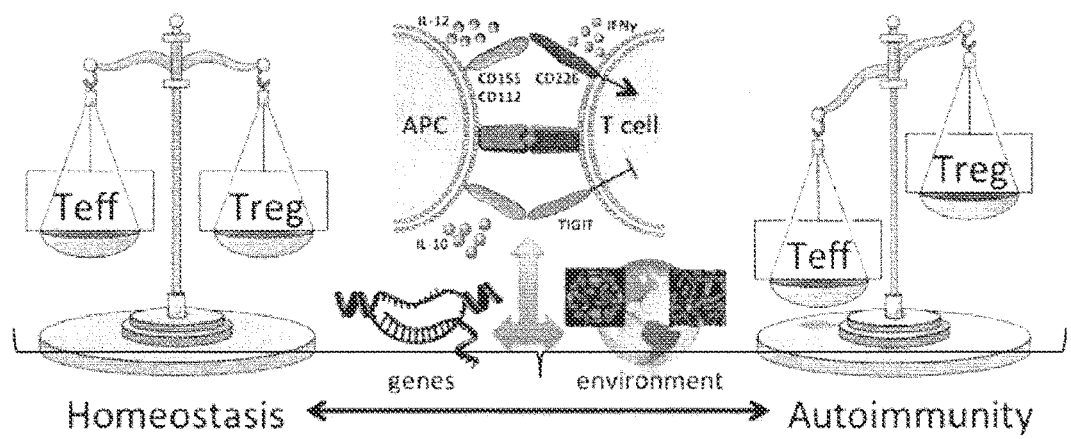
FIG. 10. Model depicting CD226 and TIGIT signaling as key checkpoint impacting immune regulation in type 1 diabetes (T1D).

T1D is a disorder of failed immune regulation. The immune system has evolved multiple mechanisms to elicit protective immunity to foreign agents while preserving tolerance to self. Treg play a central role in limiting self-reactive T cells that escape negative selection, thereby maintaining dominant peripheral tolerance to self-antigens. This regulatory pathway fails to protect against autoimmune tissue destruction in T1D and several other autoimmune diseases. An imbalance in Treg and effector T cell (Teff) cell activity may represent a central defect leading to T1D. Moreover, an imbalance may occur at the cellular level and also in controlling the activity of co-stimulation, whereby an activating co-stimulatory signal is favored over negative checkpoint regulators resulting in uncontrolled activation. Genome-Wide Association Studies (GWAS) in humans with T1D suggest concomitant defects occur in innate and adaptive immunity, predisposing T1D individuals to favor inflammatory signaling and a functional imbalance in adaptive immune regulation (FIG. 10). Genetic variations result in TCR and BCR signaling, alterations in the balance of costimulatory factors, increased innate inflammation, type 1 interferon production, and IL-2R defects.

T1D is treatable through administration of exogenous insulin, but no intervention allows prevention of T1D onset or reverses autoimmunity. Several immunotherapies have strived to induce tolerance to T1D self-antigens by inhibiting Teff or augmenting Treg functions, however incomplete knowledge of how Teff/Treg develop and function in T1D has hindered success. This embodiment of the claimed invention provides novel therapies for T1D.

Lentiviral (LV) Modulation of CD226 and TIGIT

Figure 11A:
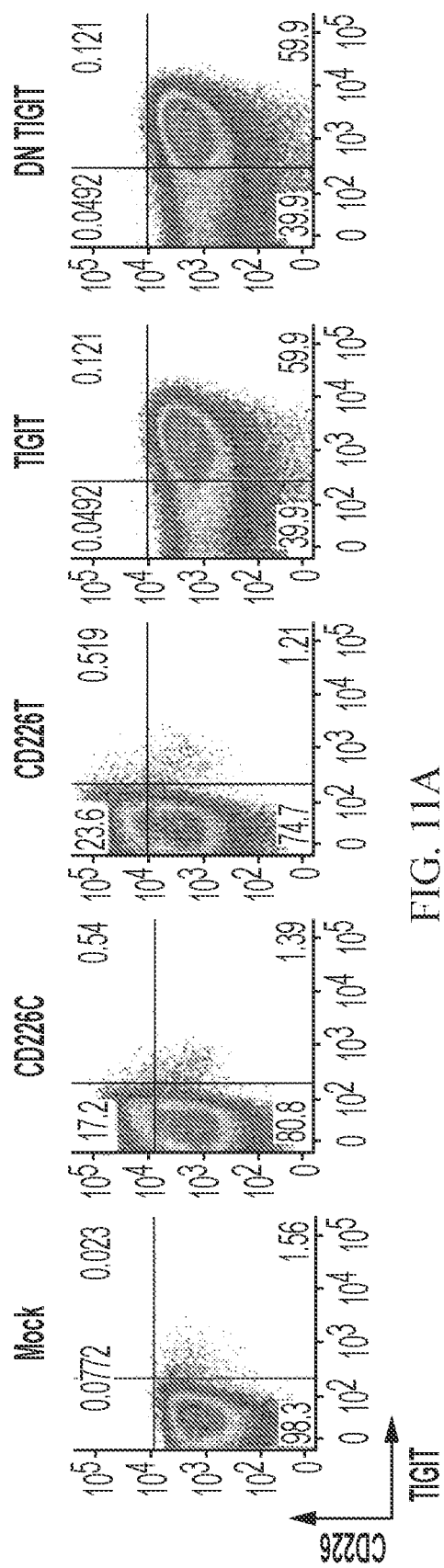
FIGS. 11A-11B. LV overexpression of CD226 and TIGIT. Human Treg were isolated by FACS and transduced at 48 h post-activation to overexpress (A) GFP mock, CD226 (C, major wt allele), CD226 (T, mutant allele), wild-type TIGIT, or a dominant negative TIGIT (Y225A, Y231A). Six replicate wells were harvested at d14 for FACS analysis. (B) Dual dye labeling allows the simultaneous monitoring of Treg and Teff proliferation during In vitro suppression assays. Preliminary data suggests overexpression of full-length, but not a dominant neg. form of TIGIT, augments Treg-mediated suppression of CD4+ Tconv cell proliferation. CTV, cell trace violet.
Figure 11B:
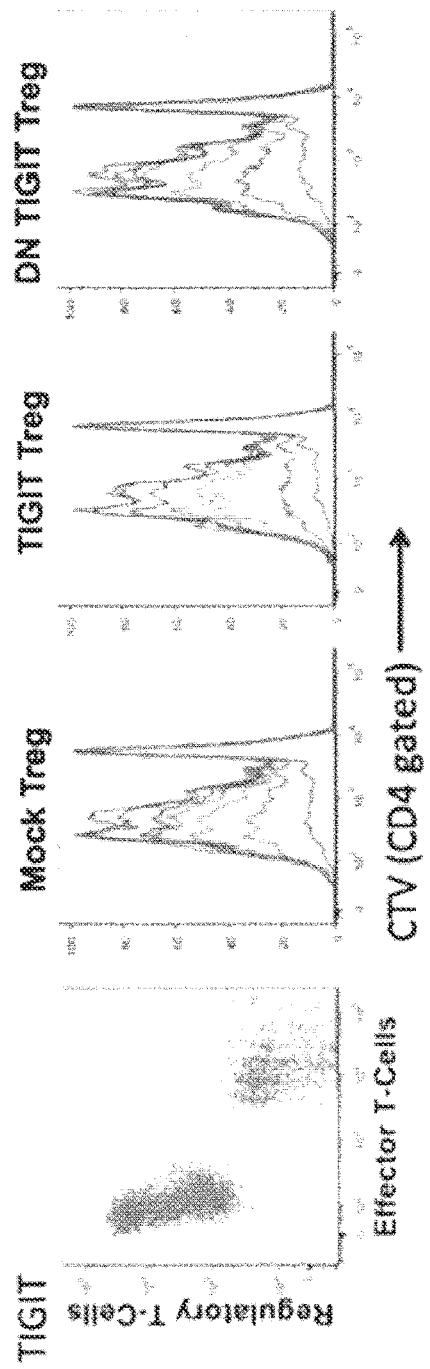

A library of overexpression and shRNA knockdown constructs to modulate CD226 and TIGIT expression was constructed to determine its impact on human T cell subsets (Table 3). Preliminary studies have validated constructs, as demonstrated for the overexpression constructs shown in (FIG. 11). In addition, our LV CD226 constructs demonstrated increased IFNγ in response to activation with anti-CD3 and anti-CD28.

TABLE 3

| Overexpression | Predicted Phenotype |
| --- | --- |
| *CD226C(major allele).eGFP | ↑ Treg IFNγ; ↑ Th1 cell |
| *D226T(minor allele).eGFP | ↑↑Treg IFNγ; ↑↑ Th1 cell |
| *TIGIT(wt). eGFP | ↑ Treg cell; ↓ Th1 cell |
| **DN TIGIT(mut).eGFP | Trans effect on APC ↑ IL-10; ↓ IL-12 |
| *eGFP alone | Transduction control |
| shRNA Gene Knockdown | |
| ***CD226-shRNA | ↑ Treg cell; ↓ Th1 cell |
| ***Scramble shRNA | Transduction control |
| *TIGIT-shRNA.eGFP | ↓ Treg cell activity; ↑ Th1 cell |
| *Scramble shRNA.eGFP | Transduction control |

*Gene of interest driven by CMV promoter. Enhanced GFP reporter.
**Dominant negative (DN) TIGIT mutated intracellular signaling domain (Y225A, Y231A).
***shRNA driven by U6 promoter. Transduced cells are selected by puromycin.

LV Gene Transfer Facilitates the Study of Human Autoreactive TCRs.

Figure 13A:
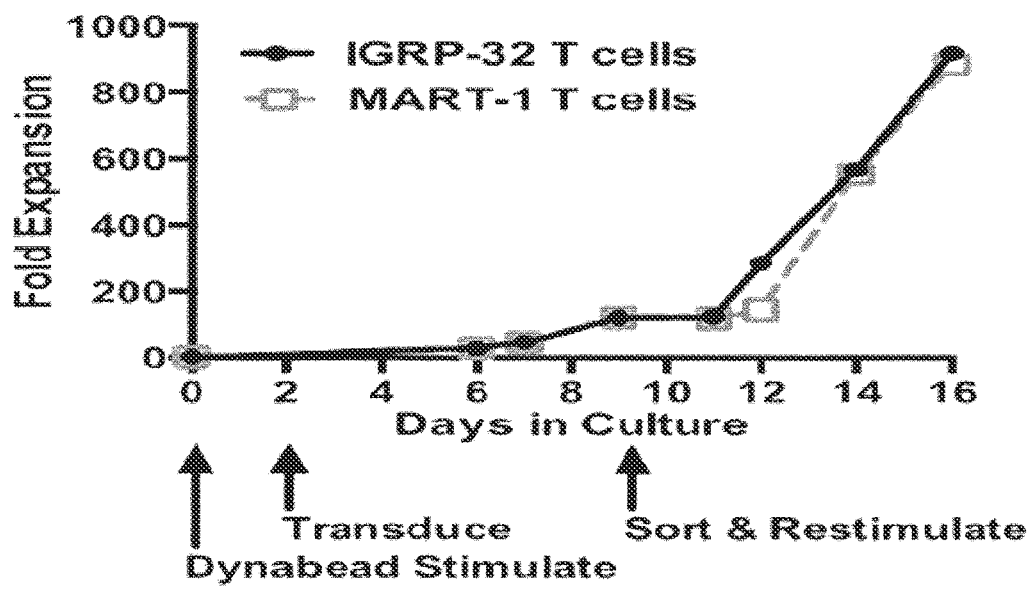
FIGS. 13A-13B. Cell-mediated lymphocytotoxicity (CML) assay for CD8+ T cells. A) Primary CD8+ T cells were stimulated with anti-CD3/28 beads and then transduced with LV encoding the IGRP TCR. After 9 d, GFP+ cells were sorted and expanded for an additional 7 d. B) MART-1 (ctrl) or IGRP CTL were used in a CML against BL5 indicating effective lysis of β cells at a 1:5 E:T ratio.
Figure 13B:
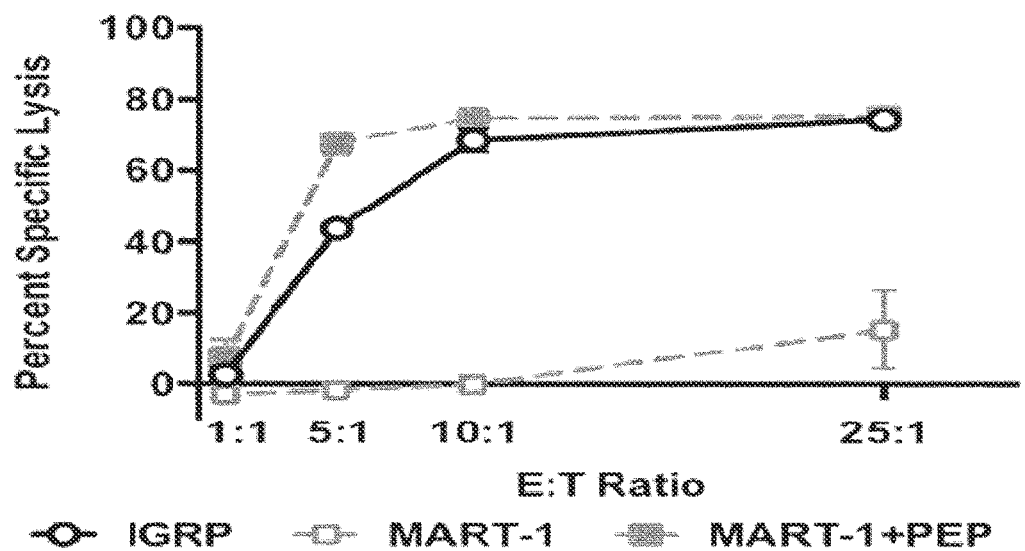

A robust LV gene transfer platform to interrogate Ag-specific T cell activity was developed. This system allows for multicystronic expression of TCRα and TCRβ chains in addition to reporter genes. These constructs include the ability to alter the specificity of both $CD4^+$ and $CD8^+$ T cells recognizing MHC class I and II-restricted peptides presented in the context of HLA-DR*03-01, DR*04-01, and HLA-A*02-01 (an example is shown in FIG. 13). This provides an unprecedented ability to assess the function of T1D Ag-specific Treg, Tconv, and $CD8^+$ T cells, as demonstrated in (FIG. 14).

IL-12 Negatively Impacts TIGIT Expression

Figures 14A, 14B:
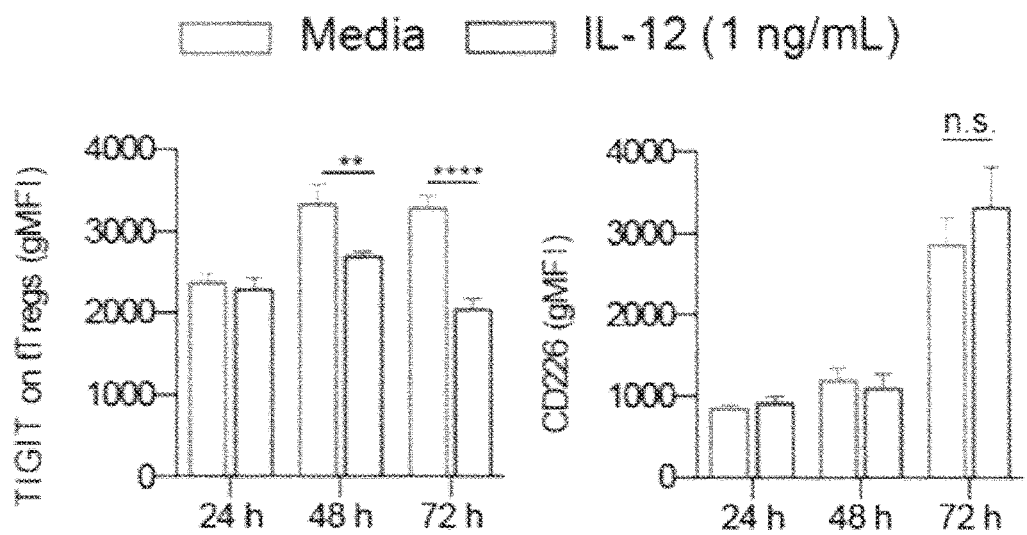
FIGS. 14A-14D. IL-12 augments $T_H1$-skewing of CD4+ T cells and attenuates TIGIT expression and proliferation by Treg. Human PBMCs (2.5×10⁵ cells/well) were activated with anti-CD3 (2 μg/mL) and anti-CD28 (1 μg/mL) in media alone (blue bars) or with the addition of IL-12 (1 ng/mL; red bars). IFNγ was assessed during the final 4 h of culture by FACS. Data are summarized as (A) gMFI of TIGIT on nTreg (CD4+FOXP3+ Helios+), (B) CD226 gMFI on CD4+ T cells, (C) percent CD4+IFNγ+ cells, and (D) frequency of nTreg. Shown is the mean±SE (N=6).
Figures 14C, 14D:
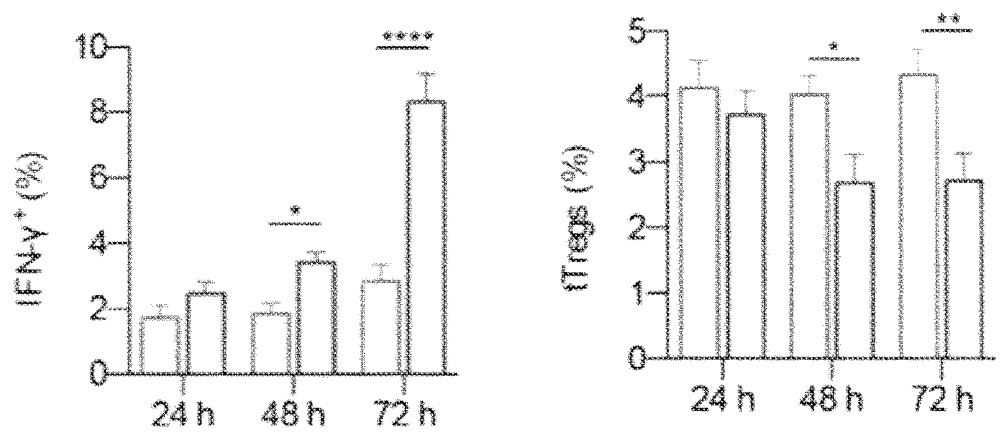

While it has been previously shown that both CD226 and TIGIT increase upon T cell activation, the change in TIGIT expression by human nTreg has not been characterized following culture with IL-12. As shown previously, CD226 expression increased over the 72 h. Likewise, TIGIT increases following TCR activation. TIGIT upregulation was attenuated in IL-12 conditions in $FOXP3^+$ $Helios^+$ Treg (FIG. 14A). IL-12 upregulated IFNγ as expected (FIG. 14C), however, the proportion of nTreg recovered from the culture decreased with IL-12 (FIG. 14D). These data suggest a mechanism whereby IL-12 may augment $T_H1$ production of IFNγ concomitant with a reduction in both nTreg proliferation and TIGIT expression. These findings provide an important biomarker of anti-IL-12 antibody (ustekinumab) therapy in trials in Chron's Disease, psoriasis, and proposed in T1D through the Immune Tolerance Network (ITN).

Development of TCR Expression Constructs

To express functional de novo TCRs in $CD4^+$ and $CD8^+$ T cells, LVs were generated using a high-affinity tumor-reactive TCR recognizing the melanoma antigen, Melan A, in the context of HLA-A*0201. Likewise, T cell clones recognizing β cell autoantigens were isolated from T1D patients. Full TCR α- and β-chain genes encoding TCRs recognizing peptides from pre-proinsulin (PPI), glutamic acid decarboxylase (GAD), and insulin-related glucose-6-phosphatase catalytic subunit 2 related protein (IGRP), were cloned into a pFUGW expression vector (Table 4). These TCR LV constructs facilitate equimolar expression of TCR α- and β-chains via multicistronic T2A and P2A elements. Virus production and transduction can be conducted as described previously (Ventura et al. (2004)). Cells can be cultured with IL-2 until d 9. On d 9 cells can be sorted using fluorescent reporter and transgene positive cells re-stimulated with Dynabeads and expanded for an additional 7 d.

Figure 12:
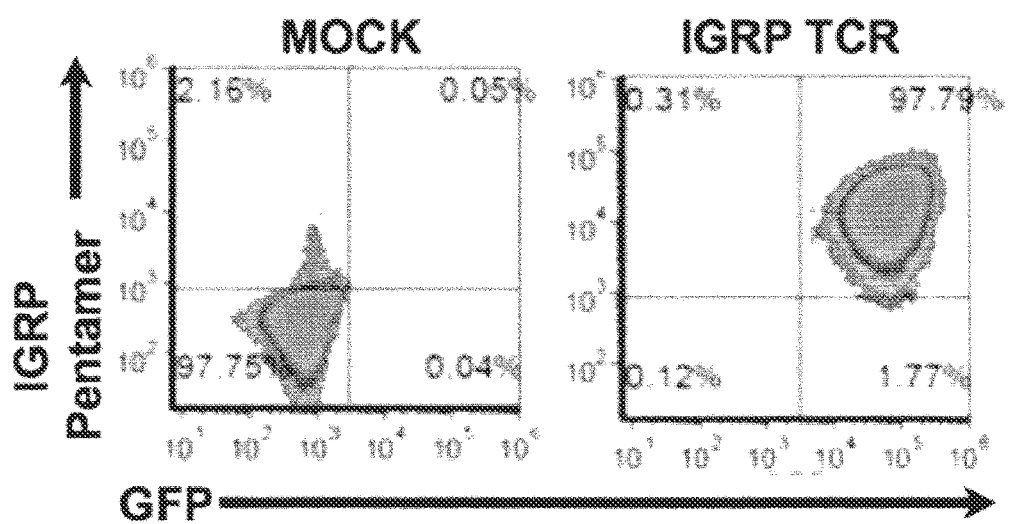
FIG. 12. LV gene transfer of the IGRP TCR generates MHC pentamer+CD8+ T cells. Human CD8+ T cells were transduced with a LV vector encoding the IGPR-TCR (Table 4).

Preliminary studies validate expression of these TCRs following transduction of primary human $CD4^+$ T cells and $CD8^+$ T cells through MHC-multimer staining (FIG. 12) and activation (CD69 upregulation and IL-2 production) following incubation with K562 HLA expressing cells with cognate peptides.

TABLE 4

TCR constructs to be used for the generation of antigenic specific CD4 and CD8 T cells

| Clone | Antigen Target | TCRα | TCRβ | HLA Restriction | Ref/ Source |
| --- | --- | --- | --- | --- | --- |
| 1E6 | $PPI_{18-24}$ | 13-2/13-2 | 8 | HLA-A*0201 | (1-3) |
| 32 | $IGRP_{255-273}$ | 12.1 | 20 | HLA-A*0201 | (4, 5) |
| MART1 | $Melan-A_{27-35}$ | 35 | 10.3 | HLA-A*0201 | (6) |
| *R164 | $GAD_{555-567}$ | 12.1 | 5.1 | HLA-DR*0401 | (7, 8) |
| *4.13 | $GAD_{555-567}$ | 12.1 | 5.1 | HLA-DR*0401 | (7, 8) |
| PM1#11 | $GAD_{555-567}$ | 35.02 | 5.1 | HLA-DR*0401 | (11) |

TRC-LV will encode an expressed far-red fluorescent tag for sorting.
*R164 and 4.13 recognize GAD with high and intermediate affinity respectively.

To determine the effectiveness of these cells cell-mediated lymphocytotoxicity (CML) assays were performed with the Class I HLA-A*0201$^+$ BL5 cells as targets and HLA-A*0201 restricted, IGRP-reactive CTL as the effector cells. Numerous CML assays were performed with this system to study required effector to target (E:T) ratios, mechanisms of CTL-mediated lysis, as well as changes in lysis due to priming of BL5 cells with IFNs. IGRP-CTL lyse BL5 cells while MART1-CTL only lyse MART-1 peptide pulsed BL5 cells (FIG. 13). Lysis can be titrated by decreasing the E:T ratio. As BL5 cells express IGRP, BL5 cells do not require pulsing with IGRP peptide. IFNγ increased lysis of BL5 cells by IGRP-CTL. Lysis is partially dependent on Fas and perforin as an anti-Fas antagonistic antibody and concanamycin (CMA) respectively both partially block lysis. Killing is further reduced by the combination of CMA and anti-Fas. Lysis is dependent on HLA, as antibody blockade of HLA eliminates lysis. For these experiments, CTL can be co-transduced with the IGRP TCR and the vectors in Table 3 to assess the impact of these costimulatory molecules on CTL activity. Co-reporter expression and TCR (far red reporter) and CD226 or TIGIT directed vectors (eGFP) can be used to ensure uniform stable expression on FACS purified populations. For MHC class II restricted TCRs, proliferation, effector cytokine production, and in vitro suppression using peptide stimulations and autologous APC or HLA-expressing artificial APCs for stimulation (K562.HLA-DR*0301 or HLA-DR*0401) can be assessed. This system can expand antigen-specific T cells (CD4 and CD8), utilizing starting clinically feasible material (~10-20 ml blood draw), ~100-fold at d9, and 1000-fold at d14 following FACS sorting and restimulation to enrich transduced populations. Furthermore, these expanded T cells remain Ag-reactive and are effective at lysing β cells facilitating experiments with gene modified CTL.

Impact of Innate Inflammatory Cytokines

In recent onset T1D where insulitis is present, infiltrates (containing CTL, macrophages, B cells, and $CD4^+$ T cells) associate with insulin positive islets as opposed to insulin deficient endocrine clusters. Persisting insulitis is associated with decreases of only β cells (not a cells) and increases in MHC I and FAS. Thus, specific immune reactivity to β cell antigens is central to T1D progression, and CTL responses are likely key effectors eliminating β cells. However, several unknowns exist with regards to additional requirements, including the immune checkpoint regulators involved in controlling effector molecules used by autoreactive CTL to kill β cells. The maintenance of immune regulation is susceptible to environmental control (FIG. 10). Localized innate inflammatory cytokines may attenuate TIGIT, allowing for the activation and expansion of pathogenic autoreactive T cells.

Impact on Skewing, Cytokine Production, and In Vitro Suppression

The impact of type 1 IFNα, IFNβ, IL-113, IL-18, IL-12, IL-23, and IL-6 on the ratio of CD226 and TIGIT can be tested. Innate cytokines may cause increased T cell skewing and CD226 relative to TIGIT on Treg and Teff/CTL-ultimately rendering Treg less suppressive. Treg may adopt a Teff-like phenotype (loss of FOXP3, acquisition of IFNγ and IL-17) or Teff cells may become refractory to suppression, as has been described in patients with T1D.

Determining the Impact of Innate Cytokines on CTL Activity and Killing of βL5

βL5 or monolayered islets can be treated with or IFNγ (100 U/mL) for 24 h. The cells can then be washed and CTL generated and genetically manipulated as described above with the addition of treatment during the in vitro expansion protocol with titrating amounts of cytokine (3-fold serial dilutions from 20 ng/ml each). CML can be collected, washed and subjected to flow cytometry (CD8, IFNγ, CD107a, perforin, granzymes, CD226, TIGIT). Supernatants can be collected for multiplexed cytokine analysis (e.g., by Miliplex). Optimal concentrations can be determined and moved into CML assays. CML can be performed by using β cells or monolayered islets as targets. CTL can be used at a 5:1 E:T ratio as this provides for observations of increased as well as decreased lysis. The specific impact of CD226 and TIGIT can be further tested with agents (agonists/antagonists).

TIGIT is likely to be enriched on Treg with potent suppressor activity. Thus, overexpression constructs can augment the suppressive capacity of Treg, and potentially, alter APC and Tconv into a more tolerogenic state (e.g., IL-10 producing). Conversely, shRNA constructs designed to downregulate TIGIT can reduce the suppressive activity of Treg. Increased expression and/or signaling via CD226 can be seen in individuals carrying the T1D-associated risk allele (T) at rs763361. In addition, overexpression of CD226 can augment the capacity of autoreactive T cells to produce effector cytokines (e.g., IL-17 and IFNγ), and likewise, increase the cytotoxic activity of CTL.

Biologics now play an increasingly important role in controlling autoimmune reactivity by modulating cytokine signaling (e.g., ustekinumab and tocilizumab). Some of this beneficial effect is due to blocking inflammation that attenuates suppressive activity and negative regulators normally expressed by Treg. Specifically, inflammatory cytokines can attenuate FOXP3 and TIGIT expression by Treg, and conversely augment CD226 expression and differentiation into $T_H1$ and $T_H17$ cell lineages.

Example 10—Assessing the Expression of CD226 and TIGIT Throughout the Natural History of T1D in the NOD Mouse and in Humans with T1D Destruction of islet β cells may occur when a functional imbalance results favoring activation and expansion of autoreactive effector $CD^4$ and $CD8^+$ T cells overwhelms the capacity of Treg to maintain immune tolerance. CD226 on tissue- and islet resident T cells may increase and TIGIT may reduce during the pathogenesis of disease in the NOD and in humans with T1D.

Figure 15:
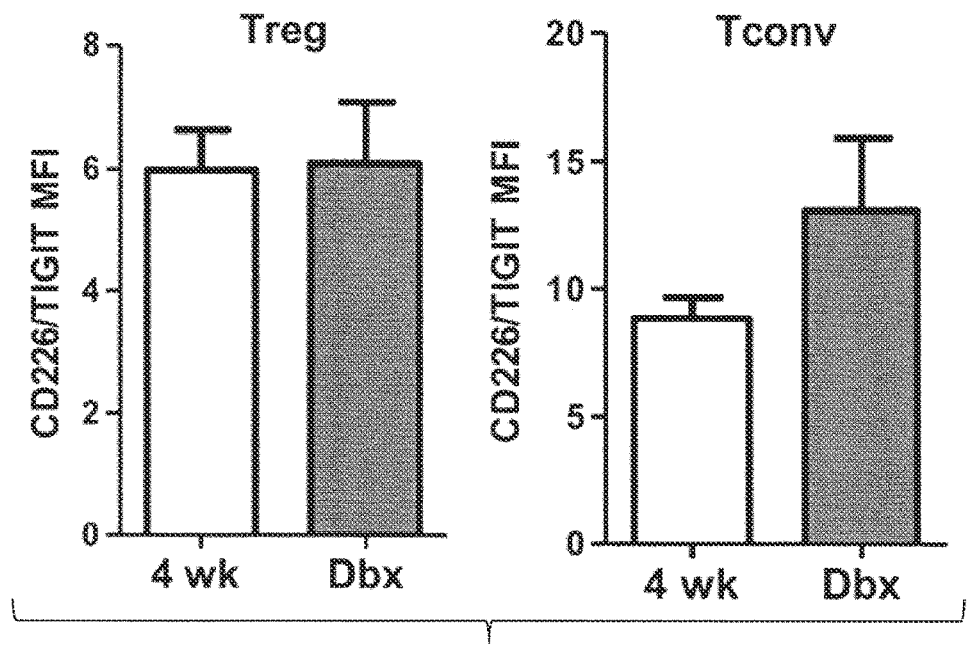
FIG. 15. CD226 and TIGIT expression in NOD mice. pDLNs were harvested from female NOD mice at 4 wks of age or at onset (Dbx). Single cell suspensions were stained for live/dead, CD4, FoxP3, CD226, and TIGIT. Shown are the ratio of CD226:TIGIT (as a ratio of gMFI) on gated Treg (CD4+FoxP3+) and Tconv (CD4+FoxP3−) cells (n=4, p=0.07).

The NOD mouse develops spontaneous disease with many similarities to human T1D, albeit with a much more pronounced islet infiltration and presentation. Importantly, this model affords the ability to directly assess the impact of specific genes and pathways in an immune replete host. The data indicates a higher ratio of CD226:TIGIT at disease onset relative to 4 wk old mice (FIG. 15).

Investigating the Role of CD226 and TIGIT in the NOD Mouse Model of T1D

Female NOD mice, Non-Obese Resistant (NOR), and C57BL/6 control mice (Jackson Laboratories) can be followed longitudinally at defined checkpoints in the disease process (4, 8, 12, 16 wk, and at disease onset). Groups of mice (N=10/group) can be sacrificed at each time point for flow cytometric and histological analysis of CD226 and TIGIT expression on T cells and NK cell populations. CD112 and CD155 can also be measured on islet resident APC populations. Incidence studies can be conducted in female NOD (N=20/group) and can be defined as BG>250 mg/dL on 2 successive days. 80% of female NOD mice developed disease at 21 wks of age. In addition to standard NOD mice, the specific impact of these receptors can be assessed on disease development through ZFN and CRISPR targeted knockouts (NOD.TIGIT$^{-/-}$ and NOD.CD226$^{-/-}$). Pancreata can be processed for immunohistochemistry and stained for Ki67, insulin, glucagon, CD3, CD4, CD8, CD226, TIGIT, FoxP3, B220, F4/80, CD112, CD155 and CD11c to assess the expression of the markers of interest on resident and infiltrating lymphocytes. PB, splenocytes, pDLN, axillary LN, and BM cells can be taken for immunological assays and FACS.

Immune Profiling

Complete blood count (CBC) by coulter counter can be followed by immunophenotyping via flow cytometry. Antibodies can be used for the detection of CD3, CD4, CD8, CD226, TIGIT, CD25, FoxP3, Helios, IFNγ, IL-10, CD56, CD16, CD11b, CD11c, CD112, and CD155. Single cell suspensions prepared from islets, spleens, pancreatic and mesenteric lymph nodes, as well as BM and thymus can be subjected to flow cytometry using a BD LSR Fortessa. These single cell suspensions can be probed for CD4$^+$ and CD8$^+$ T cells with BDC2.5 and IGRP tetramers (NIH Tetramer Core) and markers for naïve, activated, memory, and regulatory phenotypes, as well as CD226 and TIGIT. DCs can be assessed for markers to distinguish pDC and mDC, maturation status, co-stimulatory and co-inhibitory molecules as well as monocyte expression of CD112 and CD155 ligands and production of IL-12 and IL-10 in response to TLR ligands (LPS, Poly I:C, CpG).

Adoptive Transfer (AT) and Mixed Bone Marrow Chimera Experiments

The impact can be ascertained of Treg and Teff cell expression of CD226 and TIGIT through AT, and adoptive co-transfer experiments in NOD.RAG$^{-/-}$ recipients alone, or following co-AT with diabetegenic splenocytes (2×10$^7$ cells injected into NOD.RAG$^{-/-}$ recipient mice). Recipient mice can be followed for T1D development via blood glucose as indicated.

Mixed bone marrow chimeric mice consisting of TIGIT or CD226 deficient and WT immune cells can be generated. In these mice, WT cells can provide the necessary diabetegenic environment with cytokines, chemokines, and surface ligands during T1D. An equal amount of NOD.Thy1.2 WT and either NOD.Thy1.1 TIGIT$^{-/-}$, Thy1.1 CD226$^{-/-}$, or Thy1.1 WT bone marrow as control can be transferred into lethally irradiated NOD Rag1$^{-/-}$ mice to exclude the interference of endogenous T cells. Antibiotics can be added into drinking water for 6 weeks to prevent infection. Six weeks after transplantation, the reconstitution of CD4$^+$, CD8$^+$ T cells, B cells, DC, macrophage, and neutrophils in PBMC can be confirmed by flow cytometry. Incidence can be followed at indicated above. To understand if TIGIT and CD226 play roles in CD4 T cell activation, proliferation, and migration, diabetic mice can be sacrificed and pancreata, spleens, draining, and non-draining lymph nodes can be collected. The proportion of allelic marked donor cells and expression of activation markers and Ki-67 can be assessed by FACS and histology.

CD226 and TIGIT are reported to regulate lineage differentiation and cytokine production. The expression of various transcriptional factors (Tbet, RORγt, GATA3, FoxP3) and cytokines including IFNγ, IL-17, IL-4/IL-5, Foxp3, and IL-10 can be determined.

Analysis of In Vitro Suppressor Function

Freshly isolated Treg and T responder splenocytes from NOD mice or NOD.TIGIT$^{-/-}$, CD226$^{-/-}$ mice can be assessed for their ability to suppress, or be suppressed in cross-over in vitro suppression assays. Tresp (labeled with Cell Tracker Violet) were plated in triplicate with purified Treg (labeled with APC channel dye) added at varying ratios from 1:1 to 1:64 Treg to Tresp cells.

Vaccine Studies

Female NOD, NOD.CD226$^{-/-}$, and NOD.TIGIT$^{-/-}$ mice at 8 wk of age can be used to explore the effects of costimulation on recall responses to exogenous antigen challenge. This provides insight into whether immune sufficiency is maintained and whether effector, memory, or regulatory mechanisms are involved with CD226:TIGIT signaling. Group i) consists of a control, no injections, Group ii) HEL antigen given in prime and 2 wk later boost with alum adjuvant. Groups can be bled weekly for serum assessment of HEL specific IgM and IgG titers by ELISA. 8 wk post-boost of HEL, the animals can be euthanized and spleens removed. Cells can be placed into culture and stimulated with HEL antigen to test recall responses assessing differentiation and proliferation by FACS, and cytokine secretion in supernatants (Milliplex).

Human data suggests that CD226 is tightly associated with memory and effector T cell responses. Thus, NOD mice, when compared to NOR and C57BL/6, can exhibit a progressive increase in CD226 relative to TIGIT within the islets and in the pDLNs. Given that TIGIT$^{-/-}$ mice exhibit exacerbated Experimental autoimmune encephalomyelitis (EAE), the NOD background can exhibit a higher incidence and a potentially more rapid progression of T1D. Given the costimulatory nature of CD226, CD226 deficient mice may have attenuated disease; however, the opposite was observed in CD28 deficient mice, suggesting costimulation may also be necessary for the maintenance of Treg activity. While the use of gene targeting in the NOD represents the most rapid means to assess these questions, it lacks the cell specificity normally afforded by conditional knockout systems (e.g., FoxP3-Cre). Hence, CD226 or TIGIT-LoxP sites for lineage specific deletion can be produced.

PBMC Cross-Sectional Studies of CD226 and TIGIT

Studies can be conducted with cross-sectional samples with cohorts comprising normal healthy controls, at risk relatives (single and multiple autoantibody positive), new onset subjects (defined as ≤3 months post diagnosis), established T1D (>3 months), and subjects with T2D (to address questions of immune versus metabolic effects). Analysis of clinical samples from fresh PB and cryopreserved PBMC can be performed.

nPOD In Situ Analysis of CD226 and TIGIT

In addition to studies in PB, samples from a unique and innovative resource (i.e. nPOD) that obtains cells and tissues of pancreatic or lymphoid origin (spleen, LN—both pancreatic and peripheral, PB) from groups with or at various risks for T1D can be studied. This can permit directly addressing pertinent and long-standing questions in human T1D as to whether PBMC reflect activities at the pancreatic LN and insulitis lesion. The pancreata, spleens, pancreatic LN, peripheral LN, anti-coagulated whole blood and serum can be collected, processed, and stored. Samples from individuals with T1D, T2D, and non-autoimmune controls (from 0 to 80 yr) can be collected. In addition, tissues from "pre-diabetic" individuals through screening organ donors to identify those with one or more autoantibodies can be obtained. Post-acquisition analyses can include high resolution HLA typing, ImmunoChip (SNP) analysis, C-peptide analysis, as well as standard H&E histology and immunohistochemistry.

IFNγ Producing Treg are Enriched in PB of Patients with T1D

Figure 16:
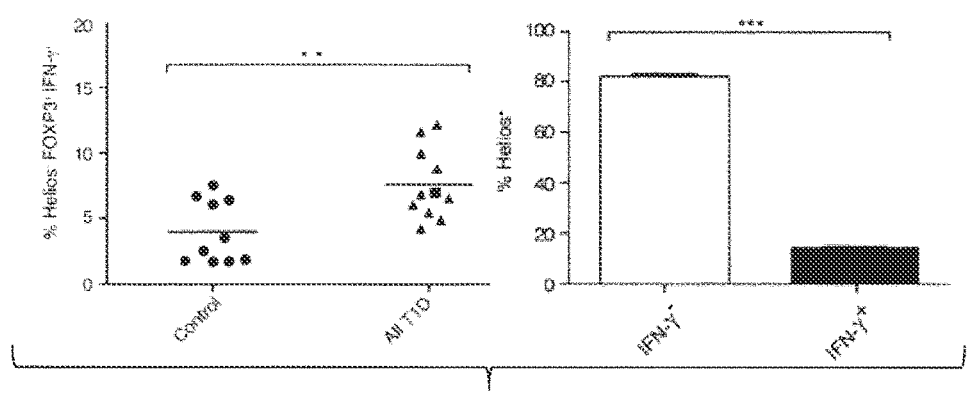
FIG. 16. IFNγ+ Treg are enriched in T1D. PBMC from healthy controls (n=10) or patients with T1D (n=11, including 1 recent-onset case, square) were stimulated 4 h with PMA/ionomycin. Viable CD4+ lymphocytes were gated, and FOXP3, Helios, and IFNγ were analyzed by FACS. **P<0.01.
Figure 17A:
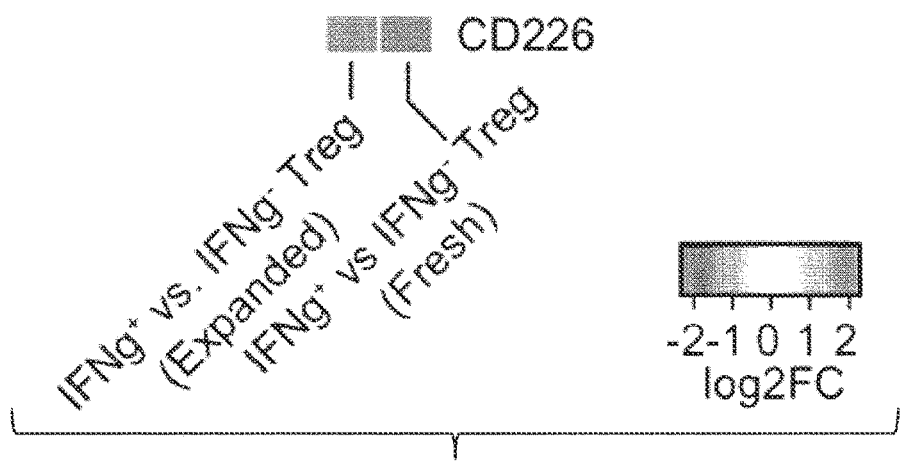
FIGS. 17A-17C. IFNγ+ Treg express elevated CD226 and reduced TIGIT. Human IFNγ+ Treg and Tconv were isolated by FACS (9). (A) Shown is CD226 heat signature between 4 h PMA/ion activated IFNγ+ and IFNγ− Treg immediately after FACS isolation (fresh) and following 14 d ex vivo expansion and reactivation (expanded). (B) Differentially expressed genes between all four populations (IFNγ+/− Treg and Tconv subsets, d14) demonstrate that TIGIT is elevated in Treg and highly expressed in IFNγ− Treg subset (N=5). (C) PCA analysis of d14 expanded populations.
Figure 17B:
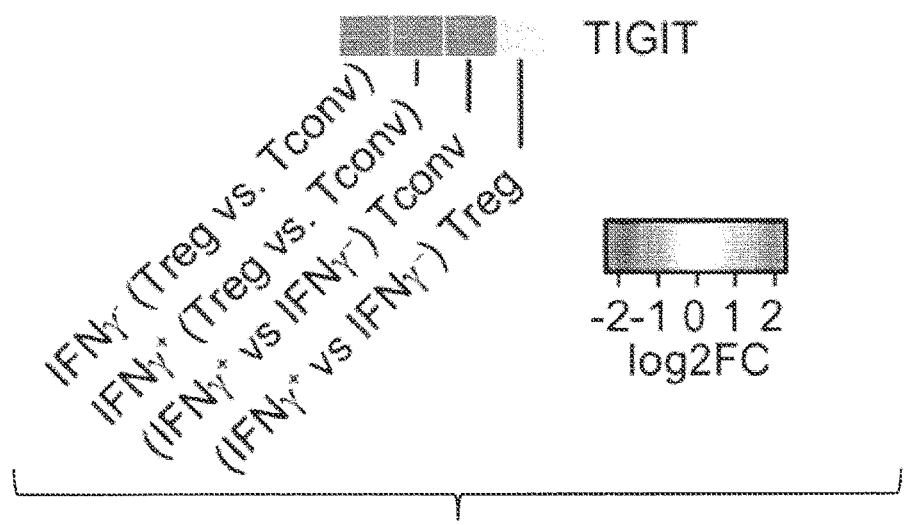
Figure 17C:
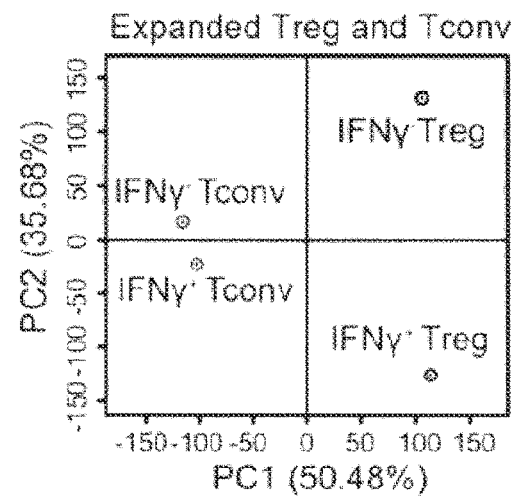
Figure 18A:
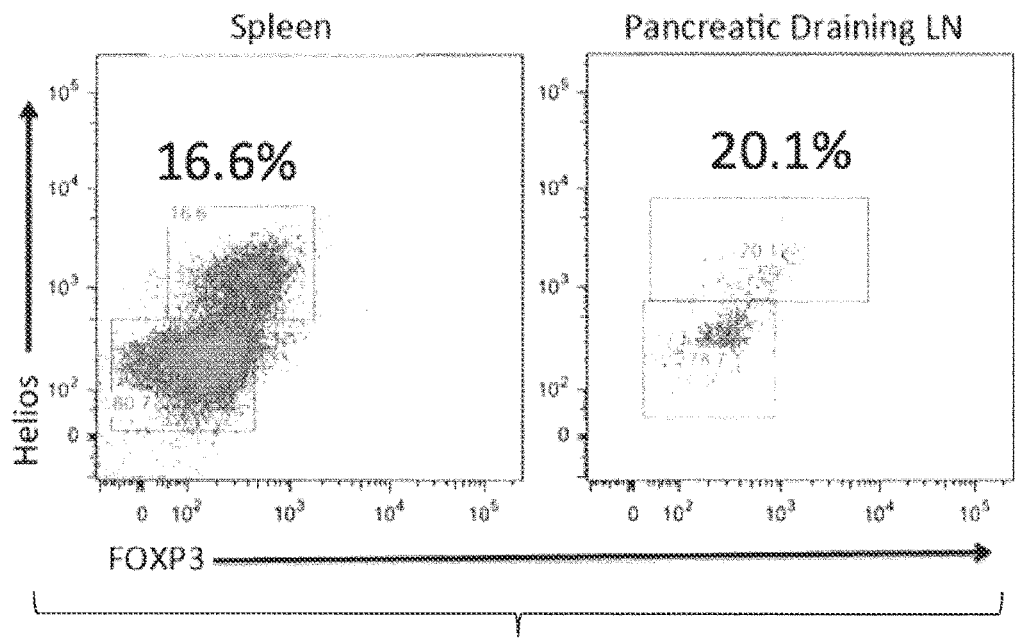

Defective suppression by Treg and/or Teff cell resistance is observed in patients with T1D. An increase of IFNγ$^+$ Treg that were Helios$^-$, significantly reduced in suppressive activity, and partially methylated at the TSDR (FIG. 16). IFNγ$^+$ or IFNγ$^-$ Treg and Tconv subsets were isolated for microarray profiles. Notably, both freshly isolated and 14d expanded IFNγ$^+$ Treg expressed significantly more CD226 than the IFNγ$^-$ Treg subset (FIG. 17A), and TIGIT expression was higher in the IFNγ$^-$ Treg compared to IFNγ$^+$ Treg (FIG. 17B). Principal component analysis (PCA) of these populations indicated clear divergence between Treg and Tconv populations, with further variance in IFNγ$^+$ and IFNγ$^-$ Treg (FIG. 17C).

Isolation of Immune Subsets from nPOD Material

A four-way sort (FACS Aria III) is performed to isolate snap frozen cell pellets and live cell aliquots of B cells, Tconv, Treg, and CD8$^+$ T cells. FIG. 19 illustrates feasibility of isolating live viable cells and their subsets from an nPOD donor.

Characterization of the Islet and pDLN Resident Expression of CD226 and TIGIT

Tissues obtained from nPOD (pDLN, irrelevant DLN, spleen, PB) can all be collected immediately and processed into single cell suspensions (Miltenyi Gentle MACS Dissociator). Samples can then be stained in parallel for surface and intracellular flow cytometry or FACS isolation. Pancreatic immunohistochemistry (antibody) or in situ hybridization (ISH) can be used, as necessary, to delineate the cells compromising the T1D lesion.

The following tests can be performed:

Immunohistochemistry—

Pancreatic tissue sections can be stained for CD4, CD226, TIGIT, and FOXP3. Fluorescent images can be scanned (Zeiss LSM510 Meta confocal microscope/Aperio Scanscope) and data can be analyzed and quantitative measures assessed using Zeiss LSM510, Metamorph, or Aperio software.

Transcriptional Analysis—

Tissue samples, and the potential for laser capture of islets or infiltrates, can be analyzed with a Nanostring nCounter as noted for fixed tissues (FIG. 1).

The milieu at the draining lymph node and islet of patients with T1D may be enriched in autoreactive T cells expressing high levels of CD226. A relative reduction in the negative regulatory TIGIT may be observed. Moreover, activated lymphocytes within the lesion and draining lymph node may be observed in higher proportion than PB and also in higher proportion of those with T1D or multiple autoantibodies compared with control lymph node tissue.

Example 11—Testing the Therapeutic Potential of Modulating CD226 and TIGIT Activity One embodiment of the invention provides therapeutics that block CD226 costimulation, or alternatively augment the regulatory profile of Treg through bolstering TIGIT to avert autoimmunity.

Implications for Treg cell therapy—CD226 and TIGIT identify functionally distinct subpopulations of Treg.

Figure 20:
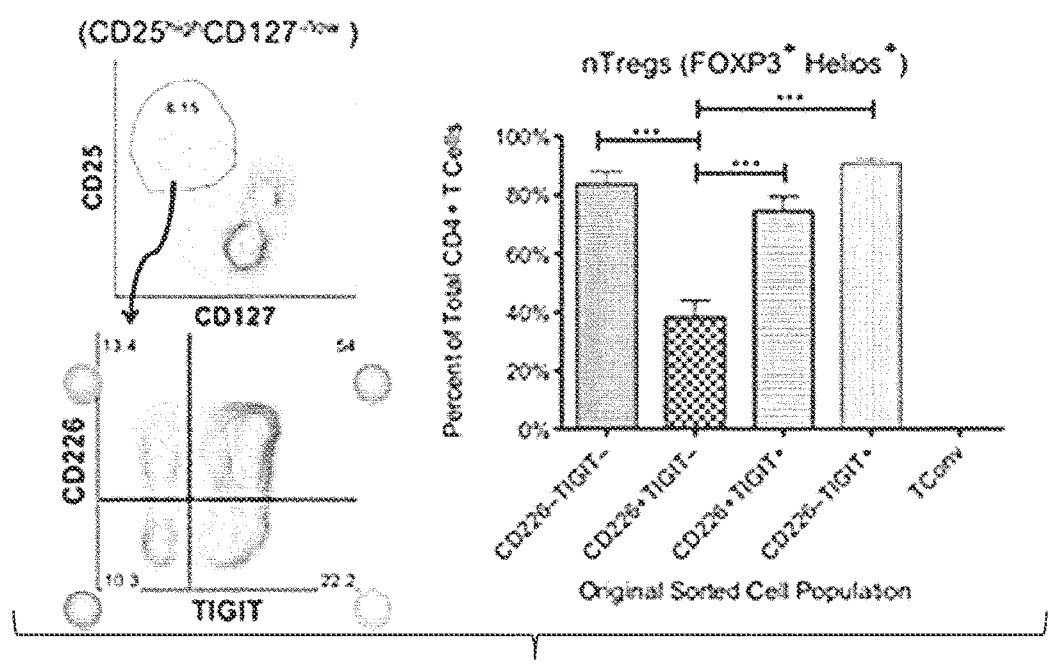
FIG. 20. Expansion of Treg expressing TIGIT and/or CD226 yield subpopulations differing in proliferative ability, purity, and suppressive capacity. CD4+CD25+CD127$^{-/lo}$ Treg (upper left plot) were isolated from 100 mL of human PB and further divided to yield four distinct populations based on CD226 and TIGIT expression (lower left, indicated sort quadrants). Day 14 expanded Treg and Tconv were assessed for FOXP3 and Helios (N=4).
Figure 21A:
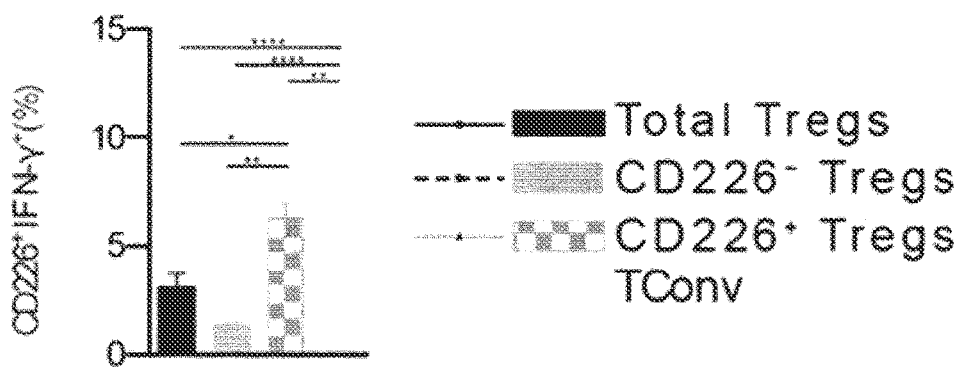
FIG. 21A-21C. Elimination of CD226+ cells results in a highly pure population of Treg. CD4+CD25+CD127$^{-/lo}$ Treg were further divided based on initial CD226 expression and expanded for 14 d. (A) Shown are the frequency of CD226+IFNγ+ cells post activation, (B) the ratio of TIGIT:CD226 on Treg following in vitro suppression culture, and C) the percent of cells demethylated at the TSDR.
Figure 21B:
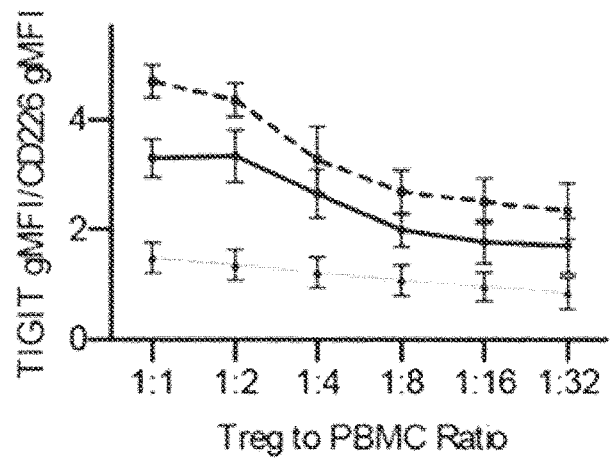
Figure 21C:
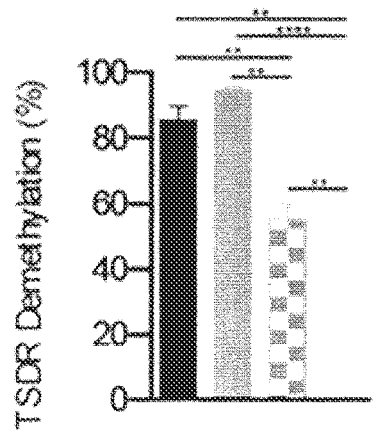

Treg may lead to the induction of long-term tolerance and preservation of endogenous or transplanted β-cell mass. Current protocols to generate human Treg are susceptible to contamination by non-Treg and the potential for lineage instability following in vitro culture (31, 69-71). This embodiment of the invention provides FACS-isolated Treg ($CD4^+CD25^{hi}CD127^-$ T cells) that are subdivided into quadrants based on CD226 and TIGIT expression (FIG. 20). $TIGIT^+$ Treg constitute the majority of the initial population but are highly refractory to expansion. $CD226^+$ $TIGIT^-$ Treg adopt a transcriptional program (Nanostring) similar to Tconv cells, are reduced in suppressive capacity, produce IFNγ, and are methylated at the FOXP3-TSDR. $CD226^-$ Treg, irrespective of initial TIGIT expression, upregulate TIGIT post-expansion and are highly suppressive and pure. Elimination of CD226-expressing Treg alone could improve Treg purity post-expansion (FIG. 21). While Treg were largely suppressive, elimination of CD226 improved the suppressive capacity of the final product, indicating this ratio may emerge as an important surrogate measure of Treg suppressive activity.

Identification of Drugs, Tolerogenic Cytokines, and Modified Treg Cell Therapies to Bolster TIGIT and Treg Cell Activity TIGIT expression may augment the suppressive capacity of Treg, while simultaneously limiting Teff cell activity. Various immunomodulatory drugs and tolerogenic cytokines can augment TIGIT expression. Drugs and cytokines known to increase Treg may also upregulate TIGIT (e.g., rapamycin, All-trans Retinoic Acid (ATRA), IL-10, TGFβ, low-dose IL-2, PI3K inhibitors). Additional agents can be screened and identified which modulate TIGIT activity and/or expression in Treg.

Determining if Antibodies, Somamers, and Ig-Fusion Proteins can Modulate Treg and Tconv Cell Activity In Vitro The identification of CD226 and TIGIT has generated a new axis susceptible to immune modulation for cancer, immunizations, and autoimmunity. CD226 and TIGIT can be targeted through the use of activating and neutralizing antibodies, CD112 and CD155-Ig fusion proteins, and CD226 and TIGIT somamer reagents to impact Treg and Tconv cell activity.

CD226 expression clearly demarcates a population of human Treg that are unstable and produce effector cytokines, including IFNγ. Isolation of $CD226^-$ Treg will increase Treg suppressive activity and stability following in vitro expansion. This is important during acute activation, as CD127 is downregulated following activation, whereas, CD226 is upregulated. Therefore, addition of CD226 may increase the ability to discriminate bona-fide Treg from Teff populations during periods of ongoing T cell activation.

CD226 and TIGIT inhibitors can be screened in a high-throughput binding assay with CD155 expressing cell lines (K562) and fluorescently-labeled CD226 and TIGIT Ig fusion proteins. These studies can then be validated during in vitro suppression assays. In terms of CD226 and TIGIT inhibitors, the targeted inhibitors and agonists can recapitulate the results from LV overexpression and knockdown experiments and gene targeted mouse models. Larger drug libraries (e.g., those available through the NIH—National Cancer Institute) can also be screened to identify molecules modulating CD226 or TIGIT activity and/or expression.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

1. Skowera A, Ellis R J, Varela-Calvino R, Arif S, Huang G C, Van-Krinks C, Zaremba A, Rackham C, Allen J S, Tree T I, et al. CTLs are targeted to kill beta cells in patients with type 1 diabetes through recognition of a glucose-regulated preproinsulin epitope. *J Clin Invest*. 2008; 118 (10):3390-402.
2. Bulek A M, Cole D K, Skowera A, Dolton G, Gras S, Madura F, Fuller A, Miles J J, Gostick E, Price D A, et al. Structural basis for the killing of human beta cells by CD8(+) T cells in type 1 diabetes. *Nature immunology*. 2012; 13(3):283-9.
3. Knight R R, Kronenberg D, Zhao M, Huang G C, Eichmann M, Bulek A, Wooldridge L, Cole D K, Sewell A K, Peakman M, et al. Human beta-cell killing by autoreactive preproinsulin-specific CD8 T cells is predominantly granule-mediated with the potency dependent upon T-cell receptor avidity. *Diabetes*. 2013; 62(1):205-13.
4. Unger W W, Pinkse G G, Mulder-van der Kracht S, van der Slik A R, Kester M G, Ossendorp F, Drijfhout J W, Serreze D V, and Roep B O. Human clonal CD8 autoreactivity to an IGRP islet epitope shared between mice and men. *Annals of the New York Academy of Sciences*. 2007; 1103(192-5.
5. Unger W W, Pearson T, Abreu J R, Laban S, van der Slik A R, der Kracht S M, Kester M G, Serreze D V, Shultz L D, Griffloen M, et al. Islet-specific CTL cloned from a type 1 diabetes patient cause beta-cell destruction after engraftment into HLA-A2 transgenic NOD/scid/IL2RG null mice. *PLoS One*. 2012; 7(11):e49213.
6. Kawakami Y, Eliyahu S, Sakaguchi K, Robbins P F, Rivoltini L, Yannelli J R, Appella E, and Rosenberg S A. Identification of the immunodominant peptides of the MART-I human melanoma antigen recognized by the majority of HLA-A2-restricted tumor infiltrating lymphocytes. *The Journal of experimental medicine*. 1994; 180 (1):347-52.
7. Gebe J A, Unrath K A, Yue B B, Miyake T, Falk B A, and Nepom G T. Autoreactive human T-cell receptor initiates insulitis and impaired glucose tolerance in HLA DR4 transgenic mice. *J Autoimmun*. 2008; 30(4): 197-206.

8. Gebe J A, Yue B B, Unrath K A, Falk B A, and Nepom G T. Restricted autoantigen recognition associated with deletional and adaptive regulatory mechanisms. *J Immunol.* 2009; 183(1):59-65.
9. McClymont S A, Putnam A L, Lee M R, Esensten J H, Liu W, Hulme M A, Hoffmuller U, Baron U, Olek S, Bluestone J A, et al. Plasticity of human regulatory T cells in healthy subjects and patients with type 1 diabetes. *J Immunol.* 2011; 186(7):3918-26.
10. Bach J F. Autoimmune diseases as the loss of active "self-control". *Ann NY Acad Sci.* 2003; 998(161-77.
11. Schloot N C, Batstra M C, Duinkerken G, De Vries R R, Dyrberg T, Chaudhuri A, Behan P O, and Roep B O. GAD65-Reactive T cells in a non-diabetic stiff-man syndrome patient. *J Autoimmun.* 1999; 12(4):289-96.
12. Gregori S, Giarratana N, Smiroldo S, and Adorini L. Dynamics of pathogenic and suppressor T cells in autoimmune diabetes development. *J Immunol.* 2003; 171(8): 4040-7.
13. Pop S M, Wong C P, Culton D A, Clarke S H, and Tisch R. Single cell analysis shows decreasing FoxP3 and TGFbeta1 coexpressing CD4+CD25+ regulatory T cells during autoimmune diabetes. *J Exp Med.* 2005; 201(8): 1333-46.
14. Smilek D E, Ehlers M R, and Nepom G T. Restoring the balance: immunotherapeutic combinations for autoimmune disease. *Dis Model Mech.* 2014; 7(5):503-13.
15. Bottino C, Castriconi R, Pende D, Rivera P, Nanni M, Carnemolla B, Cantoni C, Grassi J, Marcenaro S, Reymond N, et al. Identification of PVR (CD155) and Nectin-2 (CD112) as cell surface ligands for the human DNAM-1 (CD226) activating molecule. *J Exp Med.* 2003; 198(4):557-67.
16. Qiu Z X, Zhang K, Qiu X S, Zhou M, and Li W M. CD226 Gly307Ser association with multiple autoimmune diseases: a meta-analysis. *Hum Immunol.* 2013; 74(2): 249-55.
17. Reinards T H, Albers H M, Brinkman D M, Kamphuis S S, van Rossum M A, Girschick H J, Wouters C, Hoppenreijs E P, Saurenmann R K, Hinks A, et al. CD226 (DNAM-1) is associated with susceptibility to juvenile idiopathic arthritis. *Ann Rheum Dis.* 2014.
18. Lozano E, Joller N, Cao Y, Kuchroo V K, and Hafler D A. The CD226/CD155 interaction regulates the proinflammatory (Th1/Th17)/anti-inflammatory (Th2) balance in humans. *J Immunol.* 2013; 191(7):3673-80.
19. Shibuya K, Shirakawa J, Kameyama T, Honda S, Tahara-Hanaoka S, Miyamoto A, Onodera M, Sumida T, Nakauchi H, Miyoshi H, et al. CD226 (DNAM-1) is involved in lymphocyte function-associated antigen 1 costimulatory signal for naïve T cell differentiation and proliferation. *J Exp Med.* 2003; 198(12): 1829-39.
20. Joller N, Hafler J P, Brynedal B, Kassam N, Spoerl S, Levin S D, Sharpe A H, and Kuchroo V K. Cutting edge: TIGIT has T cell-intrinsic inhibitory functions. *J Immunol.* 2011; 186(3):1338-42.
21. Liu S, Zhang H, Li M, Hu D, Li C, Ge B, Jin B, and Fan Z. Recruitment of Grb2 and SHIP1 by the ITT-like motif of TIGIT suppresses granule polarization and cytotoxicity of NK cells. *Cell Death Differ.* 2013; 20(3):456-64.
22. Levin S D, Taft D W, Brandt C S, Bucher C, Howard E D, Chadwick E M, Johnston J, Hammond A, Bontadelli K, Ardourel D, et al. Vstm3 is a member of the CD28 family and an important modulator of T-cell function. *Eur J Immunol.* 2011; 41(4):902-15.
23. Ferraro A, D'Alise A M, Raj T, Asinovski N, Phillips R, Ergun A, Replogle J M, Bernier A, Laffel L, Stranger B E, et al. Interindividual variation in human T regulatory cells. *Proceedings of the National Academy of Sciences of the United States of America.* 2014; 111(12):E1111-20.
24. Lozano E, Dominguez-Villar M, Kuchroo V, and Hafler D A. The TIGIT/CD226 axis regulates human T cell function. *Journal of immunology.* 2012; 188(8):3869-75.
25. Zhang Y, Maksimovic J, Naselli G, Qian J, Chopin M, Blewitt M E, Oshlack A, and Harrison L C. Genome-wide DNA methylation analysis identifies hypomethylated genes regulated by FOXP3 in human regulatory T cells. *Blood.* 2013; 122(16):2823-36.
26. Joller N, Lozano E, Burkett P R, Patel B, Xiao S, Zhu C, Xia J, Tan T G, Sefik E, Yajnik V, et al. Treg Cells Expressing the Coinhibitory Molecule TIGIT Selectively Inhibit Proinflammatory Th1 and Th17 Cell Responses. *Immunity.* 2014; 40(4):569-81.
27. Morgan R A, Dudley M E, Wunderlich J R, Hughes M S, Yang J C, Sherry R M, Royal R E, Topalian S L, Kammula U S, Restifo N P, et al. Cancer regression in patients after transfer of genetically engineered lymphocytes. *Science.* 2006; 314(5796): 126-9.
28. Brusko T M, Koya R C, Zhu S, Lee M R, Putnam A L, McClymont S A, Nishimura M I, Han S, Chang L J, Atkinson M A, et al. Human antigen-specific regulatory T cells generated by T cell receptor gene transfer. *PLoS One.* 2010; 5(7):e11726.
29. Chen Y G, Forsberg M H, Khaja S, Ciecko A E, Hessner M J, and Geurts A M. Gene targeting in NOD mouse embryos using zinc-finger nucleases. *Diabetes.* 2014; 63(1):68-74.
30. Callahan M K, and Wolchok J D. At the bedside: CTLA-4- and PD-1-blocking antibodies in cancer immunotherapy. *Journal of leukocyte biology.* 2013; 94(1):41-53.
31. Sakaguchi S, Miyara M, Costantino C M, and Hafler D A. FOXP3+ regulatory T cells in the human immune system. *Nat Rev Immunol.* 2010; 10(7):490-500.
32. Sivendran S, Chang R, Pham L, Phelps R G, Harcharik S T, Hall L D, Bernardo S G, Moskalenko M M, Sivendran M, Fu Y, et al. Dissection of Immune Gene Networks in Primary Melanoma Tumors Critical for Antitumor Surveillance of Patients with Stage II-III Resectable Disease. *J Invest Dermatol.* 2014.
33. Yadav M, Louvet C, Davini D, Gardner J M, Martinez-Llordella M, Bailey-Bucktrout S, Anthony B A, Sverdrup F M, Head R, Kuster D J, et al. Neuropilin-1 distinguishes natural and inducible regulatory T cells among regulatory T cell subsets in vivo. *J Exp Med.* 2012; 209(10):1713-22, S1-19.
34. Lilleri D, Fornara C, Revello M G, and Gerna G. Human cytomegalovirus-specific memory CD8+ and CD4+ T cell differentiation after primary infection. *The Journal of infectious diseases.* 2008; 198(4):536-43.
35. Zhao J, Zhao J, and Perlman S. Differential effects of IL-12 on Tregs and non-Treg T cells: roles of IFN-gamma, IL-2 and IL-2R. *PLoS One.* 2012; 7(9):e46241.
36. Maecker H T, McCoy J P, and Nussenblatt R. Standardizing immunophenotyping for the Human Immunology Project. *Nat Rev Immunol.* 2012; 12(3):191-200.
37. Xu Z, Zhang T, Zhuang R, Zhang Y, Jia W, Song C, Yang K, Yang A, and Jin B. Increased levels of soluble CD226 in sera accompanied by decreased membrane CD226 expression on peripheral blood mononuclear cells from cancer patients. *BMC Immunol.* 2009; 10(34.
38. Baron U, Floess S, Wieczorek G, Baumann K, Grützkau A, Dong J, Thiel A, Boeld T J, Hoffmann P, Edinger M, et al. DNA demethylation in the human FOXP3 locus discriminates regulatory T cells from activated FOXP3(+) conventional T cells. *Eur J Immunol.* 2007; 37(9):2378-89.
39. Shibuya A, Campbell D, Hannum C, Yssel H, Franz-Bacon K, McClanahan T, Kitamura T, Nicholl J, Sutherland G R, Lanier L L, et al. DNAM-1, a novel adhesion molecule involved in the cytolytic function of T lymphocytes. *Immunity.* 1996; 4(6):573-81.
40. Brusko T M, Hulme M A, Myhr C B, Haller M J, and Atkinson M A. Assessing the in vitro suppressive capacity of regulatory T cells. *Immunol Invest.* 2007; 36(5):607-28.
41. Brusko T M, Wasserfall C H, Clare-Salzler M J, Schatz D A, and Atkinson M A. Functional defects and the influence of age on the frequency of CD4+CD25+ T-cells in type 1 diabetes. *Diabetes.* 2005; 54(5):1407-14.
42. Putnam A L, Brusko T M, Lee M R, Liu W, Szot G L, Ghosh T, Atkinson M A, and Bluestone J A. Expansion of human regulatory T-cells from patients with type 1 diabetes. *Diabetes.* 2009; 58(3):652-62.
43. Ventura A, Meissner A, Dillon C P, McManus M, Sharp P A, Van Parijs L, Jaenisch R, and Jacks T. Cre-lox-regulated conditional RNA interference from transgenes. *Proc Natl Acad Sci USA.* 2004; 101(28):10380-5.
44. Willcox A, Richardson S J, Bone A J, Foulis A K, and Morgan N G. Analysis of islet inflammation in human type 1 diabetes. *Clin Exp Immunol.* 2009; 155(2):173-81.
45. Foulis A K, Liddle C N, Farquharson M A, Richmond J A, and Weir R S. The histopathology of the pancreas in type 1 (insulin-dependent) diabetes mellitus: a 25-year review of deaths in patients under 20 years of age in the United Kingdom. *Diabetologia.* 1986; 29(5):267-74.
46. Hanafusa T, and Imagawa A. Insulitis in human type 1 diabetes. *Annals of the New York Academy of Sciences.* 2008; 1150(297-9.
47. Coppieters K T, Dotta F, Amirian N, Campbell P D, Kay T W, Atkinson M A, Roep B O, and von Herrath M G. Demonstration of islet-autoreactive CD8 T cells in insulitic lesions from recent onset and long-term type 1 diabetes patients. *J Exp Med.* 2012; 209(1):51-60.
48. Buckner J H. Mechanisms of impaired regulation by CD4(+)CD25(+)FOXP3(+) regulatory T cells in human autoimmune diseases. *Nature reviews Immunology.* 2010; 10(12):849-59.
49. Takaki T, Marron M P, Mathews C E, Guttmann S T, Bottino R, Trucco M, Dilorenzo T P, and Serreze D V. HLA-A*0201-Restricted T Cells from Humanized NOD Mice Recognize Autoantigens of Potential Clinical Relevance to Type 1 Diabetes. *J Immunol.* 2006; 176(5):3257-65.
50. Poirot L, Benoist C, and Mathis D. Natural killer cells distinguish innocuous and destructive forms of pancreatic islet autoimmunity. *Proc Natl Acad Sci USA.* 2004; 101 (21):8102-7.
51. Rodacki M, Svoren B, Butty V, Besse W, Laffel L, Benoist C, and Mathis D. Altered natural killer cells in type 1 diabetic patients. *Diabetes.* 2007; 56(1):177-85.
52. Feuerer M, Shen Y, Littman D R, Benoist C, and Mathis D. How punctual ablation of regulatory T cells unleashes an autoimmune lesion within the pancreatic islets. *Immunity.* 2009; 31(4):654-64.
53. de Andrade L F, Smyth M J, and Martinet L. DNAM-1 control of natural killer cells functions through nectin and nectin-like proteins. *Immunol Cell Biol.* 2014; 92(3):237-44.
54. Lloyd A, Vickery O N, and Laugel B. Beyond the antigen receptor: editing the genome of T-cells for cancer adoptive cellular therapies. *Front Immunol.* 2013; 4(221.
55. Zhou X, Bailey-Bucktrout S L, Jeker L T, Penaranda C, Martinez-Llordella M, Ashby M, Nakayama M, Rosenthal W, and Bluestone J A. Instability of the transcription factor Foxp3 leads to the generation of pathogenic memory T cells in vivo. *Nat Immunol.* 2009; 10(9):1000-7.
56. Parker M J, Xue S, Alexander J J, Wasserfall C H, Campbell-Thompson M L, Battaglia M, Gregori S, Mathews C E, Song S, Troutt M, et al. Immune depletion with cellular mobilization imparts immunoregulation and reverses autoimmune diabetes in nonobese diabetic mice. *Diabetes.* 2009; 58(10):2277-84.
57. Atkinson M A. Evaluating preclinical efficacy. *Science translational medicine.* 2011; 3(96):96cm22.
58. Thayer T C, Delano M, Liu C, Chen J, Padgett L E, Tse H M, Annamali M, Piganelli J D, Moldawer L L, and Mathews C E. Superoxide production by macrophages and T cells is critical for the induction of autoreactivity and type 1 diabetes. *Diabetes.* 2011; 60(8):2144-51.
59. Huang Y, Parker M, Xia C, Peng R, Wasserfall C, Clarke T, Wu L, Chowdhry T, Campbell-Thompson M, Williams J, et al. Rabbit polyclonal mouse antithymocyte globulin administration alters dendritic cell profile and function in NOD mice to suppress diabetogenic responses. *Journal of immunology.* 2009; 182(8):4608-15.
60. Brusko T M, Hulme M A, Myhr C B, Haller M J, and Atkinson M A. Assessing the in vitro suppressive capacity of regulatory T cells. *Immunological investigations.* 2007; 36(5-6):607-28.
61. Salomon B, Lenschow D J, Rhee L, Ashourian N, Singh B, Sharpe A, and Bluestone J A. B7/CD28 costimulation is essential for the homeostasis of the CD4+CD25+ immunoregulatory T cells that control autoimmune diabetes. *Immunity.* 2000; 12(4):431-40.
62. Tree T I, Roep B O, and Peakman M. A mini meta-analysis of studies on CD4+CD25+ T cells in human type 1 diabetes: report of the Immunology of Diabetes Society T Cell Workshop. *Ann NY Acad Sci.* 2006; 1079(9-18.
63. Garg G, Tyler J R, Yang J H, Cutler A J, Downes K, Pekalski M, Bell G L, Nutland S, Peakman M, Todd J A, et al. Type 1 diabetes-associated IL2R A variation lowers IL-2 signaling and contributes to diminished CD4+ CD25+ regulatory T cell function. *J Immunol.* 2012; 188(9):4644-53.
64. Schneider A, Rieck M, Sanda S, Pihoker C, Greenbaum C, and Buckner J H. The effector T cells of diabetic subjects are resistant to regulation via CD4+ FOXP3+ regulatory T cells. *J Immunol.* 2008; 181(10):7350-5.
65. Zheng Y, Josefowicz S, Chaudhry A, Peng X P, Forbush K, and Rudensky A Y. Role of conserved non-coding DNA elements in the Foxp3 gene in regulatory T-cell fate. *Nature.* 2010; 463(7282):808-12.
66. Campbell-Thompson M L, Heiple T, Montgomery E, Zhang L, and Schneider L. Staining protocols for human pancreatic islets. *J Vis Exp.* 201263):e4068.
67. Brusko T, and Atkinson M. Treg in type 1 diabetes. *Cell Biochem Biophys.* 2007; 48(2-3):165-75.
68. Brusko T, and Bluestone J. Clinical application of regulatory T cells for treatment of type 1 diabetes and transplantation. *Eur J Immunol.* 2008; 38(4):931-4.
69. Hoffmann P, Boeld T J, Eder R, Huehn J, Floess S, Wieczorek G, Olek S, Dietmaier W, Andreesen R, and Edinger M. Loss of FOXP3 expression in natural human CD4+CD25+ regulatory T cells upon repetitive in vitro stimulation. *Eur J Immunol.* 2009; 39(4):1088-97.
70. Hoffmann P, Eder R, Boeld T J, Doser K, Piseshka B, Andreesen R, and Edinger M. Only the CD45RA+ subpopulation of CD4+CD25high T cells gives rise to homogeneous regulatory T-cell lines upon in vitro expansion. *Blood.* 2006; 108(13):4260-7.
71. Zhou X, Bailey-Bucktrout S, Jeker L T, and Bluestone J A. Plasticity of CD4(+) FoxP3(+) T cells. *Curr Opin Immunol.* 2009; 21(3):281-5.
72. Liu W, Putnam A L, Xu-Yu Z, Szot G L, Lee M R, Zhu S, Gottlieb P A, Kapranov P, Gingeras T R, de St Groth B F, et al. CD127 expression inversely correlates with FoxP3 and suppressive function of human CD4+ T reg cells. *J Exp Med.* 2006; 203(7):1701-11.
73. Battaglia M, Stabilini A, and Roncarolo M G. Rapamycin selectively expands CD4+CD25+FoxP3+ regulatory T cells. *Blood.* 2005; 105(12):4743-8.
74. Golovina T N, Mikheeva T, Brusko T M, Blazar B R, Bluestone J A, and Riley J L. Retinoic acid and rapamycin differentially affect and synergistically promote the ex vivo expansion of natural human T regulatory cells. *PLoS One.* 2011; 6(1):e15868.
75. Asseman C, Mauze S, Leach M W, Coffman R L, and Powrie F. An essential role for interleukin 10 in the function of regulatory T cells that inhibit intestinal inflammation. *J Exp Med.* 1999; 190(7):995-1004.
76. Belghith M, Bluestone J A, Barriot S, Megret J, Bach J F, and Chatenoud L. TGF-beta-dependent mechanisms mediate restoration of self-tolerance induced by antibodies to CD3 in overt autoimmune diabetes. *Nat Med.* 2003; 9(9): 1202-8.
77. de la Rosa M, Rutz S, Dorninger H, and Scheffold A. Interleukin-2 is essential for CD4+CD25+ regulatory T cell function. *Eur J Immunol.* 2004; 34(9):2480-8.
78. Yates J, Rovis F, Mitchell P, Afzali B, Tsang J Y, Garin M, Lechler R I, Lombardi G, and Garden O A. The maintenance of human CD4+CD25+ regulatory T cell function: IL-2, IL-4, IL-7 and IL-15 preserve optimal suppressive potency in vitro. *Int Immunol.* 2007; 19(6): 785-99.
79. Asano, M., M. Toda, N. Sakaguchi, and S. Sakaguchi. 1996. Autoimmune disease as a consequence of developmental abnormality of a T cell subpopulation. *J. Exp. Med.* 184: 387-396.
80. Bennett, C. L., J. Christie, F. Ramsdell, M. E. Brunkow, P. J. Ferguson, L. Whitesell, T. E. Kelly, F. T. Saulsbury, P. F. Chance, and H. D. Ochs. 2001. The immune dysregulation, polyendocrinopathy, enteropathy, X-linked syndrome (IPEX) is caused by mutations of FOXP3. *Nat. Genet.* 27: 20-21.
81. Brusko, T. M., A. L. Putnam, and J. A. Bluestone. 2008. Human regulatory T cells: role in autoimmune disease and therapeutic opportunities. *Immunological reviews* 223: 371-390.
82. Fife, B. T., and J. A. Bluestone. 2008. Control of peripheral T-cell tolerance and autoimmunity via the CTLA-4 and PD-1 pathways. *Immunological reviews* 224: 166-182.
83. O'Shea, J. J., and W. E. Paul. 2010. Mechanisms underlying lineage commitment and plasticity of helper CD4+ T cells. *Science* 327: 1098-1102.
84. Yang, X. P., K. Ghoreschi, S. M. Steward-Tharp, J. Rodriguez-Canales, J. Zhu, J. R. Grainger, K. Hirahara, H. W. Sun, L. Wei, G. Vahedi, Y. Kanno, J. J. O'Shea, and A. Laurence. 2011. Opposing regulation of the locus encoding IL-17 through direct, reciprocal actions of STAT3 and STAT5. *Nat Immunol* 12: 247-254.
85. Bailey-Bucktrout, S. L., and J. A. Bluestone. 2011. Regulatory T cells: stability revisited. *Trends in immunology* 32: 301-306.
86. McClymont, S. A., A. L. Putnam, M. R. Lee, J. H. Esensten, W. Liu, M. A. Hulme, U. Hoffmuller, U. Baron, S. Olek, J. A. Bluestone, and T. M. Brusko. 2011. Plasticity of human regulatory T cells in healthy subjects and patients with type 1 diabetes. *Journal of immunology* 186: 3918-3926.
87. Dominguez-Villar, M., C. M. Baecher-Allan, and D. A. Hafler. 2011. Identification of T helper type 1-like, Foxp3+ regulatory T cells in human autoimmune disease. *Nature medicine* 17: 673-675.
88. Beriou, G., C. M. Costantino, C. W. Ashley, L. Yang, V. K. Kuchroo, C. Baecher-Allan, and D. A. Hafler. 2009. IL-17-producing human peripheral regulatory T cells retain suppressive function. *Blood* 113: 4240-4249.
89. Thornton, A. M., P. E. Korty, D. Q. Tran, E. A. Wohlfert, P. E. Murray, Y. Belkaid, and E. M. Shevach. 2010. Expression of Helios, an Ikaros transcription factor family member, differentiates thymic-derived from peripherally induced Foxp3+T regulatory cells. *Journal of immunology* 184: 3433-3441.
90. Bin Dhuban, K., E. d'Hennezel, E. Nashi, A. Bar-Or, S. Rieder, E. M. Shevach, S. Nagata, and C. A. Piccirillo. 2015. Coexpression of TIGIT and FCRL3 Identifies Helios+ Human Memory Regulatory T Cells. *Journal of immunology.*
91. Yu, X., K. Harden, L. C. Gonzalez, M. Francesco, E. Chiang, B. Irving, I. Tom, S. Ivelja, C. J. Refino, H. Clark, D. Eaton, and J. L. Grogan. 2009. The surface protein TIGIT suppresses T cell activation by promoting the generation of mature immunoregulatory dendritic cells. *Nature immunology* 10: 48-57.
92. Johnston, R. J., L. Comps-Agrar, J. Hackney, X. Yu, M. Huseni, Y. Yang, S. Park, V. Javinal, H. Chiu, B. Irving, D. L. Eaton, and J. L. Grogan. 2014. The immunoreceptor TIGIT regulates antitumor and antiviral CD8(+) T cell effector function. *Cancer cell* 26: 923-937.
93. Hill, J. A., M. Feuerer, K. Tash, S. Haxhinasto, J. Perez, R. Melamed, D. Mathis, and C. Benoist. 2007. Foxp3 transcription-factor-dependent and -independent regulation of the regulatory T cell transcriptional signature. *Immunity* 27: 786-800.
94. Hoffmann, P., T. J. Boeld, R. Eder, J. Huehn, S. Floess, G. Wieczorek, S. Olek, W. Dietmaier, R. Andreesen, and M. Edinger. 2009. Loss of FOXP3 expression in natural human CD4+CD25+ regulatory T cells upon repetitive in vitro stimulation. *Eur J Immunol* 39: 1088-1097.
95. Riley, J. L., C. H. June, and B. R. Blazar. 2009. Human T regulatory cell therapy: take a billion or so and call me in the morning. *Immunity* 30: 656-665.
96. Koch, M. A., K. R. Thomas, N. R. Perdue, K. S. Smigiel, S. Srivastava, and D. J. Campbell. 2012. T-bet(+) Treg cells undergo abortive Th1 cell differentiation due to impaired expression of IL-12 receptor beta2. *Immunity* 37: 501-510.
97. Zheng, Y., A. Chaudhry, A. Kas, P. deRoos, J. M. Kim, T. T. Chu, L. Corcoran, P. Treuting, U. Klein, and A. Y. Rudensky. 2009. Regulatory T-cell suppressor program co-opts transcription factor IRF4 to control T(H)2 responses. *Nature* 458: 351-356.
98. Gagliani, N., C. F. Magnani, S. Huber, M. E. Gianolini, M. Pala, P. Licona-Limon, B. Guo, D. R. Herbert, A. Bulfone, F. Trentini, C. Di Serio, R. Bacchetta, M. Andreani, L. Brockmann, S. Gregori, R. A. Flavell, and M. G. Roncarolo. 2013. Coexpression of CD49b and LAG-3 identifies human and mouse T regulatory type 1 cells. *Nature medicine* 19: 739-746.

99. Cretney, E., A. Xin, W. Shi, M. Minnich, F. Masson, M. Miasari, G. T. Belz, G. K. Smyth, M. Busslinger, S. L. Nutt, and A. Kallies. 2011. The transcription factors Blimp-1 and IRF4 jointly control the differentiation and function of effector regulatory T cells. *Nature immunology* 12: 304-311.

100. Callahan, M. K., and J. D. Wolchok. 2013. At the bedside: CTLA-4- and PD-1-blocking antibodies in cancer immunotherapy. *Journal of leukocyte biology* 94: 41-53.

101. Ardolino, M., A. Zingoni, C. Cerboni, F. Cecere, A. Soriani, M. L. Iannitto, and A. Santoni. 2011. DNAM-1 ligand expression on Ag-stimulated T lymphocytes is mediated by ROS-dependent activation of DNA-damage response: relevance for NK-T cell interaction. *Blood* 117: 4778-4786.

We claim:

1. A method for isolating a regulatory T cell (Treg) from a subject, the method comprising the steps of:
   a) analyzing a sample of cells obtained from the subject to determine the level of expression of polypeptides and/or polynucleotides corresponding to proteins CD4, CD25, CD226, and CD127, and
   b) isolating, as the Treg, a cell which:
      i) expresses CD4 and CD25, and
      ii expresses low levels of CD127 or does not express CD127, and/or
      iii expresses low levels of CD226 or does not express CD226.

2. The method of claim 1, wherein the method comprises analyzing the level of expression proteins CD127, CD4, CD25, and CD226.

3. The method of claim 2, wherein the step of isolating comprises isolating the cell which:
   i) expresses CD4 and CD25,
   ii) expresses low levels of CD127 or does not express CD127, and
   iii) expresses low levels of CD226 or does not express CD226.

4. The method of claim 2, wherein the step of isolating comprises isolating the cell which:
   i) expresses CD4 and CD25,
   ii) expresses low levels of CD127 or does not express CD127, and
   iv) does not express CD226.

5. The method of claim 1, wherein the step of isolating comprises isolating the cell which:
   i) expresses CD4 and CD25, and
   iii) expresses low levels of CD226 or does not express CD226.

6. The method according to claim 1, wherein the step of analyzing the level of expression proteins comprises the steps of:
   (A) obtaining the sample of cells from the subject;
   (B) contacting the sample of cells with antibodies directed towards CD4, CD25, and CD226 to allow binding of the antibodies to the corresponding proteins;
   (C) subjecting the sample of cells to flow cytometry;
   (D) examining the flow cytometry signal for the expression of CD4, CD25, and CD226, and
   (E) isolating, as the Treg, the cell which: i) expresses CD4 and CD25, and iii) expresses low levels of CD226 or does not express CD226.

7. The method of claim 1, the method further comprises proliferating the Treg in vitro.

8. A method according to claim 7, further comprising administering the Treg to the subject.

* * * * *

SEQUENCE LISTING

```
<160> NUMBER OF SEQ ID NOS: 7

<210> SEQ ID NO 1
<211> LENGTH: 136
<212> TYPE: DNA
<213> ORGANISM: Artificial
<220> FEATURE:
<223> OTHER INFORMATION: amplicon for real-time PCR assay for TSDR
      fragment of foxp3 gene

<400> SEQUENCE: 1
ggtctgcatc tgggccctgt tgtcacagcc cccgacttgc ccagatttt ccgccattga      60 cgtcatggcg gccggatgcg ccgggcttca tcgacaccac ggaggaagag aagagggcag    120
ataccccacc ccacag                                                    136

<210> SEQ ID NO 2
<211> LENGTH: 37
<212> TYPE: DNA
<213> ORGANISM: Artificial
<220> FEATURE:
<223> OTHER INFORMATION: FOXP3_TSDRfwd primer

<400> SEQUENCE: 2
atatttttag atagggatat ggagatgatt tgtttgg                              37

<210> SEQ ID NO 3
<211> LENGTH: 31
<212> TYPE: DNA
<213> ORGANISM: Artificial
<220> FEATURE:
<223> OTHER INFORMATION: FOXP3_TSDRrev primer

<400> SEQUENCE: 3
aataaacatc acctaccaca tccaccaaca c                                    31

<210> SEQ ID NO 4
<211> LENGTH: 29
<212> TYPE: DNA
<213> ORGANISM: Artificial
<220> FEATURE:
<223> OTHER INFORMATION: probe used for PCR amplification, TSDR-Forward

<400> SEQUENCE: 4
ggtttgtatt tgggttttgt tgttatagt                                       29

<210> SEQ ID NO 5
<211> LENGTH: 34
<212> TYPE: DNA
<213> ORGANISM: Artificial
<220> FEATURE:
<223> OTHER INFORMATION: probe used for PCR amplification, TSDR-Reverse

<400> SEQUENCE: 5
ctataaaata aaatatctac cctcttctct tcct                                 34
```

```
<210> SEQ ID NO 6
<211> LENGTH: 14
<212> TYPE: DNA
<213> ORGANISM: Artificial
<220> FEATURE:
<223> OTHER INFORMATION: probe for methylated target sequence detection

<400> SEQUENCE: 6
cggtcggatg cgtc                                                       14

<210> SEQ ID NO 7
<211> LENGTH: 18
<212> TYPE: DNA
<213> ORGANISM: Artificial
<220> FEATURE:
<223> OTHER INFORMATION: probe for unmethylated target sequence
      detection

<400> SEQUENCE: 7
tggtggttgg atgtgttg                                                   18
```